(12) United States Patent
Raushel et al.

(10) Patent No.: US 10,301,608 B2
(45) Date of Patent: May 28, 2019

(54) VARIANTS OF PHOSPHOTRIESTERASE FOR THE HYDROLYSIS AND DETOXIFICATION OF NERVE AGENTS

(71) Applicant: The Texas A&M University System, College Station, TX (US)

(72) Inventors: Frank M. Raushel, College Station, TX (US); Andrew N. Bigley, North Zulch, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/320,490

(22) PCT Filed: Jun. 19, 2015

(86) PCT No.: PCT/US2015/036745
§ 371 (c)(1),
(2) Date: Dec. 20, 2016

(87) PCT Pub. No.: WO2015/196106
PCT Pub. Date: Dec. 23, 2015

(65) Prior Publication Data
US 2017/0218348 A1    Aug. 3, 2017

Related U.S. Application Data

(60) Provisional application No. 62/015,156, filed on Jun. 20, 2014.

(51) Int. Cl.
*C12N 9/16*    (2006.01)
*A62D 3/02*    (2007.01)
*A62D 101/02*    (2007.01)
*A62D 101/26*    (2007.01)

(52) U.S. Cl.
CPC ................ *C12N 9/16* (2013.01); *A62D 3/02* (2013.01); *C12Y 301/03008* (2013.01); *C12Y 301/08001* (2013.01); *A62D 2101/02* (2013.01); *A62D 2101/26* (2013.01)

(58) Field of Classification Search
None
See application file for complete search history.

(56) References Cited

FOREIGN PATENT DOCUMENTS

WO    2014096402 A1    6/2014

OTHER PUBLICATIONS

Extended European Search Report dated Oct. 17, 2017, in European Application No. 15809669.3.
Ashani Y.; Pistinner, S. Toxicol. Sci, 2004, 77, 358.
Afriat-Jurnou, Livnat, et al.; Reconstructing a Missing Link in the Evolution of a Recently Diverged Phosphotriesterase by Active-Site Loop Remodeling; Biochemistry; 2012; pp. 6047-6055; American Chemical Society.
Aubert, Sarah D.; et al; Mechanism for the Hydrolysis of Organophosphates by the Bacterial Phospotriesterdase; Biochemistry; 2004; pp. 5707-5715; vol. 43; American Chemical Society.
Adams, Paul D., et al.; PHENIX: a comprehensive Python-based system for macromolecular structure solution; Acta Crystallogr., Sect. D: Biol. Crystallogr.; 2010; pp. 213-221; vol. D66.
Amitai, Gavriel; et al.; Synthesis and properties of 2-S-(N,N-dialkylarnino)ethyl)thio-1,3,2-dioxaphosphorinane 2-oxide and of the corresponding quaternary derivatives as potential nontoxic antiglaucoma agents; J. Med. Chem.; 1976; pp. 810-813; vol. 19 No. 6.
Bigley, A. N., Xu, C., Henderson, T. J., Harvey, S. F., and Raushel, F, M. (2013) Enzymatic neutralization of the chemical warfare agent VX: evolution of phosphotriesterase for phosphorothiolate hydrolysis, J. Am. Chem. Soc. 135, 10426-10432.
Batley, Michael, et al.; P NMR Reference Standards for Aqueous Samples; J. Magn. Reson.; 1982; pp. 172-174; vol. 49; Academic Press, Inc.
Benschop, H. F., et al.; Nerve agent stereoisomers. analysis, isolation and toxicology; Acc. Chem. Res.; 1988; pp. 368-374; vol. 21; American Chemical Society.
Cheng, T-C, et al.; Nucleotide sequence of a gene encoding an organophosphorus nerve agent degrading enzyme from Alteromonas haloplanktis; J. Ind. Microbiol. Biotechnol.; 1997 pp. 49-55; vol. 18.; Society for Industrial Microbiology.
Chen-Goodspeed, Misty, et al.; Structural determinants of the substrate and stereochemical specificity of phosphotriesterase; Biochemistry; 2001; pp. 1325-1331; vol. 40; American Chemical Society.
Caldwell, Steven R.; et al.; Limits of Diffusion in the Hydrolysis of Substrates by the Phosphotriesterase from Pseudomonas diminuta; Biochemistry; 1991; pp. 7438-7444; vol. 30; American Chemical Society.
Cherny, Izhack, et al.; Engineering V-type nerve agents detoxifying enzymes using computationally focused libraries; ACS chem. Biol.; 2013; pp. 2394-2403; vol. 8; American Chemical Society.
Columbus, Ishay, et al.; VX Fate on Common Matrices: Evaporation versus Degradation; Environ, Sci. Technol.; 2012; pp. 3921-3927; vol. 46.
Emsley, Paul, et al.; Coot: model-building tools for molecular graphics; Acta Crystallogr., Sect. D: Biol. Crystallogr.; 2004; pp. 2126-2132; vol. D60.
Goldsmith, Moshe, et al.; Avoiding and controlling double transformation artifacts; Protein Eng. Del. Sel.; 2007; pp. 315-318; vol. 20 No. 7; Oxford University Press.
Gupta, Rinkoo D., et al.; Directed evolution of hyrolases for prevention of G-type nerve agent intoxication; Nat. Chem. Biol.; Feb. 2011; pp. 120-125; vol. 7; Nature Publishing Group.

(Continued)

*Primary Examiner* — Hope Robinson
(74) *Attorney, Agent, or Firm* — Ramey & Schwaller, LLP; William P. Ramey, Esq.; Melissa D. Schwaller, Esq.

(57) ABSTRACT

Variants of phosphotriesterase have been created that exhibit enhanced hydrolysis of V-type and G-type nerve agents over wild-type phosphotriesterase. V- and G-type nerve agents have an $S_P$ and $R_P$ enantiomer. The $S_P$ enantiomers are more toxic. V-type nerve agents are among the most toxic substances known. Variants of phosphotriesterase can prefer to hydrolyze one enantiomer of VX over the other enantiomer.

1 Claim, 20 Drawing Sheets

Specification includes a Sequence Listing.

(56) References Cited

OTHER PUBLICATIONS

Hong, Suk-Bong, et al.; Metal-Substrate Interactions Facilitate the Catalytic Activity of the Bacterial Phosphotriesterase; Biochemistry; 1996; pp. 10904-10912; vol. 35; American Chemical Society.

Horton, Rorbert M., et al.; Engineering hybrid genes without the use of restriction enzymes: gene splicing by overlap extension; Gene; 1989; pp. 61-68; vol. 77; Elsevier Science Publishers B.V. (Biomedical Division).

Kirby, Stephen D., et al.; Human paraoxonase double mutants hydrolyze V and G class organophosphorus nerve agents; Chem. Biol. Interact.; 2013; pp. 181-185; vol. 203; Elsevier Ireland Ltd.

Lai, Kaihua, et al,; Rational Enzyme Design: Computer Modeling and Site-directed Mutagenesis for the Modification of Catalytic Specificity in Organophosphorus Hydrolase; Chimia; 1996; pp. 430-431; vol. 50; Neue Schweizerische Chemische Gessalschoft.

Leikin, J. B., et al.; A review of nerve agent exposure for the critical care physician; Crit. Care Med.; 2002; pp. 2346-2354; vol. 10 No. 10; Lippincott Williams & Wilkins.

Maxwell; D. M., et al.; Acetylcholinesterase inhibition: does it explain the toxicity of organophosphorus compounds?; Mol. Toxicol.; 2006; pp. 756-760; vol. 80; Springer-Verlag.

Mee-Hie Cho, Catherine, et al.; Functional analysis of organophosphorus hydrolase variants with high degradation activity towards organophosphate pesticides; Protein Eng., Des. Sel.; 2006; pp. 99-105; vol. 19 No. 3; Oxford University Press.

Meizer, Marco, et al.; Reversed Enantioselectivity of Diisopropyl Fluorophosphatase against Organophosphorus Nerve Agents by Rational Design; J. Am. Chem. Soc.; Nov. 6, 2009; pp. 17226-17232; vol. 131; American Chemical Society.

Michaelis, L., et al.; Die kinetik der invertinwirkung; Biochem. Z.; 1913; pp. 333-369; vol. 49.

Ordentilich A.; Barak, D.; Sod-Moriah, G.; Kaplan, D.; Mizrahi, D.; Segall, Y.; Kronman, C.; Karton, Y.; Lazar, A.; Marcus, D.; Velan, B.; Shafferman, A. Biochemistry 2004, 43, 11255.

Otwinowski, Zbyszek, et al.; Processing of X-ray diffraction data collected in oscillation mode; Methods Enzymol.; 1997; pp. 307-326; vol. 276; Academic Press, Inc.

Rastogi, Vipin K., et al.; Enzymatic Hydrolysis of Russian-VX by Organophosphorus Hydrolase; Biochem. Bioph. Res. Co.; 1997; pp. 294-296; vol. 241; Academic Press.

Reeves, T.E., et al.; Balancing the stability and the catalytic specificities of OP hydrolases with enhanced V-agent activities; Protein Eng. Des. Sel.; 2008; pp. 405-412; vol. 21 No. 6.

Roodveldt, C., et al.; Directed evolution of phosphotriesterase from Pseudomonas diminuta for heterologous expression in *Escherichia coli* results in stabilization of the metal-free state; Protein Eng., Des. Sel.; 2005; pp. 51-58; vol. 18 No. 1; Oxford University Press. 7.

Rosman, MD, Yossi, et al.; Lessons Learned from the Syrian Sarin Attack: Evaluation of a Clinical Syndrome Through Social Media; Ann. Intern. Med.; 2014; pp. 644-648; vol. 160 No. 9; American College of Physicians.

Saxena, Ashima, et al.; Pilot-scale production of human serum butyrylcholinesterase suitable for use as a bioscavenger against nerve agent toxicity; Process Biochemistry; 2010; pp. 1313-1318; Elsevier Inc.

Saxena, Ashima, et al.; ; Prophylaxis with human serum butyrylchoiinesteratse protects guinea pigs exposed to multiple lethal doses of soman or VX; Process Biochemistry; 2011; pp. 164-169; Elsevier Inc.

Schofield, D.A.; et al.; Generation of a mutagenized organophosphorus hydrolase for the biodegradation of the organophosphate pesticides malathion and demeton-S; J. Appl. Microbiol.; 2010; pp. 548-557; vol. 109; Guild Associates Inc.

Shaka, A.J., et al.; Evaluation of a New Broadband Decoupling Sequence: WALTZ-16; J. Magn. Reson.; 1983; pp. 313-340; vol. 53; Academic Press, Inc.

Trott, Oleg, et al.; AutoDock Vina: Improving the speed and accuracy of docking with a new scoring function, efficient optimization, and multithreading; J. Comput. Chem.; 2010; pp. 455-461; Wiley Periodicals, Inc.

Tsai, Ping-Chuan, et al.; Stereoselective Hydrolysis of Organophosphate Nerve Agents by the Bacterial Phosphotriesterase; Biochemistry; 2010; pp. 7978-7987; vol. 49; ACS Publishing.

Tsai, Ping-Chuan, et al.; Enzymes for the Homeland Defense: Optimizing Phophotriesterase for the Hydrolysis of Organophosphate Nerve Agents; Biochemistry; 2012; pp. 6463-6475; vol. 51; ACS Publications.

Vanhooke, Janeen L., et al.; Three-Dimensional Structure of the Zinc-Containing Phosphotriesterase with the Bound Substrate Analog Diethyl 4-Methylbenzylphosphonate; Biochemistry; 1996; pp. 6020-6025; vol. 35; American Chemical Society.

Yang Y. C. Chem. Ind. 1995, 9, 334.

Yang, Yu-Chu; Chemical Detoxification of Nerve Agent VX; Acc. Chem. Res.; 1999; pp. 109-115; vol. 32 No. 2.

Caldwell, Steven R., et al.; Transition-State Structures for Enzymatic and Alkaline Phosphotriester Hydrolysis; Biochemistry; 1991; pp. 7444-7450; vol. 30; American Chemical Society.

Thoden, James B., et al.; Molecular Structure of Dihydroorotase: A Paradigm for Catalysis through the Use of a Binuclear Metal Center; Biochemistry; Jun. 19, 2001; pp. 6989-6997; American Chemical Society.

Examination Report dated Jul. 2, 2018, in European Application No. 15809669.3.

International Search Report and Written Opinion dated Sep. 3, 2015, in International Application No. PCT/US15/36745.

International Preliminary Report on Patentability dated Dec. 29, 2016, in International Application No. PCT/US15/36745.

```
                                    10         20         30         40         50         60
                                    MS IGTGDRINTV RGPITISEAG FTLTHEHICG
        70         80         90        100        110        120
SSAGFLRAWP EFFGSRKALA EKAVRGLRRA RAAGVRTIVD VSTFDIGRDV SLLAEVSRAA
       130        140        150        160        170        180
DVHIVAATGL WFDPPLSMRL RSVEELTQFF LREIQYGIED TGIRAGIIKV ATTGKATPFQ
       190        200        210        220        230        240
ELVLKAAARA SLATGVPVTT HTAASQRDGE QQAAIFESEG LSPSRVCIGH SDDTDDLSYL
       250        260        270        280        290        300
TALAARGYLI GLDHIPHSAI GLEDNASASA LLGIRSWQTR ALLIKALIDQ GYMKQIL VSN
       310        320        330        340        350        360
DWLFGFSSYV TNIMDVMDRV NPDGMAFIPL RVIPFLREKG VPQEILAGIT VTNPARFLSP

TLRAS (SEQ ID NO.: 1)
Residue 365
```

Figure 14

VARIANTS OF PHOSPHOTRIESTERASE FOR THE HYDROLYSIS AND DETOXIFICATION OF NERVE AGENTS

GOVERNMENT LICENSE RIGHTS

This invention was made with government support under GM068550 awarded by National Institutes of Health and under HDTRA1-14-1-0004 awarded by the Defense Threat Reduction Agency. The government has certain rights in the invention.

This Application contains a sequence listing submitted as a text file via EFS Web, herein incorporated by reference.

FIELD

The disclosure relates generally to chemical warfare. More specifically, the disclosure relates to detoxification of organophosphate nerve agents.

BACKGROUND

The G-type (sarin, cyclosarin, and soman) and V-type (VX and VR) organophosphonates are among the most toxic compounds known. The toxicity of these compounds is due to their ability to inactivate acetylcholine esterase, an enzyme required for proper nerve function.(1) Acetylcholine esterase breaks down the neurotransmitter acetylcholine into acetic acid and choline. Acetylcholine conducts a nerve impulse between the nerve and the muscle, stimulating the muscle. The organophosphonate binds to the hydroxyl group on a serine at a binding site on acetylcholine esterase, preventing acetylcholine from binding at that site. If acetylcholine esterase is inhibited by an organophosphonate, acetylcholine builds up at the synapses and neuromuscular junctions and the receptor is desensitized resulting in paralysis with an estimated lethal dermal exposure of about 6 milligrams of VX for an average human.

Contact with VX is about 200-fold more toxic than soman (GD) and 300-fold more toxic than sarin (GB).(2) The extreme potential for acute toxicity with VX is due, in part, to the low volatility of this compound, which allows it to persist indefinitely on common surfaces.(3) Methods currently utilized for the destruction of organophosphate nerve agents include high temperature incineration and treatment with strong base or concentrated bleach.(4,5) Medical treatment of VX toxicity is currently limited to the injection of atropine, which reduces neurological symptoms, and oximes, which can help to reactivate the inactivated acetylcholine esterase.(2) Butyrylcholine esterase, which is closely related to acetylcholine esterase, has proven effective in animal models as a stoichiometric scavenger of VX.(6) However, the large amount of enzyme required for treatment with a stoichiometric scavenger, and the limited supply of this protein, have prevented butyrylcholine esterase from being an effective antidote for medical use.(7,8)

Enzymatic hydrolysis of nerve agents provides numerous advantages over harsh physical or chemical methods of decontamination and could provide a catalytic antidote for medical use. Enzymes such as organophosphorus acid anhydrolase (OPAA), diisopropyl-fluorophospatase (DFPase), and human paraoxonase (PON1) can hydrolytically neutralize the various G-type agents, (9,10,11,12) but except for PON1, they have no activity against the V-type agents.(11)

The enzyme phosphotriesterase (PTE) is capable of hydrolyzing a wide variety of organophosphonates including both the G-type and V-type nerve agents.(13,14) A substrate for PTE, the insecticide paraoxon (FIG. 3F) has an enzymatic efficiency that approaches the limits of diffusion ($k_{cat}/K_m \sim 10^8$ $M^{-1}$ $s^{-1}$).(15)

The high toxicity and environmental persistence of VX makes the development of novel decontamination methods particularly important. PTE is capable of hydrolyzing VX. The enzymatic efficiency of PTE for VX is more than 5-orders of magnitude lower than with paraoxon. For the hydrolysis of the G-type agents by PTE, the values of $k_{cat}/K_m$ are between $10^4$ and $10^5$ $M^{-1}$ $s^{-1}$.(13)

The G- and V-type nerve agents all contain a chiral phosphorus center where the $S_P$-enantiomers are significantly more toxic than the corresponding $R_P$-enantiomers. (16,17) In general, wild-type PTE preferentially hydrolyzes the $R_P$-enantiomers of these compounds. The overall selectivity depends on the relative size of the substituents attached to the phosphorus center, with larger differences in size resulting in greater stereoselectivity.(18)

Chiral chromophoric analogues of the G-type agents have been utilized to guide the evolution of PTE for the identification of variants that prefer the more toxic $S_P$-enantiomers of sarin, cyclosarin, and soman.(13,16,18) The catalytic activity of PTE for the more toxic $S_P$-enantiomer of cyclosarin (GF) has been increased by more than 4-orders of magnitude.(13) The catalytic efficiencies for the hydrolysis of the more toxic $S_P$-enantiomers by the enhanced variants of PTE for the hydrolysis of GB, GD, and GF approach $10^6$ $M^{-1}$ $s^{-1}$.(13)

Unfortunately, the activity of PTE against the V-type agents is about 3-orders of magnitude lower than that with the G-type agents ($k_{cat}/K_m < 10^3$ $M^{-1}$ $s^{-1}$). (14, 19). The net rate of VX hydrolysis by PTE is thought to be limited more by the chemistry of the leaving group than by the stereochemistry of the phosphorus center.(13,14,20) The X-ray crystal structure of PTE shows that this enzyme folds as a distorted $(\beta/\alpha)_8$-barrel and that the bulk of the active site is formed from the 8 loops that connect the core $\beta$-strands to the subsequent $\alpha$-helices.(21)

The twelve residues which make up the substrate binding site of PTE can be subdivided into three pockets that accommodate the small, large and leaving-group moieties of the substrate.(21)

The residues in the active site have been shown to be largely responsible for the observed substrate specificity. (22) Loop-7 is the largest of the loops that contribute to the substrate binding site, and is known to tolerate substantial sequence variation.(18,21,23) Previous attempts to evolve PTE for the hydrolysis of VX have utilized the insecticide demeton-S with modest success.(24,25)

It would be advantageous to have enzymes that could optimize the hydrolysis of organophosphate nerve agents, including a new analogue and mutation strategies to optimize PTE for the hydrolysis of G-agents and V-agents such as VX.

SUMMARY

An embodiment of the disclosure is a synthetic amino acid sequence comprising the synthetic amino acid sequence of VQFL (SEQ ID NO: 2), capable of hydrolyzing organophosphates. In an embodiment, a synthetic DNA sequence encodes the synthetic amino acid sequence of SEQ ID NO: 2. In another embodiment, a synthetic cDNA sequence comprises the coding sequence of the synthetic DNA. In another embodiment, a plasmid comprises the synthetic DNA sequence.

An embodiment of the disclosure is a method of hydrolysis of an organophosphate nerve agent comprising contacting an organophosphate nerve agent with the synthetic amino acid sequence SEQ ID NO: 2; and hydrolyzing the organophosphate nerve agent. In an embodiment, the organophosphate is VX. In another embodiment, the organophosphate is VR. In yet another embodiment, the organophosphate is selected from the group consisting of GB, GD, and GF.

An embodiment of the disclosure is a system for detoxifying an organophosphate nerve agent comprising contacting the synthetic amino acid sequence of SEQ ID NO: 2 with an organophosphate nerve agent.

An embodiment of the disclosure is a kit for detoxifying an organophosphate nerve agent comprising the synthetic amino acid sequence of SEQ ID NO: 2.

An embodiment of the disclosure is the synthetic amino acid sequence of claim 1, further comprising mutations I106C (CVQFL (SEQ ID NO: 3)). In an embodiment, a synthetic DNA sequence encodes the synthetic amino acid sequence of SEQ ID NO: 3. In an embodiment, a synthetic cDNA sequence comprises the coding sequence of the synthetic DNA sequence. In another embodiment, a plasmid comprises the synthetic DNA sequence.

An embodiment of the disclosure is a method of hydrolysis of an organophosphate nerve agent comprising contacting an organophosphate nerve agent with the synthetic amino acid sequence of SEQ ID NO: 3; and hydrolyzing the organophosphate nerve agent. In an embodiment, the organophosphate is VX. In another embodiment, the organophosphate is VR. In yet another embodiment, the organophosphate is selected from the group consisting of GB, GD, and GF.

An embodiment of the disclosure is a system for detoxifying an organophosphate nerve agent comprising contacting the synthetic amino acid sequence of SEQ ID NO: 3 with an organophosphate nerve agent.

An embodiment of the disclosure is a kit for detoxifying an organophosphate nerve agent comprising the synthetic amino acid sequence of SEQ ID NO: 3.

An embodiment of the disclosure is the synthetic amino acid sequence of claim 1, further comprising mutations A80V, K185R, and I274N (VRN-VQFL (SEQ ID NO: 4)). In an embodiment, the synthetic DNA sequence encodes the synthetic amino acid sequence of SEQ ID NO: 4. In another embodiment, the synthetic cDNA sequence comprises the coding sequence of the synthetic DNA sequence. In yet another embodiment, a plasmid comprises the synthetic DNA sequence.

An embodiment of the disclosure is a method of hydrolysis of an organophosphate nerve agent comprising contacting an organophosphate nerve agent with the synthetic amino acid sequence of SEQ ID NO: 4; and hydrolyzing the organophosphate nerve agent. In an embodiment, the organophosphate is VX. In an embodiment, the organophosphate is VR. In an embodiment, the organophosphate is selected from the group consisting of GB, GD, and GF.

An embodiment of the disclosure is a system for detoxifying an organophosphate nerve agent comprising contacting the synthetic amino acid sequence of SEQ ID NO: 4 with an organophosphate nerve agent.

An embodiment of the kit for detoxifying an organophosphate nerve agent comprising the synthetic amino acid sequence of SEQ ID NO: 4.

An embodiment of the disclosure is the synthetic amino acid sequence comprising the synthetic amino acid sequence of L7ep-3a (SEQ ID NO: 5). In an embodiment, a synthetic DNA sequence encodes the synthetic amino acid sequence of SEQ ID NO: 5. In an embodiment, a synthetic cDNA sequence comprises the coding sequence of the synthetic DNA sequence. In yet another embodiment, a plasmid comprises the synthetic DNA sequence.

An embodiment of the disclosure is a method of hydrolysis of an organophosphate nerve agent comprising contacting an organophosphate nerve agent with the synthetic amino acid sequence of SEQ ID NO: 5; and hydrolyzing the organophosphate nerve agent. In an embodiment, the organophosphate is VX. In an embodiment, the organophosphate is VR. In another embodiment, the organophosphate is selected from the group consisting of GB, GD, and GF.

An embodiment of the disclosure is a system for detoxifying an organophosphate nerve agent comprising contacting the synthetic amino acid sequence of SEQ ID NO: 5 with an organophosphate nerve agent.

An embodiment of the disclosure is a kit for detoxifying an organophosphate nerve agent comprising the synthetic amino acid sequence of SEQ ID NO: 5.

An embodiment of the disclosure is a synthetic amino acid sequence comprising the synthetic amino acid sequence of L7ep-3a I106G (SEQ ID NO: 6), capable of hydrolyzing organophosphates. In an embodiment, a synthetic DNA sequence encodes the synthetic amino acid sequence of SEQ ID NO: 6; In another embodiment, a synthetic cDNA sequence comprising the coding sequence of the synthetic DNA sequence. In yet another embodiment, a plasmid comprising the synthetic DNA sequence.

An embodiment of the disclosure is a method of hydrolysis of an organophosphate nerve agent comprising contacting an organophosphate nerve agent with the synthetic amino acid sequence of SEQ ID NO: 6; and hydrolyzing the organophosphate nerve agent. In an embodiment, wherein the organophosphate is VX. In another embodiment, the organophosphate is VR. In yet another embodiment, the organophosphate is selected from the group consisting of GB, GD, and GF.

An embodiment of the disclosure is a system for detoxifying an organophosphate nerve agent comprising contacting the synthetic amino acid sequence of SEQ ID NO: 6 with an organophosphate nerve agent.

An embodiment of the disclosure is a kit for detoxifying an organophosphate nerve agent comprising the synthetic amino acid sequence of SEQ ID NO: 6.

An embodiment of the disclosure is a method of producing variants of phosphotriesterase, wherein the variants are capable of detoxifying an organophosphate nerve agent, comprising the steps of: obtaining a PTE gene; inserting the PTE gene into a vector; preparing a series of sequential mutational libraries wherein the PTE gene encodes a synthetic amino acid sequence of SEQ ID NO: 6; expressing the variant as a protein; screening the variant for catalytic activity against one selected from the group consisting of DEVX, DMVX, DEVR, and OMVR to determine the hydrolytic activity; and selecting the variant for use in hydrolysis of an organophosphate nerve agent based upon its hydrolytic activity. In an embodiment, the variant synthetic amino acid sequence is at least 80% homogenous to the synthetic amino acid sequence of SEQ ID NO: 6.

An embodiment of the disclosure is a method of producing variants of phosphotriesterase, wherein the variants are capable of detoxifying an organophosphate nerve agent, comprising the steps of: obtaining a PTE gene; inserting the PTE gene into a vector; preparing a series of sequential mutational libraries wherein the PTE gene encodes a synthetic amino acid sequence comprising the mutations I106C, F132V, H254Q, H257Y, A270V, L272M, I274N, and S308L (SEQ ID NO: 5); expressing the variant as a protein; screening the variant for catalytic activity against one selected from the group consisting of DEVX, DMVX, DEVR, and OMVR to determine the hydrolytic activity; and selecting the variant for use in hydrolysis of an organophosphate nerve agent based upon its hydrolytic activity. In an embodiment, the variant comprising the mutations I106C, F132V, H254Q, H257Y, A270V, L272M, I274N, and S308L synthetic amino acid sequence is at least 80% homogenous to the synthetic amino acid sequence of SEQ ID NO: 5)

The foregoing has outlined rather broadly the features of the present disclosure in order that the detailed description that follows can be better understood. Additional features and advantages of the disclosure will be described hereinafter, which form the subject of the claims.

BRIEF DESCRIPTION OF THE DRAWINGS

In order that the manner in which the above-recited and other enhancements and objects of the disclosure are obtained, a more particular description of the disclosure briefly described above will be rendered by reference to specific embodiments thereof which are illustrated in the appended drawings. Understanding that these drawings depict only typical embodiments of the disclosure and are therefore not to be considered limiting of its scope, the disclosure will be described with additional specificity and detail through the use of the accompanying drawings in which:

FIG. 1 depicts the hydrolysis of VX by phosphotriesterase to a nontoxic form;

FIG. 2A depicts the structure of ($S_P$)-tabun (GA);

FIG. 2B depicts the structure of ($S_P$)-sarin (GB);

FIG. 2C depicts the structure of ($S_PS_C$)-soman (GD);

FIG. 2D depicts the structure of ($S_PR_C$)-soman (GD);

FIG. 2E depicts the structure of paraoxon;

FIG. 2F depicts the structure of ($S_P$)-cyclosarin (GF);

FIG. 2G depicts the structure of ($S_P$)-VX;

FIG. 2H depicts the structure of ($S_P$)-VR;

FIG. 3A depicts the structure of VX;

FIG. 3B depicts the structure of VR;

FIG. 3C depicts the structure of Demeton-S;

FIG. 3D depicts the structure of Demeton-S methyl;

FIG. 3E depicts the structure of diisopropyl amiton (DEVX);

FIG. 3F depicts the structure of paraoxon;

FIG. 3G depicts the structure of $R_P$-1;

FIG. 3H depicts the structure of $S_P$-1;

FIG. 4A depicts the structure of $S_P$-1 (Compound 1);

FIG. 4B depicts the structure of $S_P$-2 (Compound 2);

FIG. 4C depicts the structure of $S_P$-3 (Compound 3);

FIG. 4D depicts the structure of $S_PS_C$-4 (Compound 4);

FIG. 4E depicts the structure of $S_PR_C$-4 (Compound 4);

FIG. 4F depicts the structure of $S_P$-5 (Compound 5);

FIG. 4G depicts the structure of $R_P$-1 (Compound 1);

FIG. 4H depicts the structure of $R_P$-2 (Compound 2);

FIG. 4I depicts the structure of $R_P$-3 (Compound 3);

FIG. 4J depicts the structure of $R_PR_C$-4 (Compound 4);

FIG. 4K depicts the structure of $R_PS_C$-4 (Compound 4);

FIG. 4L depicts the structure of $R_P$-5 (Compound 5);

FIG. 5A depicts representative time courses for the complete hydrolysis of 160 μM racemic VX by the QF variant of PTE;

FIG. 5B depicts representative time courses for the complete hydrolysis of 160 μM racemic VX by the WT variant of PTE;

FIG. 5C depicts representative time courses for the complete hydrolysis of 160 μM racemic VX by the VRN-VQFL variant of PTE;

FIG. 5D depicts representative time courses for the complete hydrolysis of 160 μM racemic VX by the L7ep-3a variant of PTE;

FIG. 5E depicts representative time courses for the complete hydrolysis of 160 μM racemic VX by the L7ep-2b variant of PTE;

FIG. 5F depicts representative time courses for the complete hydrolysis of 160 μM racemic VX by the QF+L7ep-2b variant of PTE;

FIG. 6 depicts enhancement in the catalytic properties for the hydrolysis of VX and DEVX by variants of PTE;

FIG. 7 depicts representative Michaelis-Menton plots for the hydrolysis of DEVX by wild-type and evolved variants of PTE;

FIG. 8 depicts the hydrolysis of racemic VX by the VRN-VQFL variant observed by quantitative $^{31}P\{^{1}H\}$ NMR spectroscopy;

FIG. 9 depicts construction of the multisite partially randomized PTE library;

FIG. 10 depicts the screening of the M317X mutant library against $S_P$-5 using GWT-d1 as the parental template.

FIG. 11A depicts screening of the six-site randomized library using GWT-f1 as the parental template with $S_P$-5;

FIG. 11B depicts screening of the error-prone PCR library using GWT-f4 as the parental template with $S_P$-5;

FIG. 12 depicts an outline of the parental linage for the construction of mutants of PTE that are enhanced for the hydrolysis of $S_P$-4 and $S_P$-5;

FIG. 13A depicts bar graphs illustrating enhanced values for $k_{cat}/K_m$ ($M^{-1}s^{-1}$) for the $S_P$-enantiomer of compound 1 (FIG. 4A);

FIG. 13B depicts bar graphs illustrating enhanced values for $k_{cat}/K_m$ ($M^{-1}s^{-1}$) for the $S_P$-enantiomer of compound 2 (FIG. 4B);

FIG. 13C depicts bar graphs illustrating enhanced values for $k_{cat}/K_m$ ($M^{-1}s^{-1}$) for the $S_P$-enantiomer of compound 3 (FIG. 4C);

FIG. 13D depicts bar graphs illustrating enhanced values for $k_{cat}/K_m$ ($M^{-1}s^{-1}$) for the $S_P$-enantiomer of compound $S_PR_C$-4 (compound 4) (FIG. 4E);

FIG. 13E depicts bar graphs illustrating enhanced values for $k_{cat}/K_m$ ($M^{-1}s^{-1}$) for the $S_P$-enantiomer of compound $S_PS_C$-4 (compound 4) (FIG. 4D);

FIG. 13F depicts bar graphs illustrating enhanced values for $k_{cat}/K_m$ ($M^{-1}s^{-1}$) for the $S_P$-enantiomer of compound 5 (FIG. 4F); and FIG. 14 depicts the amino acid sequence of organophosphate-degrading protein (opd) from *Brevundimonas diminuta* (*Pseudomonas diminuta*) (SEQ ID NO: 1).

FIG. 15A depicts the structure of paraoxon.

FIG. 15B depicts the structure of $S_p$-APVR.

FIG. 15C depicts the structure of $R_p$-APVR.

FIG. 15D depicts the structure of $S_p$-VX.

FIG. 15E depicts the structure of DEVX.

FIG. 15F depicts the structure of DMVX.

FIG. 15G depicts the structure of $S_p$-VR.

FIG. 15H depicts the structure of DEVR.

FIG. 15I depicts the structure of $R_p$-OMVR.

FIG. 16A depicts a structural alignment between wild-type PTE (white) and L7ep-3a mutant (blue).

FIG. 16B depicts an expanded view of Loop-7 and -8.

FIG. 17 depicts the substrate binding pockets of wild-type (white) and L7ep-3a (grey).

FIG. 18 depicts the metal center of wild-type PTE (A), QF (B), and L7ep-3a (C) variants.

FIG. 19A depicts $S_P$-VX docked in thee active site of L7ep-3a.

FIG. 19B depicts $S_P$-VR docked into the active site of L7ep-3a I106G.

DETAILED DESCRIPTION

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings making apparent to those skilled in the art how the several forms of the disclosure can be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary 3rd Edition.

As used herein the term, "wild-type" means and refers to the non-mutated version of a gene as it appears in nature.

As used herein the term, "enantiomer" means and refers to either of a pair of chemical compounds that have molecular structures that are nonsuperimposable mirror images.

As used herein the term, "G-agent" or "G-type" means and refers to nerve agents of the G (German) series. The series includes but is not limited to GA (tabun), GB (sarin), GF (cyclosarin) and GD (soman).

As used herein the term, "V-type" means and refers to nerve agents of the V series. The series includes but is not limited to VX, VE, V-gas, VG, VR, and VM.

Tables

Table 1. Mutations present in additional variants identified

Figure 4:
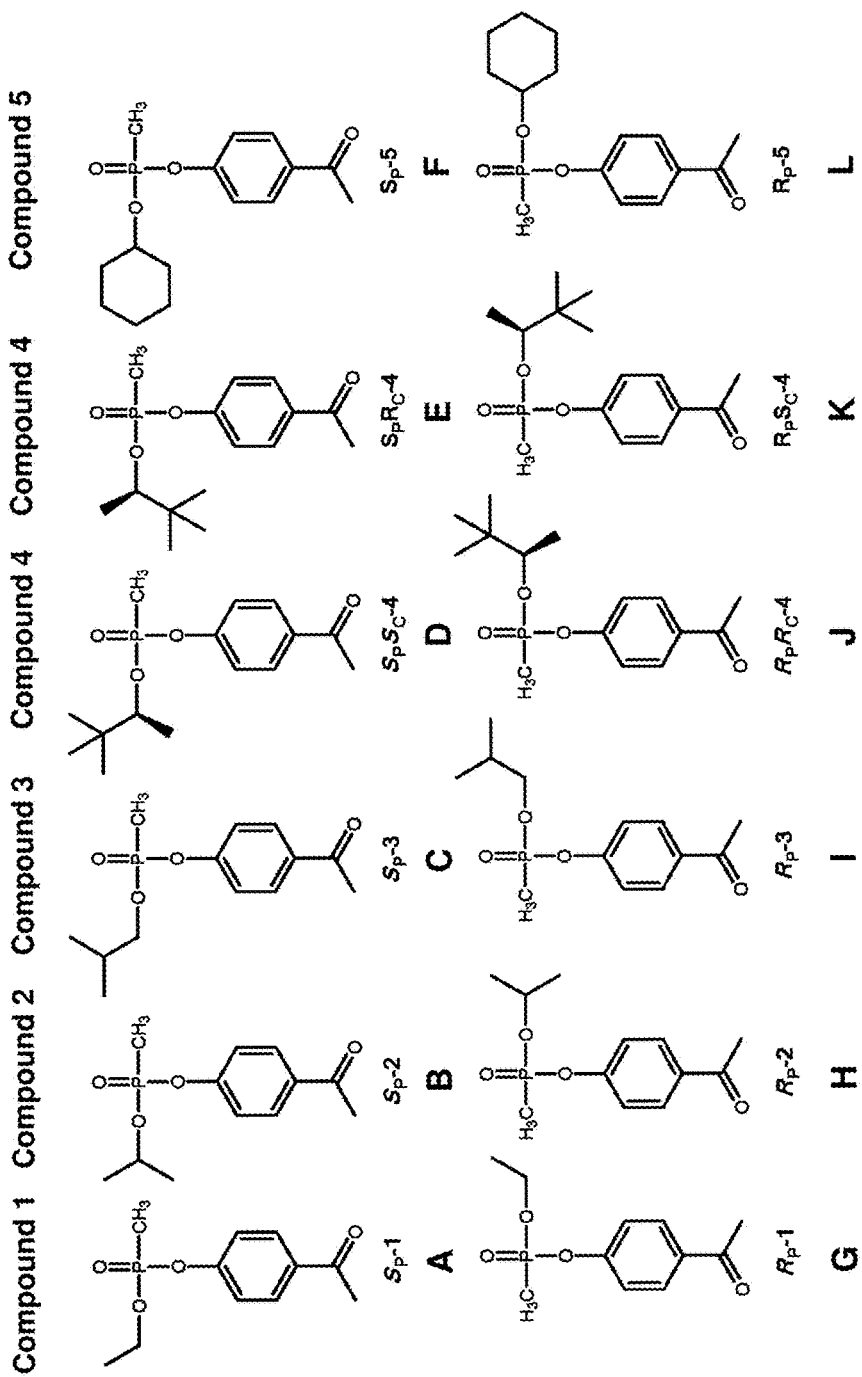

Table 2. Activity of PTE Variants against VX Analogues DEVX and Compound 1 ($R_P$-1 and $S_P$-1) (see FIGS. 4A and 4G for structures)

Table 3. Activity of additional PTE Variants with DEVX

Table 4. Kinetic Parameters for PTE Variants with Paraoxon and Demeton-S

Table 5. Activity of PTE Variants with Racemic VX

Table 6. Identification of Mutants

Table 7. Activity of Wild-Type and Mutant Enzymes with Racemic G-Agents

Table 8. Kinetic Constants for Hydrolysis of GB, GD, and GF

Table 9. Values of $k_{cat}$ ($s^{-1}$) for Wild-Type PTE and its Mutants

Table 10. Values of $k_{cat}/K_m$ ($M^{-1}$ $s^{-1}$) for Wild-Type PTE and its Mutants Table 11. Kinetic constants for PTE variants with APVR.

Table 12. Kinetic parameters for PTE variants with paraoxon and DEVX.

Table 13. Kinetic constants with the racemic nerve agents VX and VR.

Table 14. X-ray crystallography data for L7ep-3a and L7-ep-3a I106G.

Table 15. Kinetic constants for PTE variants with V-agent analogs.

The V-type organophosphorus nerve agents are among the most hazardous compounds known. Previous efforts to evolve the bacterial enzyme phosphotriesterase (PTE) for the hydrolytic decontamination of VX resulted in the variant L7ep-3a, which has a $k_{cat}$ value more than 2-orders of magnitude higher than wild-type PTE. Because of the relatively small size of the O-ethyl, methylphosphonate center in VX, stereoselectivity is not a major concern. However, the Russian V-agent, VR, contains a larger 0-isobutyl, methylphosphonate center making stereoselectivity a significant issue since the $S_P$-enantiomer is more toxic than the $R_P$-enantiomer. The three-dimensional structure of the L7ep-3a variant was determined to a resolution of 2.01 Å (PDB id: 4ZST). The active site of the L7ep-3a mutant has revealed a network of hydrogen bonding interactions between Asp-301, Tyr-257, Gln-254 and the hydroxide that bridges the two metal ions. A series of new analogs that mimic VX and VR has helped to identify critical structural features for the development of new enzyme variants that are further optimized for the catalytic detoxification of VR and VX. The best of these mutants has been shown to hydrolyze the more toxic $S_P$-enantiomer of VR more than 600-fold faster than the wild-type phosphotriesterase. The organophosphorus nerve agents are among the most toxic compounds known. Compounds such as sarin, soman and VX are all chiral methyl phosphonates where the toxicity of the SP-enantiomer is much greater than for the RP-enantiomer. (33) Recent events have dramatically demonstrated the continuing importance of developing rapid and environmentally compatible methods for the decontamination of these compounds.(34) This situation is particularly true for the V-type nerve agents, where the lethal dose is approximately 6 mg/person, and these compounds have been shown to persist for long periods of time.(35, 36) Significant advances have been made in developing enzymatic methods of decontamination for the G-type and VX nerve agents using the bacterial enzyme phosphotriesterase (PTE).(37, 38) While wild-type PTE has reasonable activity against the G-type nerve agents (kcat/Km~105 M−1 s−1), this enzyme preferentially hydrolyzes the less toxic $R_P$-enantiomers.(39) Directed evolution of PTE to specifically target the G-type nerve agents has led to the identification of the variant H257Y/L303T (YT), which has proven highly efficient at the hydrolysis of the more toxic $S_P$-enantiomer of sarin (GB), soman (GD), and cyclosarin (GF) with values of $k_{cat}/K_m$ that exceed 106 $M^{-1}$ $s^{-1}$.(38)

Wild-type PTE exhibits little stereoselectivity against the relatively small phosphonate center of VX, but the elevated $pK_a$ of the thiol-leaving group provides a significant challenge for enzyme-catalyzed hydrolysis ($k_{cat}/K_m$~102 $M^{-1}$ $s^{-1}$).(37) Mutation of residues contained within the active site of PTE resulted in the isolation of the variant H245Q/H257F (QF), which exhibited a 100-fold improvement for the hydrolysis of VX, relative to the wild-type enzyme (see Table 1 for identity of variants).(37) Additional active site variations resulted in the identification of the mutant CVQFL (QF+I106C/F132V/S308L) with a similar catalytic efficiency for the hydrolysis of VX, but a three-fold improvement in $k_{cat}$. The best variant identified to date for the hydrolysis of VX is VRN-VQFL (QF+F132V/S308L+ A80V/K185R/I274N). This mutant combines expression-enhancing mutations (A80V/K185R/I274N) with additional changes in the active site to achieve a $k_{cat}/K_m$ of $7 \times 10^4$ $M^{-1}$ $s^{-1}$ for the hydrolysis of the $S_P$-enantiomer of VX. (37, 40, 41) Expansion of the mutation strategy to targeted error-prone PCR, led to the identification of the variant L7ep3a (CVQFL+H257Y/A270V/L272M/I274N), which has a $k_{cat}$ value enhanced 152-fold relative to wild-type PTE.(37) How these combined mutations, some of which do not fall in the active site, are able to bring about such a dramatic improvement in catalytic ability is not clear.

In addition to VX, the V-agents include the Russian (VR) and Chinese versions. Exemplified by VR, these additional V-agents contain a smaller thiol leaving group, and a larger ester group attached to the phosphorus center (FIGS. 15A-15I). Wild-type PTE has enzymatic activity for the hydrolysis of racemic VR similar to VX, but the larger isobutyl group attached to the phosphorus center results in a 25-fold preference for the less toxic $R_P$-enantiomer.(39, 42) The catalytic activity of wild-type PTE for the hydrolysis of the more toxic $S_P$-enantiomer of VR ($k_{cat}/K_m$=4.3 M−1 s−1) is significantly lower than for the hydrolysis of VX. PTE variants which contain many of the same mutations as the VX-enhanced variants have been reported to have substantially improved catalytic activity against $S_P$-VR.(43) Currently, there is a lack of three-dimensional structural data that can be used to explain how the existing set of mutants are able to enhance the rate of hydrolysis of the phosphorothiolate bond in VX.

PTE variants can be used to decontaminate areas, equipment, and personnel after they come in contact with V-type or G-type nerve agents. This is especially useful for military or homeland security applications. The decontamination occurs without exposing the area, equipment, or personnel to harsh chemicals. Mutations in the sequence of PTE have been made to increase the ability of PTE to hydrolyze, and thus decontaminate, an area, equipment, or personnel. PTE was subjected to directed evolution for the improvement of catalytic activity against selected compounds through the manipulation of active site residues. A series of sequential two-site mutational libraries encompassing twelve active site residues of PTE was created. The libraries were screened for catalytic activity against a new VX analogue (DEVX), which contains the same thiolate leaving group of VX coupled to a di-ethoxy phosphate core rather than the ethoxy, methylphosphonate core of VX. The catalytic activity with DEVX was enhanced 26-fold relative to wild-type PTE. Further improvements were facilitated by targeted error-prone PCR mutagenesis of Loop-7 and additional PTE variants were identified with up to a 78-fold increase in the rate of DEVX hydrolysis. The best mutant hydrolyzed the racemic nerve agent VX with a value of $k_{cat}/K_m$ of $7\times10^4$ $M^{-1}$ $s^{-1}$; a 230-fold improvement relative to the wild-type PTE. The sequence of wild-type PTE (organophosphate-degrading protein (opd)), without the leader peptide residues (1-29), is found in FIG. 14. The highest turnover number achieved by the mutants tested was 137 $s^{-1}$; an enhancement of 152-fold relative to wild-type PTE. The stereoselectivity for the hydrolysis of the two enantiomers of VX was relatively low.

The P—S bond in VX is chemically more stable than the P—F bond found in the G-agents.(20) (FIGS. 2G, 2A-2D) Demeton-S contains the requisite P—S bond but does not contain the tertiary amine of VX, which is likely to be protonated at the relevant pH values. (FIGS. 3C, 3A) DEVX, containing the authentic leaving group of VX, yields results more directly applicable to the hydrolysis of VX itself. (FIGS. 3E, 3A)

The QF variant of PTE shows improved hydrolysis against the SP-enantiomer of a chiral VX analogue.(18) Table 1 lists the amino acid changes present in the variants. This mutant was found to be significantly better for the hydrolysis of the P—S bond in DEVX and demeton-S than wild-type PTE. The synergistic mutations in this variant suggested that further improvements in catalytic activity could be facilitated by simultaneously mutating pairs of residues in the active site. The initial mutant libraries targeted pairs of residues in the active site that modulated the size and shape of the three substrate binding pockets. Sequential optimization of the active site residues resulted in an 18-fold improvement in catalytic activity against DEVX. Combining the best variant (VQFL) with expression enhancing mutations resulted in the variant VRN-VQFL. The VRN-VQFL variant exhibited a 26-fold improvement for the hydrolysis of DEVX.

TABLE 1

Mutations present in additional variants identified.

| Variant | Mutations present |
| --- | --- |
| WT | Wild type |
| ARN | A80V/K185R/I274N |
| QF | H254Q/H257F |
| QF.1 | H254Q/H257F/F306W/Y309H |
| LQF | F132L/H254Q/H257F |
| VQF | F132V/H254Q/H257F |
| QF.a | W131H/F132L/H254Q/H257F |
| QF.b | W131H/F132I/H254Q/H257F |
| LQF.1 | F132L/H254Q/H257L |
| LQF.2 | F132L/H254R/H257A |
| LQF.3 | F132L/H254R/H257L |
| LQF.4 | F132L/H254R/H257Y |
| LQF.a | F132L/H254Q/H257F/L271V |
| LQF.b | F132L/H254Q/H257F/L271M |
| LQF.c | F132L/H254Q/H257F/L271A |
| LQFL | F132L/H254Q/H257F/S308L |
| LQF.d | F132L/H254Q/H257F/L271R/S308N |
| VQFL | F132V/H254Q/H257F/S308L |
| CVQFL | I106C/F132V/H254Q/H257F/S308L |
| VQFL.1 | I106G/F132V/H254Q/H257F/S308L |
| VQFL.2 | I106S/F132V/H254Q/H257F/S308L |
| VQFL.3 | I106A/F132V/H254Q/H257F/L303T/S308L |
| VRN-VQFL | A80V/F132V/K185R/H254Q/H257F/I274N/S308L |
| VRNGS-VQFL | A80V/F132V/K185R/D208G/H254Q/H257F/I274N/S308L/R319S |
| L7ep-1 | F132V/H254S/H257W/A266T/L271P/S308L |
| L7ep-2 | I106C/F132V/H254R/H257F/N265D/A270D/L272M/S276T/S308L |
| L7ep-3 | I106C/F132V/H254Q/H257Y/A270V/L272M/S308L |
| L7ep-4 | I106C/F132V/H254Q/H257F/I260N/D264N/I274N/S308L |
| L7ep-5 | I106C/F132V/H254Q/H257Y/E264G/S308L |
| L7ep-6 | I106C/F132V/H254Q/H257F/A266E/S269T/S308L |
| L7ep-7 | I106C/F132V/H254Q/H257F/I260V/S269T/S308L |
| L7ep-8 | I106C/F132V/H254Q/H257Y/I260V/S308L |
| L7ep-9 | I106C/F132V/H254Q/H257F/S269T/I274T/S308L |
| L7ep-10 | I106C/F132V/H254Q/H257Y/E263K/S308L |
| L7ep-11 | I106C/F132V/H254Q/H257Y/A266R/S308L |
| L7ep-12 | I106C/F132V/H254Q/H257F/S269T/I274S/S308L |
| L7ep-2a | I106C/F132V/H254R/H257F/N265D/A270D/L272M/I274T/S276T/S308L |
| L7ep-2b | I106C/F132V/H254R/H257F/N265D/A270D/I274N/S276T/S308L |
| L7ep-2c | I106C/F132V/H254Q/H257F/N265D/A270D/L272M/S276T/S308L |
| L7ep-2d | I106C/F132V/H254R/H257F/N265D/A270D/L272M/I274S/S276T/S308L |
| L7ep-2e | I106C/F132V/H254R/H257F/N265D/A270D/I274P/S276T/S308L |
| L7ep-2f | I106C/F132V/H254R/H257F/N265D/A270D/I274S/S276T/S308L |
| L7ep-2g | I106C/F132V/H254R/H257F/N265D/A270D/I274Q/S276T/S308L |

TABLE 1-continued

Mutations present in additional variants identified.

| Variant | Mutations present |
|---|---|
| L7ep-2h | I106C/F132V/H254R/H257F/N265D/A270D/L272M/S276H/S308L |
| L7ep-2i | I106C/F132V/H254R/H257F/N265D/A270D/L272M/S276S/S308L |
| L7ep-2j | I106C/F132V/H254R/H257F/N265D/A270D/L272M/S276P/S308L |
| L7ep-3a | I106C/F132V/H254Q/H257Y/A270V/L272M/I274N/S308L |
| L7ep-3b | I106C/F132V/H254Q/H257Y/A270D/L272M/S308L |
| L7ep-3c | I106C/F132V/H254Q/H257Y/N265D/L272M/S308L |
| L7ep-3d | I106C/F132V/H254Q/H257Y/A270V/L272M/I274T/S308L |

Additional strategies were used to further enhance the activity of PTE against the phosphorothiolate bond. Error-prone PCR is a useful technique for enzyme evolution, but the mutation frequencies are typically restricted to 1-3 base pair changes per gene because of the significant chance of introducing deleterious mutations. Substantial improvements in enzyme activity can require numerous amino acid changes, which are not typically achievable by error-prone PCR. Targeting error-prone PCR to only Loop-7 (residues 253-276) resulted in a mutation library with an average of 6 mutations per gene but still retained>20% active colonies. The hydrolysis of DEVX for one of the variants (L7ep-3) was improved to 36-fold over wild-type PTE due to 3 additional amino acid changes. The best variant identified (L7ep-2) was improved 63-fold for the hydrolysis of DEVX by 5 additional amino acid changes. Further optimization of L7ep-2 and L7ep-3 resulted in additional mutations that improved the activity to 78-fold (L7ep-2a) and 71-fold (L7ep-3a) over wild-type PTE, and achieved turnover numbers for the hydrolysis of the phosphorothiolate bond in excess of 100 $s^{-1}$.

Figure 6:
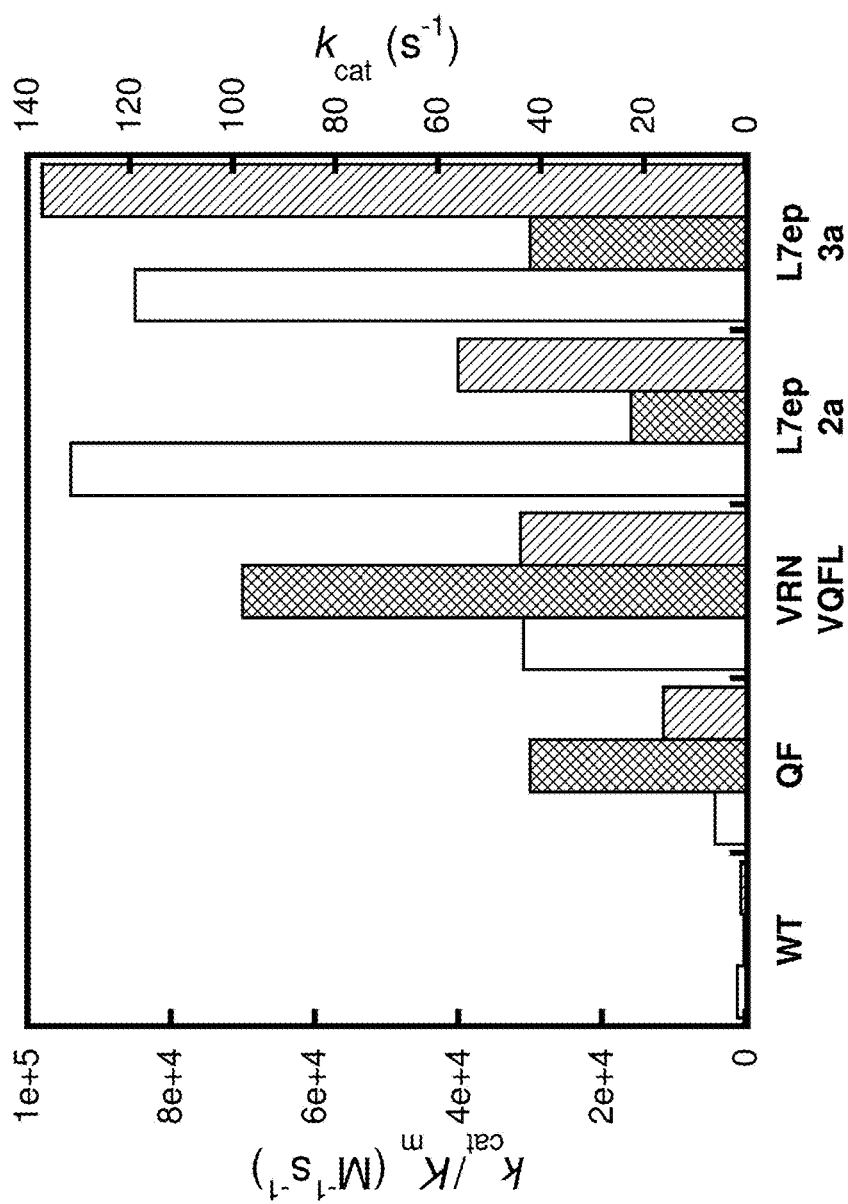

Hydrolysis of VX. A full kinetic characterization of wild-type and improved variants of PTE using racemic VX was conducted. Wild-type PTE exhibited low activity against VX, but there was a dramatic improvement with the QF mutant. The mutations in the large group pocket resulted in substantial improvements in $k_{cat}$. The best variant identified (VRN-VQFL) against VX combines active site mutations in all three pockets and has a $k_{cat}/K_m$ value that is increased 235-fold over wild-type PTE (FIG. 6). FIG. 6 depicts enhancement in the catalytic properties for the hydrolysis of VX and DEVX by variants of PTE. The values of $k_{cat}/K_m$ for evolved variants of PTE are presented for DEVX (open bars) and VX (cross-hatched bars). The $k_{cat}$ values for the hydrolysis of VX are shown as right-hatched bars. (FIG. 6).

The Loop-7 optimized variants show good activity against VX, but did not demonstrate improved activity relative to the VRN-VQFL variant. The changes to Loop-7 resulted in substantial improvements in $k_{cat}$ but little change in the catalytic efficiency.

The L7ep-3a variant has a $k_{cat}$ of 137 $s^{-1}$ for the hydrolysis of VX. This value is the highest ever reported for the enzymatic hydrolysis of VX.(11,14,24,25) Single concentration experiments with the H254R/H257L mutant of PTE showed an improvement of 10-fold against racemic VX.(24) Another variant exhibited a 26-fold improvement over wild-type PTE at 0.5 mM VX.(25) By contrast, the VRN-VQFL and L7ep-3 variants are improved by more than 200-fold in the value of $k_{cat}/K_m$. Human PON1 (paraoxonase) has been evolved in the laboratory for the hydrolysis of VX, but the reported value of $k_{cat}/K_m$ for the best variant is $2.5 \times 10^3$ $M^{-1}$ $s^{-1}$, whereas the best PTE variant (VRN-VQFL) identified in this investigation has a value of $k_{cat}/K_m$ of $7 \times 10^4$ $M^{-1}$ $s^{-1}$.(11)

Figure 8:
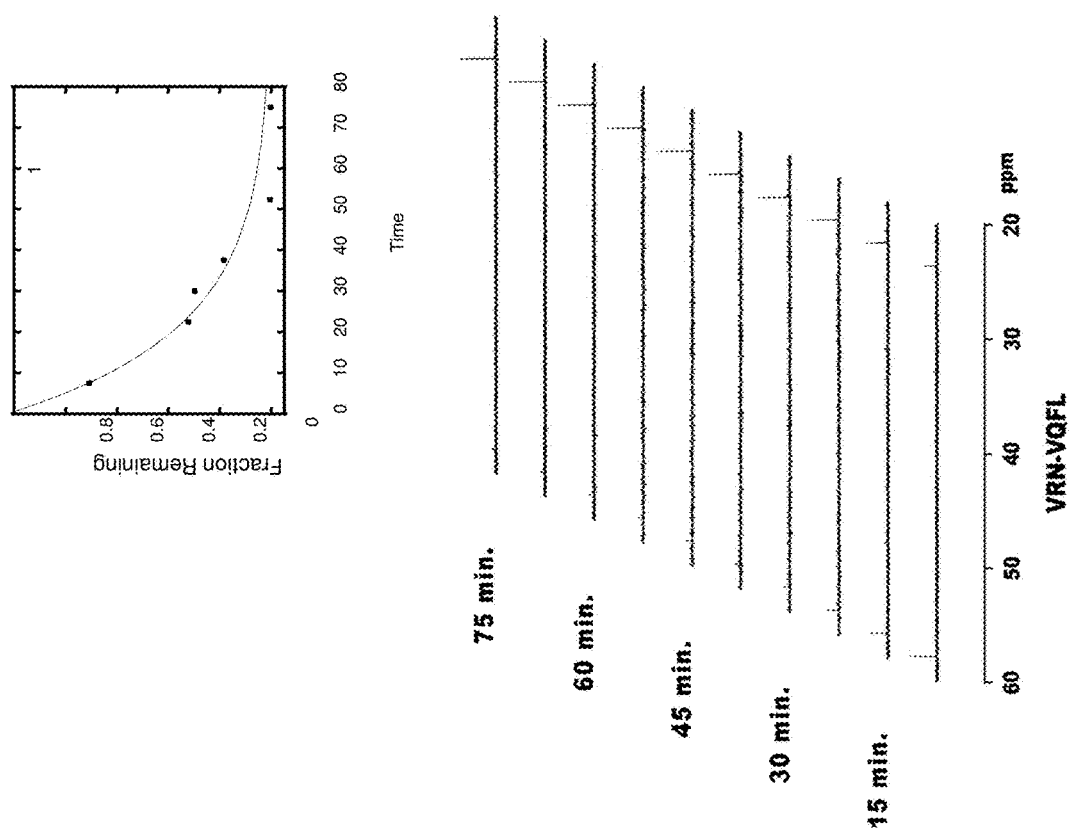

Stereochemical Preferences of Active Site Mutants. The toxicity of the organophosphate nerve agents depends on the stereochemistry of the phosphorus center.(17) With VX, it is estimated that the $S_P$-enantiomer is about 100-fold more toxic than the $R_P$-enantiomer. The QF mutant prefers to hydrolyze the more toxic $S_P$-enantiomer of VX by a factor of 12, relative to the $R_P$-enantiomer, whereas the L7ep-2b mutant prefers to hydrolyze the $R_P$-enantiomer by a factor of 12. The stereochemical preferences for the hydrolysis of VX are fully consistent with the stereoselective properties of these two mutants for the hydrolysis of $S_P$-1 and $R_P$-1, suggesting that the variants VRN-VQFL, L7ep-3, and L7ep-3a also prefer the $S_P$-enantiomer of VX. While the modest selectivity prevented definitive assignment of the preferred enantiomer, complete neutralization of VX by the VRN-VQFL mutant via the hydrolysis of both enantiomers was demonstrated by $31^P$-NMR spectroscopy (FIG. 8).

The reconstruction of PTE for the hydrolysis of VX has resulted in dramatic improvements in the values of $k_{cat}$ and $k_{cat}/K_m$, relative to the wild type enzyme. It is proposed that the increase in the catalytic constants has been achieved by an increase in the rate constant for cleavage of the P—S bond ($k_3$) rather than changes in the formation of the ternary complex ($k_1$, $k_2$) or the rate constant for product release ($k_5$) as illustrated in a minimal kinetic mechanism (Scheme 1). The thiol leaving group of VX has a higher $pK_a$ than the fluoride leaving group of the G-agents, and the p-nitrophenol group of paraoxon. It has been demonstrated with the wild-type PTE that the chemical step ($k_3$) is rate limiting for substrates with leaving groups having $pK_a$ values higher than 8.(20) Disruption of the hydrogen bonded network from D301-H254-D233 reduced the rate of hydrolysis of substrates with leaving groups having low $pK_a$ values but increased the rate of hydrolysis of substrates with leaving groups of higher $pK_a$ values.(30) Introduction of a glutamine at residue position 254 (as in the initial QF mutant), which apparently cannot support the transport of a proton away from the active site, may now facilitate the protonation of the thiol group by Asp-301 as the phosphorothiolate bond is cleaved.

Scheme 1

$$E \underset{}{\overset{k_1 A}{\rightleftharpoons}} EA \xrightarrow{k_3} EPQ \xrightarrow{k_5} E + P + Q$$

The turnover numbers for some slow substrates of PTE are thought to be reflective of the ability of the enzyme to align the substrate with the nucleophilic hydroxyl group attached to the binuclear metal center.(13) There is a strong likelihood that for some of the variants, subtle changes in the conformation of the active site will facilitate a better alignment between the substrate and attacking hydroxide, thereby achieving higher enzymatic rates of hydrolysis. In particular, the Loop-7 variants have been modified at residues that are somewhat distant from the active site, but are expected to bring about changes in the positioning of the Loop-7 α-helix.(13,28) This alignment effect would, of course, differ between the di-ethoxy phosphorus center of DEVX and the methylphosphonate core of VX (FIGS. 3E, 3A), which may explain the differences in the $k_{cat}$ values for DEVX and VX with the variants L7ep-2a and L7ep-3a. (Table 2) These changes have resulted in variants with high enzymatic efficiency and exceptional kinetic constant for the hydrolysis of VX.

the positions of interest. The 271X/308X library was constructed by sequential reactions. The 106X/303X and 60X/317X libraries were constructed using a PCR overlap extension technique.(26) Plasmids from at least 10 colonies of

TABLE 2

Activity of PTE Variants against VX analogues DEVX and compound 1
(see FIGS. 3, 4A and 4G for structures)*

| Variant | DEVX | | | $R_P$-1 | | | $S_P$-1 | | |
|---|---|---|---|---|---|---|---|---|---|
| | $k_{cat}$ | $K_m$ | $k_{cat}/K_m$ | $k_{cat}$ | $K_m$ | $k_{cat}/K_m$ | $k_{cat}$ | $K_m$ | $k_{cat}/K_m$ |
| WT | 1.1 | 0.87 | $1.2 \times 10^3$ | 100 | 3700 | $2.7 \times 10^4$ | 92 | 320 | $2.9 \times 10^5$ |
| QF | 6.1 | 1.4 | $4.2 \times 10^3$ | 120 | 230 | $5.3 \times 10^5$ | 34 | 18 | $1.8 \times 10^6$ |
| LQF | 15 | 1.7 | $9.0 \times 10^3$ | 112 | 910 | $1.2 \times 10^5$ | 27 | 13 | $2.1 \times 10^6$ |
| VQF | 18 | 1.0 | $1.9 \times 10^4$ | 82 | 340 | $2.4 \times 10^5$ | 25 | 11 | $2.2 \times 10^6$ |
| LQFL | 10 | 0.76 | $1.4 \times 10^4$ | 76 | 160 | $4.7 \times 10^5$ | 45 | 7.4 | $6.1 \times 10^6$ |
| VQFL | 14 | 0.65 | $2.2 \times 10^4$ | 69 | 129 | $5.3 \times 10^5$ | 32 | 7.4 | $4.3 \times 10^6$ |
| CVQFL | 16 | 0.76 | $2.1 \times 10^4$ | 54 | 170 | $3.2 \times 10^5$ | 39 | 24 | $1.6 \times 10^6$ |
| VRN-VQFL | 22 | 0.73 | $3.1 \times 10^4$ | 124 | 160 | $7.8 \times 10^5$ | 65 | 26 | $2.5 \times 10^6$ |
| VRNGS-VQFL | 11 | 0.99 | $1.1 \times 10^4$ | 204 | 350 | $5.8 \times 10^5$ | 93 | 22 | $4.3 \times 10^6$ |
| L7ep-1 | 16 | 0.60 | $3.2 \times 10^4$ | 590 | 8600 | $6.8 \times 10^5$ | 670 | 2800 | $2.3 \times 10^5$ |
| L7ep-2 | 48 | 0.63 | $7.6 \times 10^4$ | 240 | 730 | $3.3 \times 10^5$ | 90 | 400 | $2.3 \times 10^5$ |
| L7ep-3 | 29 | 0.69 | $4.3 \times 10^4$ | 143 | 560 | $2.5 \times 10^5$ | 50 | 22 | $2.3 \times 10^6$ |
| L7ep-2a | 135 | 1.4 | $9.4 \times 10^4$ | 235 | 950 | $2.5 \times 10^5$ | 180 | 1090 | $1.7 \times 10^5$ |
| L7ep-2b | 76 | 1.0 | $7.4 \times 10^4$ | 136 | 610 | $2.2 \times 10^5$ | 95 | 1090 | $8.6 \times 10^4$ |
| L7ep-3a | 51 | 0.6 | $8.5 \times 10^4$ | 290 | 1500 | $1.9 \times 10^5$ | 90 | 36 | $2.5 \times 10^6$ |
| L7ep-36 | 64 | 1.0 | $6.2 \times 10^4$ | 202 | 1800 | $1.1 \times 10^5$ | 48 | 34 | $1.4 \times 10^6$ |

*Standard errors from fits of the data to eq 1 are less than 20% of the stated values.

The structure of the L7ep3a variant was determined. The structure aided in understanding the chemical mechanism for the enhancement of phosphorothiolate bond cleavage. With this new structural information, a series of PTE variants was created to incorporate changes in the active site of PTE that would more easily accommodate the O-isobutyl group of VR. To facilitate the further development of PTE for the hydrolysis of various V-agents, a new series of analogs were designed and synthesized. Enhanced variants of PTE have been identified that have more than a 600-fold improvement in the catalytic activity for the hydrolysis of the toxic SP-enantiomer of VR.

EXAMPLES

Example 1

Most chemicals can be obtained from Sigma Chemical Company. The pfuTurbo DNA polymerase can be obtained from Agilent Technologies and the various restriction enzymes can be acquired from New England Biolabs. The two enantiomers of compound 1 (FIGS. 4A and 4G) can be synthesized.(18) VX samples can be Chemical Agent Standard Analytical Reference Material (CASARM).

Example 2

Active Site Library Construction. The nucleotides in the gene for PTE were modified to replace the nucleotides encoding the leader peptide (amino acid residues 1-29) with nucleotides encoding a methionine. (FIG. 14) Nucleotides encoding amino acid residues 29-365 of PTE were inserted into a pET 20b+ vector between the NdeI and EcoRI restriction sites as previously described.(18) The amino acid residue numbering of the sequence including the leader sequence has been retained. The 306X/309X, 131X/132X and 254X/257X double substitution libraries were constructed by site-directed mutagenesis using single sets of primers containing NNS (N=any base, S=G or C) codons at each library were sequenced to ensure the randomization at the positions of interest. The identities of specific mutations for the variants are given in Table 1. The name of the phosphotriesterase gene is opd, the GenBank Accession Number is AER10490.1, and the Protein Model Portal Accession Number is G8DNV8.

Example 3

Construction of Targeted Error-Prone Library. To construct the Loop-7 error-prone library, a set of 30-bp primers corresponding to the DNA sequences upstream and downstream of Loop-7 (amino acid residues 253-276) were used to amplify the PTE gene in three fragments. The amino acid residue numbering of the sequence including the leader sequence has been retained. The DNA coding region of Loop-7 was amplified in an error-prone PCR reaction while the two remaining fragments were amplified using standard PCR techniques. The final gene was constructed using PCR overlap-extension, resulting in a gene library with errors only in the coding region for residues 253-276.

Example 4

Optimization of Error-Prone Variants. The five residue positions (254, 265, 270, 272, and 276) identified in the best Loop-7 error prone variant and residues 257 and 274 were further optimized by construction of two two-site (254X/257X and 272X/274X) and three single-site libraries (265X, 270X, 276X). The amino acid residue numbering of the sequence including the leader sequence has been retained. Libraries were constructed via QuikChange mutagenesis using degenerate primers to allow all 20 amino acids at the positions of interest. Approximately 200 colonies from each single-site library were screened, and approximately 1200 colonies from each two-site library were screened. The two enhanced variants identified in the Loop-7 error prone library were used as the template for a second round of targeted error-prone PCR of Loop-7.

Example 5

Library Screening. Plasmid libraries were transformed into BL21 (DE3) *E. coli* competent cells and grown on LB plates. For all library transformations, the amount of DNA was kept low (<10 ng) to avoid the potential complication of double transformants.(27) Single colonies were used to inoculate 0.75 mL cultures of Super Broth (32 g tryptone, 20 g yeast extract, 5 g NaCl, and 0.4 g NaOH in 1 L $H_2O$) supplemented with 0.5 mM $CoCl_2$ in a 96-well block format. Cultures were grown at 37° C. for 8 hours. The temperature was reduced to 30° C. and protein expression induced by addition of 1 mM IPTG. Following 16 hours of additional growth, the bacteria were harvested by diluting a portion of the culture in a 1:1 ratio with 50 mM HEPES pH 8.0, 100 µM $CoCl_2$, 10% BugBuster® 10× (EMD Chemicals). Cultures were tested for activity against DEVX using a standard 250 µL assay that consisted of 50 mM HEPES, pH 8.0, 100 µM $CoCl_2$, 0.3 mM 5,5'-dithiobis(2-nitro-benzoic acid) (DTNB) and 0.2-0.5 mM DEVX. The reactions were initiated by the addition of 10 µL of cell lysate. Reactions proceeded at room temperature until color was clearly visible (1-4 hours). Product formation was determined by the change in absorbance at 412 nm using a plate reader. The variant used as the starting template for each library was included as a control on each plate. To account for differential culture growth, the final change in absorbance was normalized using the $OD_{600}$ for each culture compared to the average $OD_{600}$ of controls. The colonies giving the best results were re-grown as 5 mL overnight cultures and the plasmids harvested and sequenced to identify the variants.

Example 6

Figure 7:
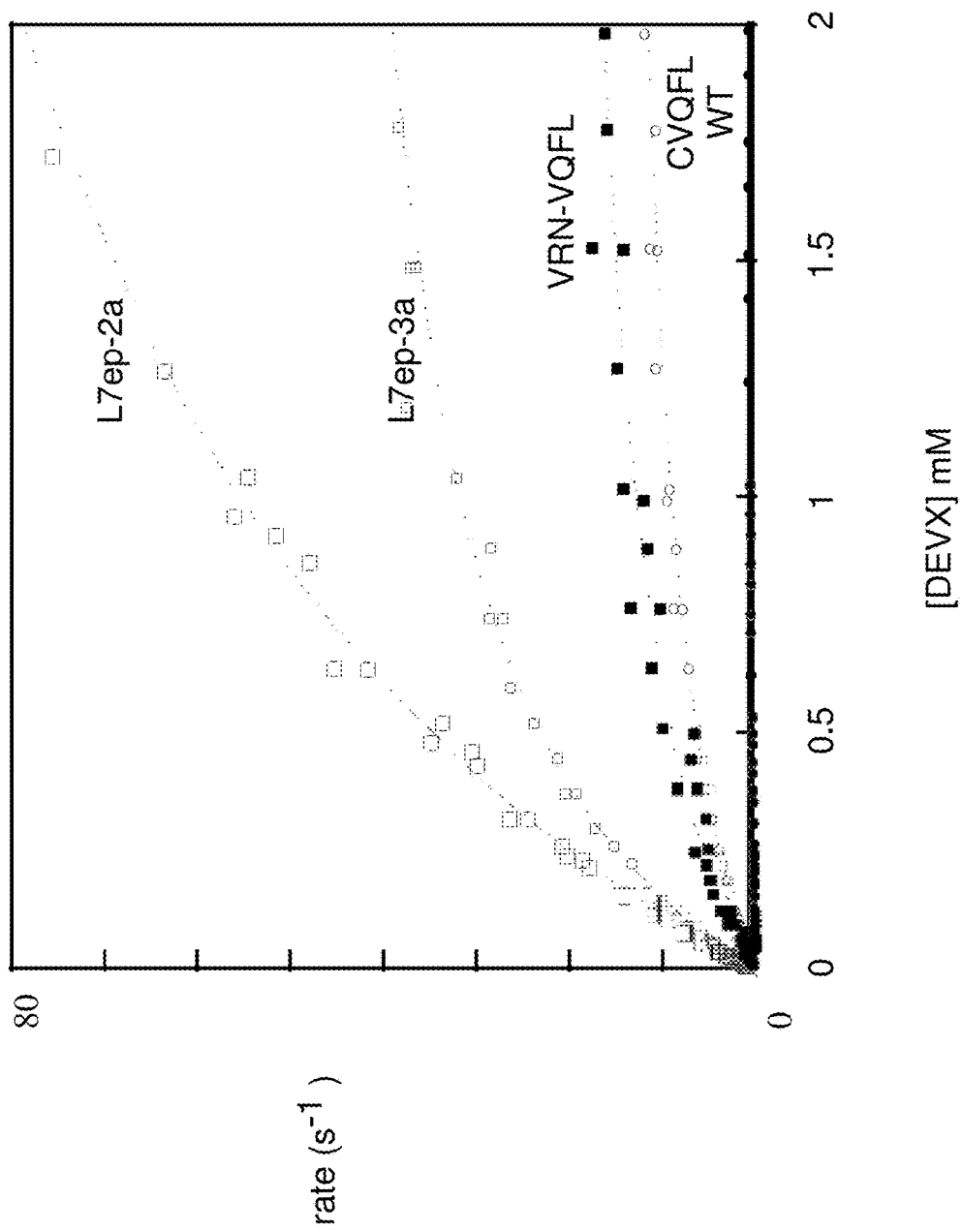

Kinetic Measurements. All assays with DEVX, paraoxon, $S_P$-1, $R_P$-1, and demeton-S were 250 µL in total volume and followed for 15 minutes in a 96-well plate reader at 30° C. Assays with VX were conducted in a volume of 500 µL in 1 mL cuvettes. DEVX, demeton-S, and VX assays monitored the release of the product thiol at 412 nm ($\Delta\varepsilon_{412}$=14,150 $M^{-1}$ $cm^{-1}$) by the inclusion of DTNB in the reaction mixture (50 mM HEPES, pH 8.0, 100 µM $CoCl_2$, and 0.3 mM DTNB). Assays with paraoxon and compound 1 (FIGS. 4A and 4G) were conducted in 50 mM CHES, pH 9.0, and 100 µM $CoCl_2$. Assays of compound 1 (FIGS. 4A and 4G) contained 10% methanol. Paraoxon hydrolysis was followed by the release of p-nitrophenol at 400 nm ($\Delta\varepsilon_{400}$=17,000 $M^{-1}$ $s^{-1}$) and the hydrolysis of compound 1 (FIGS. 4A and 4G) was followed at 294 nm ($\Delta\varepsilon_{294}$=7,710 $M^{-1}$ $cm^{-1}$). Reactions were initiated by the addition of enzyme. The data were fit to equation 1 to obtain values of $K_m$, $k_{cat}$, and $k_{cat}/K_m$. A representative data set is provided in FIG. 7. FIG. 7 depicts representative Michaelis-Menton plots for the hydrolysis of DEVX by wild-type and evolved variants of PTE. Reaction conditions were 50 mM Hepes (pH 8), 100 µM $CoCl_2$, 0.3 mM DTNB in a total volume of 250 µL at 30° C. (FIG. 7). Reactions were initiated by addition of appropriately diluted enzyme. Enzyme concentrations in the reactions were; wild-type=54 nM, CVQFL=5.0 nM, VRN-VQFL=6.29 nM, L7ep-3a=1.88 nM, and L7ep-2a 2.26 nM. The solid line represents the fit of the data to equation 1.

$$v/E_t = k_{cat}(A)/(K_m+A) \quad \text{(Equation 1)}$$

Example 7

Stereoselective Hydrolysis of Racemic VX. Low initial concentrations (19 to 160 µM) of racemic VX were hydrolyzed by variants of PTE in a solution containing 0.1 mM $CoCl_2$, 0.3 mM DTNB, and 50 mM Hepes, pH 8.0. The reactions were followed to completion and the fraction of VX hydrolyzed plotted as a function of time. The time courses were fit to equations 2 and 3 where F is the fraction of substrate hydrolyzed, a and b are the magnitudes of the exponential phases, t is time, and $k_1$ and $k_2$ are the rate constants for each phase.

$$F = a(1-e^{-k_1 t}) \quad \text{(Equation 2)}$$

$$F = a(1-e^{-k_1 t}) + b(1-e^{-k_2 t}) \quad \text{(Equation 3)}$$

To identify which one of the two enantiomers of VX was preferentially hydrolyzed by the PTE variants, one gram of racemic VX was hydrolyzed in a 400 mL reaction mixture containing 50 mM bis-tris-propane (pH 8.0), 100 µM $CoCl_2$, and 36 nM of the QF mutant (H254Q/H257F) at 33° C. The reaction was monitored by determining the concentration of the thiol product with DTNB. When the reaction was approximately 50% complete, the remaining VX was extracted with 200 mL of ethyl acetate. The volume of the extract was reduced to approximately 2 mL by rotary evaporation at 41° C. The unreacted VX was analyzed with a polarimeter and observed to rotate plane polarized light in a positive direction (+0.055° to +0.075°) which corresponds to an enantiomeric preference for hydrolysis of the $S_P$-enantiomer of VX by the QF mutant.(17)

Example 8

Construction and Screening of Active Site Libraries. The variant QF (H254Q/H257F) was previously identified as being improved against the chiral centers in VX and VR.(18) Testing the catalytic activity of this mutant with the VX analogue, DEVX, revealed that this variant has an enhanced activity for the hydrolysis of the phosphorothiolate bond, relative to wild-type PTE. The amino acid residue numbering of the sequence including the leader sequence has been retained. The variant QF then served as the starting point for the construction of the F306X/Y309X and W131X/F132X double-substitution protein libraries. Screening 920 colonies from the F306X/Y309X library with DEVX failed to identify any variant that was improved relative to the QF parent. From the W131X/F132X library, a total of 1100 colonies were screened with DEVX and the two best mutants were identified as LQF (QF+F132L) and VQF (QF+F132V). The LQF variant served as the starting template for the 254X/257X library. Approximately 1650 colonies were screened from this library with DEVX, but none proved to be better for the hydrolysis of DEVX.

The 271X/308X library was created using sequential QuikChange procedures; first at position 271 then at position 308 using the LQF template. Approximately 2200 colonies from this library were screened and the best variant was LQFL (LQF+S308L). Incorporation of the new mutation (S308L) into the previously identified VQF variant further enhanced the catalytic activity. The variant VQFL (VQF+S308L) was utilized as the parent for the 106X/303X library. Approximately 1100 colonies were screened with DEVX and the best variant identified was CVQFL (VQFL+I106C). The variant CVQFL was carried forward in the construction of the 60X/317X library. Nearly 1500 colonies from this library were screened with DEVX, but improved variants were not detected.

A number of mutations are known to improve protein expression levels for PTE, including A80V, K185R, and I274N.(28,29) These mutations do not typically result in significant changes in the kinetic constants for a given substrate, but they dramatically improve the amount of enzyme produced per liter of cell culture. Adding these expression-enhancing mutations to VQFL resulted in an additional variant, VRN-VQFL (A80V/K185R/I274N+VQFL) with a 26-fold improvement in the value of $k_{cat}/K_m$, relative to the wild-type PTE. The inclusion of two additional expression-enhancing mutations (D208G/R319S) resulted in a decrease in catalytic activity.(29) Kinetic constants for the PTE variants with DEVX as the target substrate are presented in Table 2. Kinetic constants for additional variants are provided in Table 3.

TABLE 3

Activity of additional PTE Variants with DEVX.

| Variant | $k_{cat}(s^{-1})$ | $K_m$ (mM) | $k_{cat}/K_m (M^{-1}s^{-1})$ |
|---|---|---|---|
| QF.1 | 0.67 ± 0.01 | 2.2 ± 0.1 | (3.05 ± 0.01) × 10² |
| QF.a | 1.23 ± 0.02 | 2.3 ± 0.1 | (5.35 ± 0.02) × 10² |
| QF.b | 0.7 ± 0.2 | 1.9 ± 0.1 | (3.9 ± 0.1) × 10³ |
| LQF.1 | 10.1 ± 0.2 | 2.32 ± 0.08 | (4.4 ± 0.2) × 10³ |
| LQF.2 | 4.2 ± 0.2 | 4.1 ± 0.3 | (1.02 ± 0.08) × 10³ |
| LQF.3 | 8.4 ± 0.3 | 3.0 ± 0.2 | (2.8 ± 0.2) × 10³ |
| LQF.4 | 21.7 ± 0.4 | 2.91 ± 0.09 | (7.5 ± 0.2) × 10³ |
| LQF.a | 9.4 ± 0.2 | 1.62 ± 0.07 | (5.8 ± 0.3) × 10³ |
| LQF.b | 14.5 ± 0.4 | 2.8 ± 0.1 | (5.2 ± 0.3) × 10³ |
| LQF.c | 25.2 ± 0.8 | 2.8 ± 0.2 | (9.2 ± 0.6) × 10³ |
| LQF.d | 4.1 ± 0.3 | 13 ± 1 | (3.1 ± 0.4) 10×² |
| VQFL.1 | 24.9 ± 0.5 | 2.0 ± 0.1 | (1.23 ± 0.05) × 10⁴ |
| VQFL.2 | 20.4 ± 0.6 | 2.6 ± 0.1 | (7.9 ± 0.5) × 10³ |
| VQFL.3 | 0.93 ± 0.03 | 2.3 ± 0.1 | (4.1 ± 0.3) × 10² |
| L7ep-4 | 18.8 ± 0.3 | 0.89 ± 0.03 | (2.11 ± 0.08) × 10⁴ |
| L7er-5 | 13.4 ± 0.1 | 1.06 ± 0.02 | (1.26 ± 0.03) × 10⁴ |
| L7ep-6 | 17.2 ± 0.2 | 0.63 ± 0.02 | (2.73 ± 0.08) × 10⁴ |
| L7ep-7 | 18.4 ± 0.2 | 0.66 ± 0.02 | (2.81 ± 0.09) × 10⁴ |
| L7ep-8 | 16.2 ± 0.3 | 1.11 ± 0.04 | (1.45 ± 0.05) × 10⁴ |
| L7ep-9 | 16.3 ± 0.2 | 0.54 ± 0.02 | (3.0 ± 0.1) × 10⁴ |
| L7ep-10 | 9.6 ± 0.1 | 1.23 ± 0.03 | (7.8 ± 0.2) × 10³ |
| L7ep-11 | 17.1 ± 0.2 | 1.21 ± 0.03 | (1.42 ± 0.04) × 10⁴ |
| L7ep-12 | 5.74 ± 0.08 | 0.50 ± 0.02 | (7.8 ± 0.2) × 10³ |
| L72p-2c | 16.1 ± 0.6 | 1.6 ± 0.1 | (9.8 ± 0.8) × 10³ |
| L7ep-2d | 94 ± 3 | 1.7 ± 01 | (5.4 ± 0.3) × 10⁴ |
| L7ep-2e | 44 ± 2 | 1.24 ± 0.09 | (3.6 ± 0.3) × 10⁴ |
| L7ep-2f | 80 ± 2 | 1.58 ± 0.08 | (5.0 ± 0.3) × 10⁴ |
| L7ep-2g | 80 ± 2 | 1.58 ± 0.08 | (5.3 ± 0.4) × 10⁴ |
| L7ep-2h | 82 ± 2 | 0.94 ± 0.05 | (8.7 ± 0.3) × 10⁴ |
| L7ep-2i | 44 ± 1 | 0.88 ± 0.04 | (5.0 ± 0.3) × 10⁴ |
| L7ep-2j | 31 ± 1 | 0.8 ± 0.05 | (4.0 ± 0.3) × 10⁴ |
| L7ep-3c | 35.2 ± 0.5 | 0.79 ± 0.02 | (4.5 ± 0.1) × 10⁴ |
| L73p-3d | 25.2 ± 0.5 | 0.58 ± 0.03 | (4.4 ± 0.2) × 10⁴ |

Example 9

Construction of Targeted Error-Prone Library. The CVQFL variant was used as the parent for the construction of an error-prone library with an average of six mutations per gene, targeted exclusively to Loop-7 of PTE (residues 253-276). The amino acid residue numbering of the sequence including the leader sequence has been retained. Approximately 4000 colonies from this library were screened with DEVX and a total of 12 variants were identified as being more active than the parent, CVQFL. The values of $k_{cat}/K_m$ for the best variants, L7ep-1, L7ep-2 and L7ep-3, were improved 27-, 63-, and 36-fold, respectively, for the hydrolysis of DEVX.

The variant L7ep-2 (CVQFL+H254R/N265D/A270D/L272M/S276T) has 5 amino acid changes to the sequence of Loop-7, relative to the parent. These five sites, and residue positions 257 and 274, were subjected to further optimization. Two, two-site libraries (R254X/F257X, and M272X/I274X) and three, single-site libraries (D265X, D270X, and T276X) were constructed to ensure that the optimum amino acid residue is represented at each position. Screening the libraries with DEVX revealed no improvements at residue positions 254, 257, 265, or 270, but numerous improved combinations were identified in the 272X/274X library. One of these variants, L7ep-2a (L7ep-2+I274T), has a $k_{cat}$ of 135 s$^{-1}$ and a $k_{cat}/K_m$ 78-fold improved over wild type enzyme. To further optimize the L7ep-3 variant (CVQFL+H257Y/A270V/L272M), Loop-7 was subjected to a second round of targeted error-prone PCR. Screening with DEVX identified two variants, L7ep-3a (L7ep-3+I274N) and L7ep-3b (L7ep-3+A270D) that were substantially improved over the parent enzyme. Similar experiments were attempted using L7ep-2 as the starting template, but no improved variants were identified. The kinetic constants for the hydrolysis of DEVX by these mutants are presented in Table 2 and Table 3.

Example 10

Stereoselectivity of PTE Variants for Chiral VX Analogues. In this investigation there was no attempt to include a stereochemical preference in the screening of mutant libraries. Wild-type PTE is known to have a slight preference for the $S_P$-enantiomer of the VX chiral center.(18) To determine that there were no perturbations in stereo selectivity, the variants with improved catalytic activity against DEVX were analyzed using the chromophoric analogues $R_P$-1 and $S_P$-1, and the results are presented in Table 2. With the exception of L7ep-2, L7ep-2a, and L7ep-2b, the evolved variants have values of $k_{cat}/K_m$ that are greater for the $S_P$-enantiomer than for the $R_P$-enantiomer.

Example 11

Enzymatic Specificity. To assess changes in substrate specificity, the enzyme variants were tested with paraoxon and demeton-S as alternative substrates. The results are provided in Table 4. The variants from the active site evolution experiments maintain a high enzymatic efficiency for paraoxon, although it is reduced nearly an order of magnitude from wild-type enzyme. The catalytic activity using demeton-S did not show any significant improvement for most of the variants tested. The exceptions are L7ep-2, L7ep-2a, and L7ep-2b, which have increased $k_{cat}$ and decreased $K_m$ values for demeton-S.

TABLE 4

Kinetic parameters for PTE variants with paraoxon and demeton-S$^a$.

| | Paroxon | | | Demeton-S | | |
|---|---|---|---|---|---|---|
| Variant | $k_{cat}$ (s$^{-1}$) | $K_m$ (µM) | $k_{cat}/K_m$ (M$^{-1}$s$^{-1}$) | $k_{cat}$ (s$^{-1}$) | $K_m$ (mM) | $k_{cat}/K_m$ (M$^{-1}$s$^{-1}$) |
| WT | 6700 | 100 | 6.7 × 10⁷ | 1.4 | 1.2 | 1.1 × 10³ |
| QF | 41 | 5.3 | 7.7 × 10⁶ | 6.3 | 2.6 | 2.7 × 10³ |
| LQF | 72 | 11.1 | 6.5 × 10⁶ | 4.4 | 3.3 | 1.3 × 10³ |
| VQF | 108 | 10.5 | 1.0 × 10⁷ | 10 | 6.1 | 1.7 × 10³ |
| LQFL | 90 | 11 | 8.2 × 10⁶ | 5.2 | 3.1 | 1.7 × 10³ |
| VQFL | 66 | 5.4 | 1.2 × 10⁷ | 4.2 | 3.9 | 1.1 × 10³ |
| CVQFL | 38 | 5.6 | 6.8 × 10⁶ | 6.1 | 2.5 | 2.4 × 10³ |
| VRN-VQFL | 116 | 8 | 1.5 × 10⁷ | 7.1 | 2.8 | 2.5 × 10³ |
| VRNGS-VQFL | 227 | 8.5 | 2.7 × 10⁷ | 6.8 | 3.1 | 2.2 × 10³ |
| L7ep-1 | 1590 | 116 | 1.4 × 10⁷ | 0.12 | 1.0 | 1.2 × 10² |
| L7ep-2 | 245 | 93 | 2.6 × 10⁶ | 73 | 0.84 | 8.7 × 10⁴ |
| L7ep-3 | 146 | 11.2 | 1.3 × 10⁷ | 3.4 | 2.4 | 1.4 × 10³ |
| L7ep-2a | 243 | 46 | 5.3 × 10⁶ | 32 | 0.58 | 5.4 × 10⁴ |
| L7ep-2b | 280 | 13.5 | 2.1 × 10⁷ | 53 | 0.57 | 9.2 × 10⁴ |
| L7ep-3a | 85 | 7.2 | 1.2 × 10⁷ | 1.8 | 2.5 | 7.4 × 10² |

$^a$Standard errors from fits of the data fit to equation 1 are less than 10% of the stated values

Example 12

Hydrolysis of Racemic VX. Wild-type PTE and selected variants were characterized using racemic VX as a substrate and the results are presented in Table 5. Wild-type PTE has a low $k_{cat}$ (0.9 s$^{-1}$) and relatively high $K_m$, resulting in a diminished $k_{cat}/K_m$ for the hydrolysis of VX. The variant QF dramatically improves both $k_{cat}$ and $K_m$ values resulting in a 100-fold increase in $k_{cat}/K_m$. The VRN-VQFL variant had the highest value of $k_{cat}/K_m$ that was increased more than 230-fold over wild-type enzyme. VRN-VQFL includes the following mutations A80V, K185R, I274N, F132V, H254Q, H257F, and S308L. The L7ep-3a had the highest $k_{cat}$ and was increased more than 150-fold, relative to wild-type PTE. The QF mutant was shown to preferentially hydrolyze the S$_P$-enantiomer of VX by polarimetry.

TABLE 5

Activity of PTE variants with racemic VX[a].

| Variant | $k_{cat}$ (s$^{-1}$) | $K_m$ (mM) | $k_{cat}/K_m$ (M$^{-1}$s$^{-1}$) | Stereo-chemical Preference[b] |
|---|---|---|---|---|
| WT | 0.9 ± 0.1 | 2.9 ± 0.9 | 3 ± 1 × 10$^2$ | ND[c] |
| QF | 16 ± 1 | 0.5 ± 0.1 | 3.0 ± 0.6 × 10$^4$ | 12:1 (S$_P$) |
| CVQFL | 45 ± 6 | 2.1 ± 0.7 | 2.2 ± 0.8 × 10$^4$ | 1:1 |
| VRN-VQFL | 44 ± 1 | 0.59 ± 0.09 | 7 ± 1 × 10$^4$ | 3:1 |
| L7ep-1 | 11 ± 1 | 0.8 ± 0.2 | 1.4 ± 0.3 × 10$^4$ | ND |
| L7ep-2 | 25 ± 2 | 1.3 ± 0.3 | 2.2 ± 0.3 × 10$^4$ | 5:1 |
| L7ep-3 | 31 ± 2 | 0.5 ± 0.2 | 6 ± 2 × 10$^4$ | 4:1 |
| L7ep-2a | 56 ± 4 | 3.4 ± 0.7 | 1.6 ± 0.4 × 10$^4$ | 4:1 |
| L7ep-2b | 56 ± 14 | 8 ± 3 | 7 ± 4 × 10$^3$ | 12:1 (R$_P$) |
| L7ep-3a | 137 ± 22 | 5 ± 2 | 3 ± 1 × 10$^4$ | 4:1 |

[a]Standard errors from fits of the data to equation 1.
[b]Identity of preferred enantiomer was not determined for variants with less than a 10-fold preference.
[c]ND = not determined.

Stereoselective hydrolysis of racemic VX by the PTE mutants was evaluated by analyzing the time courses for the complete hydrolysis of VX at concentrations below the Michaelis constant. The presence of stereoselectivity in these time courses is manifested as the appearance of two exponential phases as observed with the QF variant where the ratio of rate constants is 12:1 (FIG. 5A).

Figure 5:
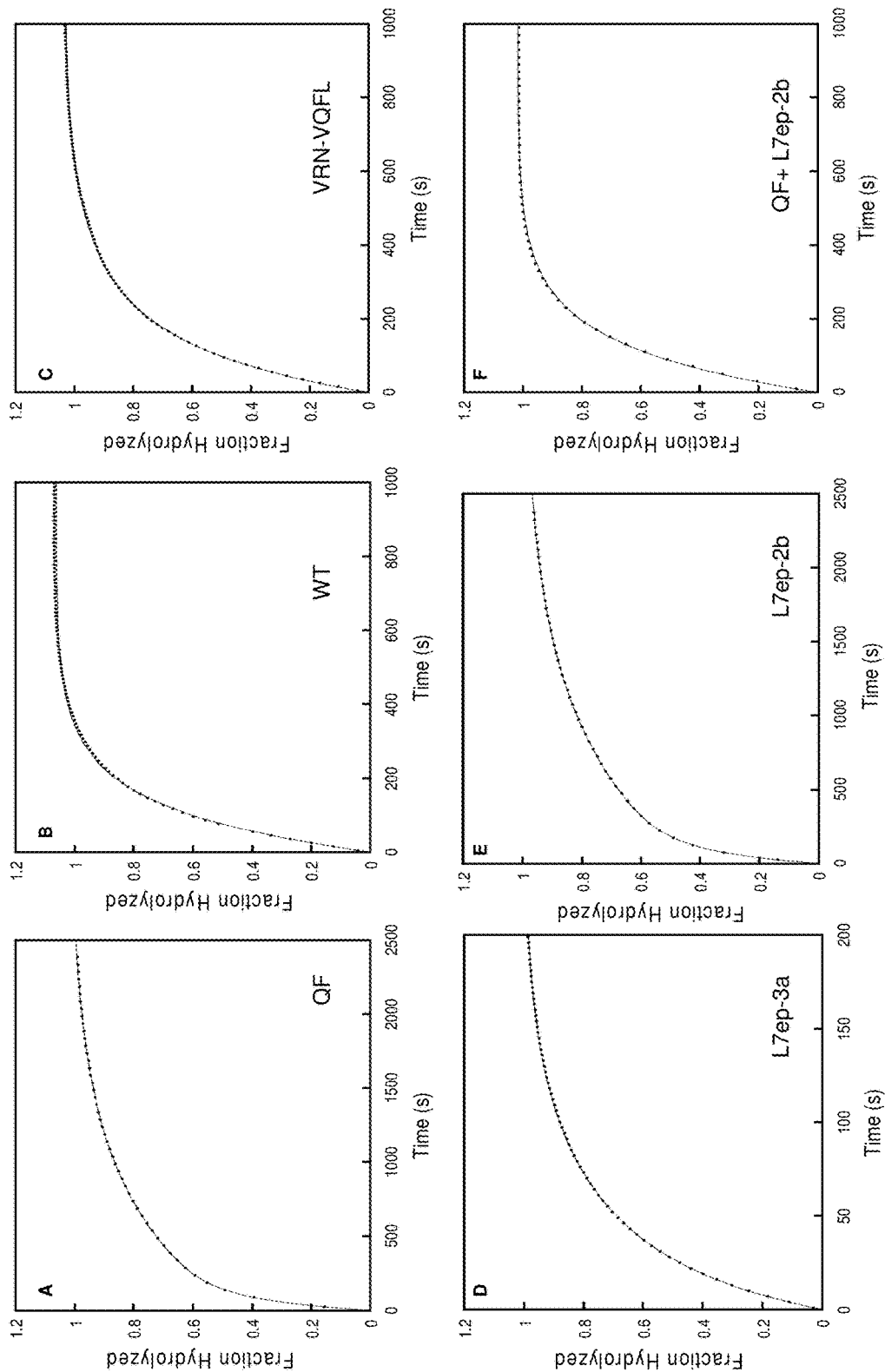

FIG. 5. Representative time courses for the complete hydrolysis of racemic VX by selected PTE variants. (A) QF; (B) WT; (C) VRN-VQFL; (D) L7ep-3a (E) L7ep-2b; and (F) L7ep-2b and QF. The time courses for panels B and F were fit to equation 2, while the data for panels A, C, D, and E were fit to equation 3.

Figure 1:
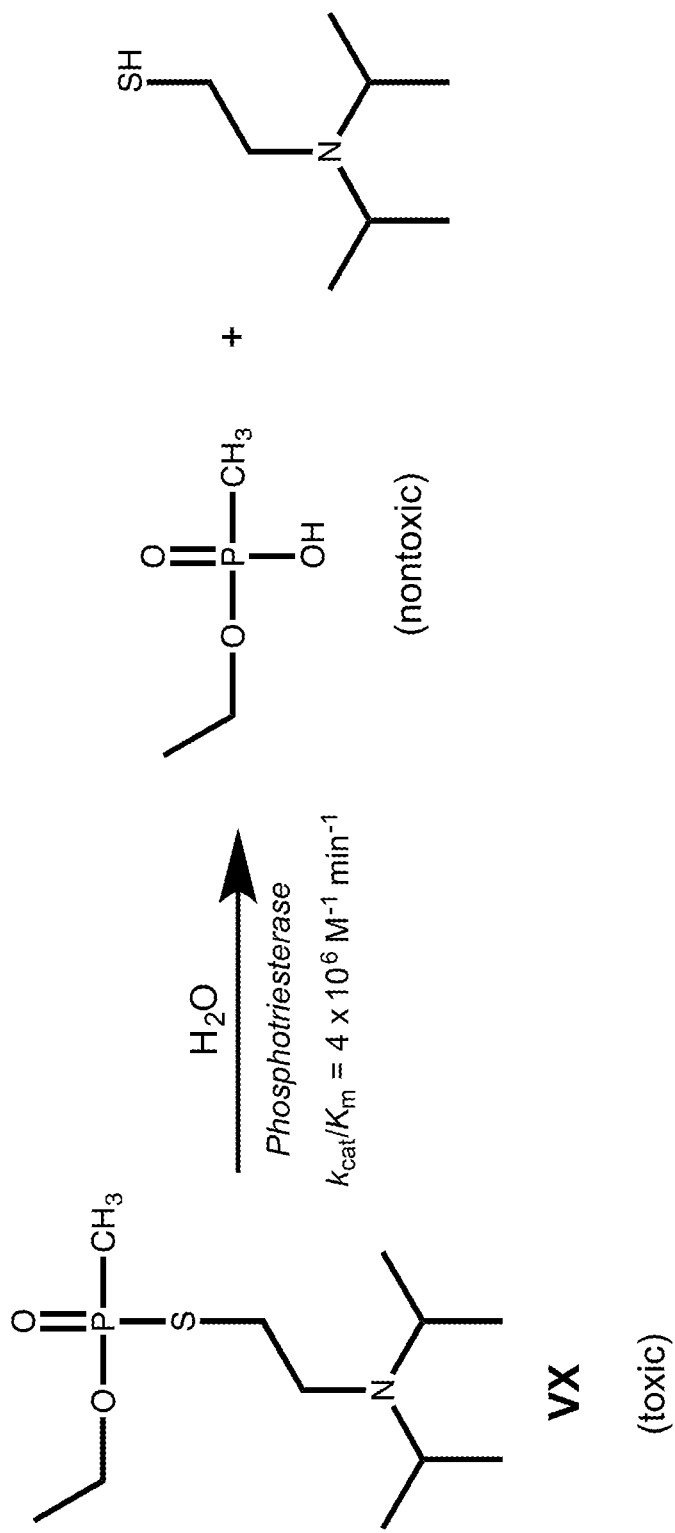
Figure 2:
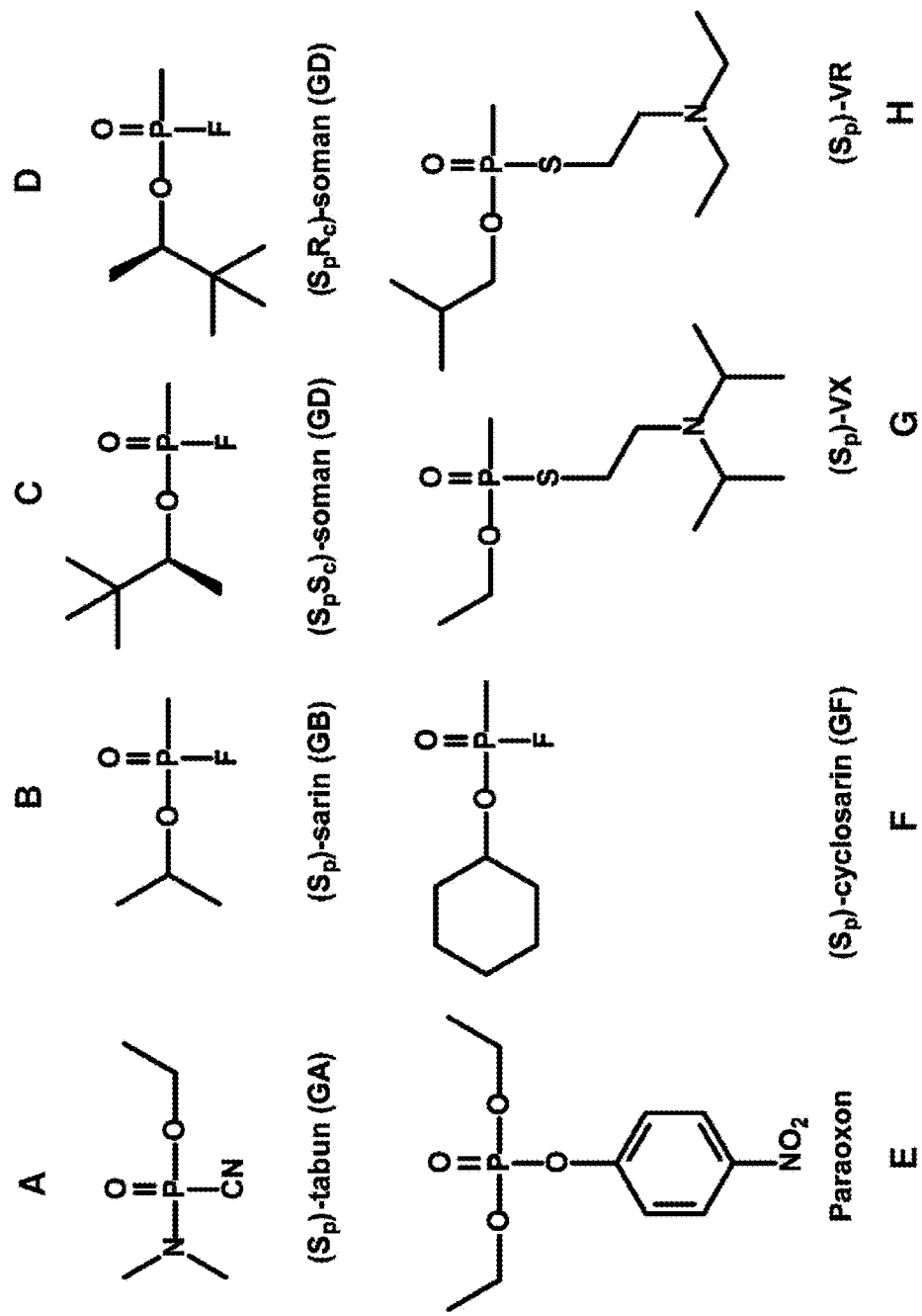
Figure 3:
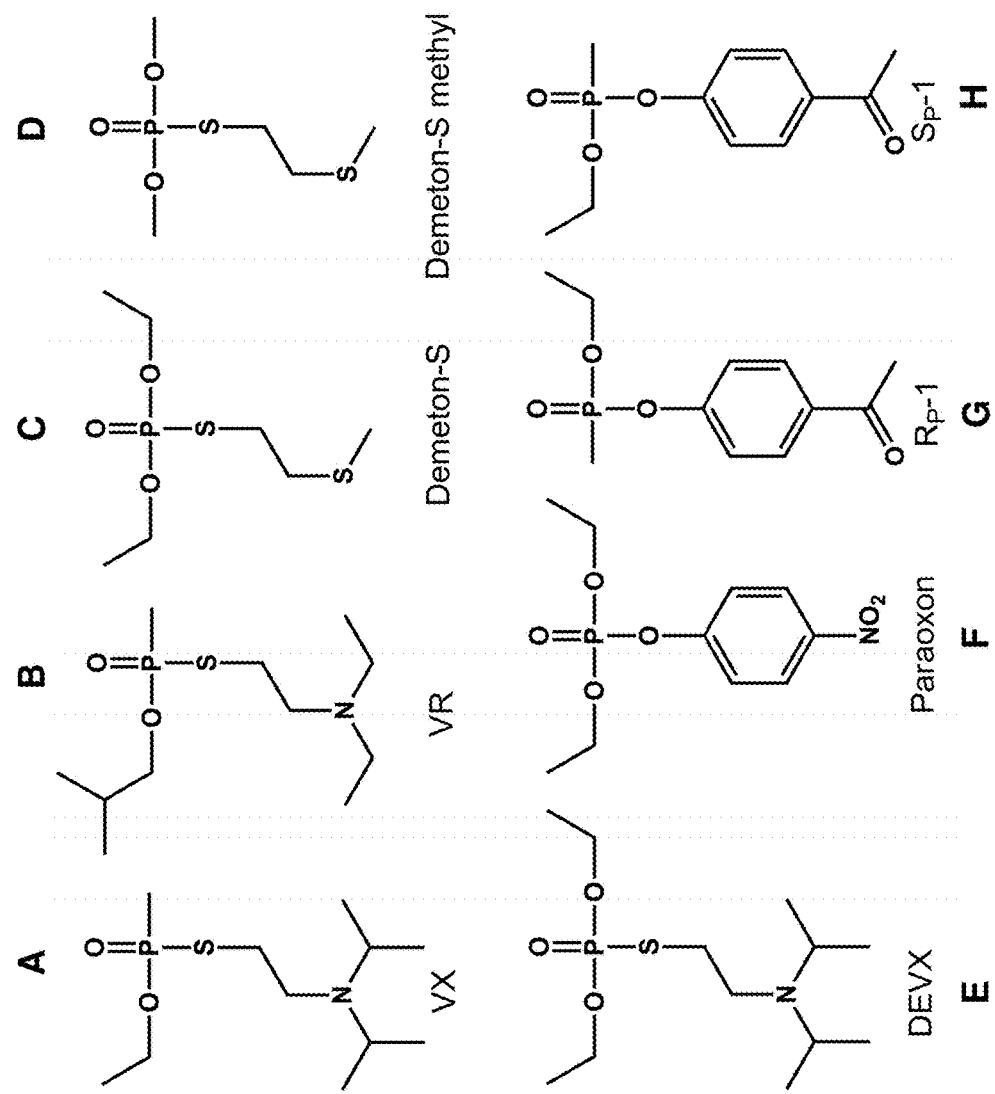

The CVQFL variant exhibited no selectivity (FIG. 5B), whereas the variants VRN-VQFL (3:1) and L7ep-3a (4:1) displayed relatively low selectivity (FIGS. 2C and 2D). For the L7ep-2b mutant, the observed stereoselectivity was 12:1 (FIG. 5E). The enantiomeric specificity of the L7ep-2b variant was determined by its ability to complement the hydrolysis of the slower R$_P$-enantiomer of VX after the addition of the variant QF. Plots of the fractional hydrolysis of VX as a function of time give two well-defined phases for each of these two variants (FIG. 5A and FIG. 5E). Mixing the two variants together resulted in a single well-defined monophasic curve demonstrating that the two variants prefer the opposite enantiomers (FIG. 5F). Therefore, the L7ep-2b variant preferentially hydrolyzes the R$_P$-enantiomer of VX. The ratios of rate constants for the L7ep-2, L7ep-3, and L7ep-2a mutants were 5:1, 4:1, and 4:1, respectively (Table 5). In the absence of enantiomerically pure VX, the modest selectivities for these variants prevented the definitive assignment of the preferred enantiomer.

Example 13

Construction of Active Site libraries by Overlap Extension. Mutagenic primers contained an NNS codon at the position of interest and extended 15 bp to either side of this codon. The PTE gene was amplified in three segments using standard PCR techniques (10 ng template and 125 ng each primer in a 50 µL reaction using pfuTurbo polymerase). The first segment extended from the 5' end of the gene to 15 bp beyond the first mutagenic position. The second segment extended from 15 bp upstream of the first mutagenic position to 15 bp downstream of the second mutagenic position. The third segment extended from 15 bp upstream of the second mutagenic site to the 3' end of the gene. The 5' and 3' primers included NdeI and EcoRI restriction sites respectively. A second PCR reaction was performed using the generated segments as the template DNA. The three fragments were combined in equimolar ratio (500 ng total) and amplified for 30 cycles with pfuTurbo using the primers for the 5' and 3' ends of the PTE gene. The overlaps between the fragments allowed for the formation of a single product corresponding to the size of the complete PTE gene. The product and vector were then digested with NdeI and EcoRI, gel purified and ligated together.

Example 14

Construction of Error Prone Library. Primer pairs used to amplify Loop-7 corresponding to the DNA sequence for residues 242-252 and 277-287. The reaction contained 20 ng template (CVQFL variant), 1 µM forward and reverse primers, 0.35 mM dATP, 0.4 mM dCTP, 0.2 mM dGTP, 1.35 mM dTTP, 1 mM MgCl$_2$, 1× GoGreen Taq Buffer (Promega, Madison Wis.) 1.5 mM MnCl$_2$ and 1 µL Go Taq in 50 µL reaction. Thermocycler program was 2 min initial denaturation at 95° C., followed by 30 cycles of 95° C. for 45 s, 60° C. for 1 min, 72° C. for 3 min, and a final elongation at 72° C. for 10 min. The remaining portions of the PTE gene were amplified using standard PCR techniques with the reverse primers for the Loop-7 fragment and the 5' and 3' end primer, resulting in three overlapping fragments. The final gene product was constructed by the overlap extension technique as described above. The mutated gene was digested with NdeI and EcoRI and ligated into pET 20 b (40 µL reaction containing 60 ng vector DNA, 3× molecular excess of PTE gene product, 4 µL T4 DNA ligase buffer and 2 µL T4 DNA ligase (NEB). Sequencing confirmed an average of 6 base pair changes per gene in loop-7. The identities of mutants from this library are given in Table 3.

Example 15

Enzyme Expression and Purification. BL21 (DE3) cells containing plasmid with wild-type or variant PTE were grown for ~8 hours in 5 mL LB broth. 1 L cultures of Terrific Broth (12 g Tryptone, 24 g yeast extract, 4 mL glycerol, 2.3 g KH$_2$PO$_4$, 12.5 g K$_2$HPO$_4$ in 1 L H$_2$O) supplemented with 1.0 mM CoCl$_2$ were inoculated with 1 mL of the growing culture. Cells were grown overnight at 30° C. with shaking. Protein expression was induced by addition of 1.0 mM IPTG and expression proceeded for an additional 24 hours. Cells were harvested by centrifugation at 11,000 g for 10 minutes. Cell pellets were stored at −80° C. prior to use. Cells from 1 L of culture were resuspended in 100 mL purification buffer (50 mM HEPES (pH 8.5), 100 µM $CoCl_2$). Cellular lysis was achieved by sonication on ice for a total of 20 minutes using a medium power setting. Cell debris was removed by centrifugation at 18,500 g for 10 minutes. Protamine sulfate (0.45 g in 20 mL purification buffer) was added dropwise and incubated for 20 minutes to remove nucleic acids. Precipitated materials were removed by centrifugation at 18,500 g for 10 minutes. Supernatant was brought to 60% saturation with ammonium sulfate and stirred in the cold for 30 minutes to precipitate PTE. Protein was removed from the supernatant by centrifugation at 18,500 g for 20 minutes. The supernatant was decanted and the pellet re-dissolved in 5 mL purification buffer. Up to 5 mL of the protein solution was loaded on a Superdex 200 (16/60) preparatory size exclusion column on a GE Health Care (Piscataway, N.J.) AKTA FLPC system. Peak fractions were collected and assayed for activity against paraoxon. Fractions with the most activity were further purified using a gravity-fed DEAE column pre-equilibrated in purification buffer.

Example 16

Synthesis of DEVX. DEVX was made by the reaction of diethylchlorophosphate with N,N-diisopropylaminoethanthiol. 1.5 grams of N,N-diisopropylaminoethanthiol was added to 100 mL diethyl ether and cooled in a dry ice acetone bath and purged with $N_2$ gas. To this mixture, 7.5 ml of a 2.5 M solution of butyryl lithium in hexane was added. 1.5 g of diethylchlorophosphate was mixed with 30 mL diethyl ether in a separate flask purged with $N_2$ and cooled in a dry ice acetone bath. The cooled diethylchlorophosphate solution was then added to the thiol solution and the reaction stirred at room temperature for 3 hr. The reaction was then brought to 400 mL with ethyl ether and extracted with water to remove side products. Product was then extracted into the aqueous phase with 0.5 M HCl and ethyl acetate. The aqueous phase was neutralized with sodium bicarbonate and extracted with chloroform. The organic phase was dried over $MgSO_4$ filtered and evaporated yielding the desired product as a pure oil.

$^1H$ NMR (300 MHz, $CDCl_3$): 4.05-4.174 (4H, m, $OCH_2CH_3$), 3.20-2.50 (6H, m, $SCH_2CH_2N(CH)_2$), 1.41-1.36 (6H, t, J=6.9 Hz, $OCH_2CH_3$), 1.05-1.03 (12H, d, J=4.8 Hz, $CH(CH_3)_2$ $^{31}P$ NMR (121.4 MHz $CDCl_3$): 29.77 ppm.

Example 17

Purification of racemic VX. VX samples were Chemical Agent Standard Analytical Reference Material (CASARM) and were of the highest purity available, typically 99.9+/−5.4 weight % by oxidation—reduction titration, traceable to National Institute of Standards and Technology through 0.1 N iodine solution SRM 136e. However, as received, the VX gave high background readings at 412 nm at the concentrations required for kinetic analysis and therefore required further purification as follows: 80.1 µL neat VX was added to 120 µL isopropyl alcohol (to aid in dissolution), then added to 800 µL of 3 mM DTNB in 50 mM HEPES, pH 8.0. To this solution was added approximately 1 gram of Dowex® 1×4 chloride form beads (Sigma-Aldrich) and agitated gently for several minutes until the beads turned red. The VX was subsequently decanted and added to more beads until essentially all the yellow color was removed to the beads and the VX solution was almost colorless. A standard curve was then generated using 6, 30, 60 and 96 µM dilutions of VX, reacted to completion enzymatically. VX concentration in the bead-treated solution was determined by linear regression analysis using the standard curve from the direct dilutions of VX.

Example 18

NMR Data Acquisition: All spectra were recorded on non-spinning samples at 25±2° C. with a Varian Unity INOVA 600 spectrometer (600 MHz $^1H$ operating frequency) fitted with a triple resonance, z-gradient probe. Routine $^1H$ free induction decay (FID) data sets of 16,384 complex points were collected as summations of eight or 16 acquisitions recorded with 10 ppm spectral windows, 90° pulse widths of 12 µsec, and 2 sec relaxation delays before archiving to computer disk. FID data sets were apodized with a line broadening factor of 0.3 Hz before Fourier transformation into spectra, manual phase correction into pure absorption mode, and chemical shift referencing to external tetramethylsilane.

$^{31}P$ FID data sets of 65,536 complex points were collected as summations of 32 acquisitions using 100 ppm spectral windows and 90° pulse widths of 30 µsec. All $^{31}P$ data acquisitions incorporated inverse-gated 1H decoupling (decoupling only during FID acquisition) with a low power composite pulse sequence to increase signal-to-noise ratios without signal enhancements from $^1H$-$^{31}P$ nuclear Overhauser effects.(31) Spin-lattice relaxation times (T1) for the VX $^{31}P$ signal and that for the O-ethyl methylphosphonate (EMP) hydrolysis product were measured with the inversion recovery pulse sequence [180°-τ-90°-acquisition] incorporating nine randomized τ delays. For quantitative $^{31}P$ spectra, data sets were collected with relaxation delays>5T1 for all $^{31}P$ signals in the spectra (~12 sec) to allow complete signal relaxation, and the spectrometer carrier frequency was centered between the VX substrate signal (ca. 57 ppm) and that of the O-ethyl,methylphosphonate (EMP) hydrolysis product (ca. 23 ppm) to minimize off-resonance effects. The $^{31}P\{^1H\}$ ($^1H$ decoupled, $^{31}P$ observe) data sets were apodized with a 5 Hz line broadening factor before Fourier transformation into spectra and manual phase correction into pure absorption mode. $^{31}P$ chemical shift values in spectra were referenced to external 85% phosphoric acid at −0.73 ppm.(32)

Example 19

NMR Observation of Enzymatic Hydrolysis of VX: The enzymatic hydrolysis of VX in the presence of PTE enzymes was observed by using NMR spectroscopy to follow VX disappearance, or the appearance of its EMP hydrolysis product, over time. Enzymatic reactions were initiated by adding 0.1-25.0 µL of a single enzyme solution to a 1 mL aliquot of a racemic VX solution and briefly mixing before transferring to a NMR sample tube. This was immediately placed into the NMR spectrometer, and quantitative $^{31}P\{^1H\}$ FID data sets were acquired at 7.5 min time intervals over 20-75 min. Enzymatic hydrolysis rates were calculated directly from the integral values of the quantitative $^{31}P\{^1H\}$ signals, and included subtraction of the measured spontaneous rate (~55 mole hr$^{-1}$) determined in separate experiments. The VX signal intensity decreases throughout the entire time course of the experiment until 75.0 min., where ≥99% of the intensity has disappeared (FIG. 8). EMP signal intensity increases over this same time frame, and at 75 min., it is the only signal observed in the spectrum.

Oligonucleotide pairs that contained the mutated codons at the specified sites were used as primers to amplify the genes for the wild-type enzyme and the following mutant enzymes: QF, YT, and GWT. The identities of the mutants are listed in Table 6. The mutations were added to each template sequentially to make the following mutant proteins: RN, QFRN, YTRN, GWT-d1, and GWT-d2.

TABLE 6

Identification of Mutants

| Abbreviation | Mutations |
| --- | --- |
| RN | K185R/I274N |
| QF | H254Q/H257F |
| GWT | H254G/H257W/L303T |
| QF-RN | H254Q/H257F/K185R/I274N |
| YT-RN | H257Y/L303T/K185R/I274N |
| GWT-d1 | H254G/H257W/L303T/K185R/I274N |
| GWT-d2 | H254G/H257W/L303T/K185R/I274N/A80V |
| GWT-d3 | H254G/H257W/L303T/K185R/I274N/A80V/S61T |
| GWT-f1 | H254G/H257W/L303T/M317L/K185R/I274N |
| GWT-f2 | H254G/H257W/L303T/M317L |
| GWT-f3 | H254G/H257W/L303T/M317L/I106C/F132I/L271I/K185R/I274N |
| GWT-f4 | H254G/H257W/L303T/M317L/I106C/F132I/L271I/K185R/I274N/A80V |
| GWT-f5 | H254G/H257W/L303T/M317L/I106C/F132I/L271I/K185R/I274N/A80V/R67H |

Example 20

Figure 9:
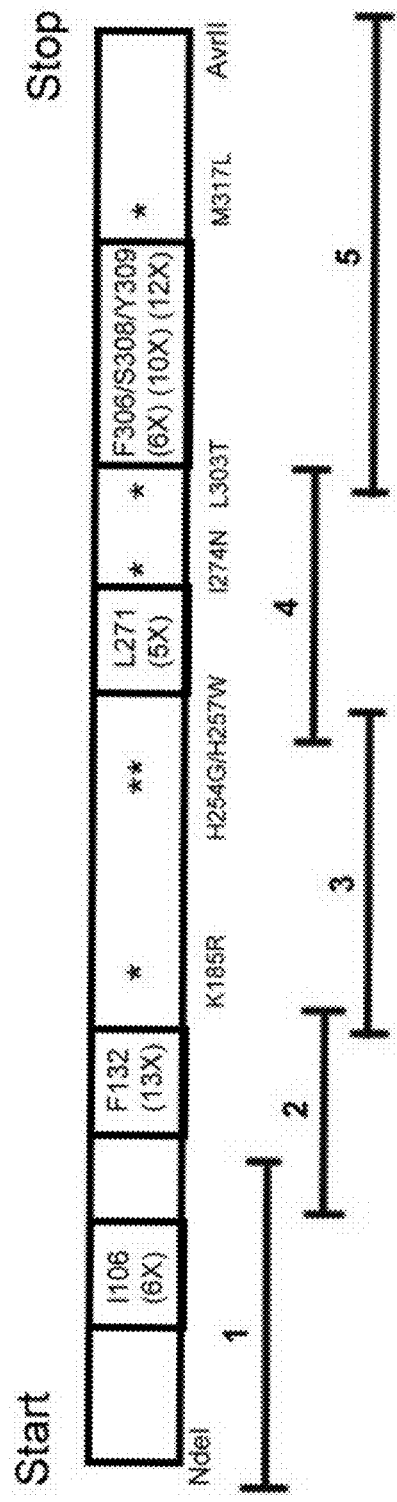

The multisite partially randomized PTE library was constructed by combining five separate segments of the gene for PTE as illustrated in FIG. 9 using primerless PCR for 15 cycles and then amplified by PCR for 55 cycles using primers specific for the 5' and 3' termini. The potential size of this multisite library is $1.9 \times 10^5$ variants. The numbers below the residue identifier indicate the number of amino acids that were allowed during the construction of the library. The amplified PTE library was digested with NdeI and Avr II restriction enzymes and ligated into the GpdQ-pETDuet plasmid using T4 DNA ligase. The ligation mixture was purified using the QIAquick Kit (Qiagen) and then transformed into freshly made E. coli Top 10 competent cells (Life Technologies). The transformants were incubated at 37° C. for 1 hour and then plated on Luria-Bertani ampicillin agarose. Approximately $5.7 \times 10^5$ colony forming units were collected and grown in LB medium for 6 hours at 37° C. The plasmids from the PTE library were extracted using the Promega Wizard Plus Miniprep Kit.

Example 21

Figure 10:
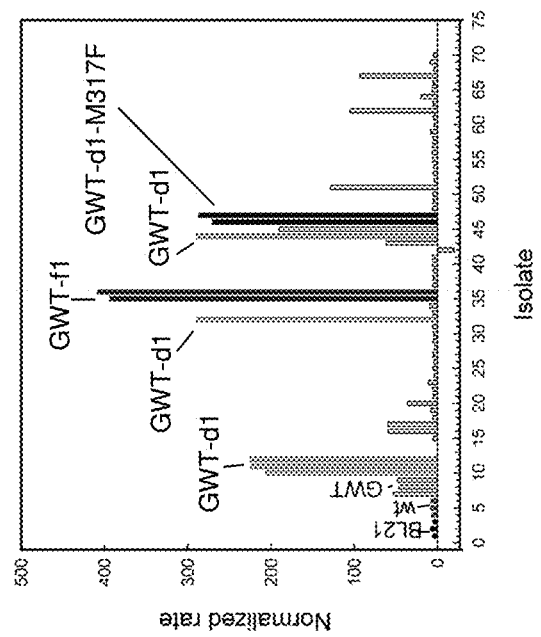

Mutant libraries were constructed using GWT-d1 as the starting template to identify more active PTE variants for the hydrolysis of $S_P$-5. Nine amino acid residues in the substrate binding pocket were considered as potential "hot spots" for the construction of these PTE libraries. The single substitution library M317X was constructed first, followed by four double substitution libraries (W131X/F132X, F306X/Y309X, S308X/Y309X, and I106X/Y308X). Approximately 60 colonies from the M317X library and around 550 colonies from each of the double-substitution libraries were picked and subsequently screened with $S_P$-5. The variants of GWT with catalytic activities higher than background from the first round of screening were isolated and then rescreened with the same substrate. (Table 6). No improvement in the hydrolysis of $S_P$-5 (FIG. 4F) was found in the double-substitution libraries, W131X/F132X, F306X/Y309X, S308X/Y309X, and I106X/Y308X. FIG. 10 illustrates the screening of the M317X single-substitution library. The bars represent the relative catalytic activities of the GWT-d1, GWT-f1, and GWT-d1-M317F mutants as labeled. Those mutants represented by the unlabeled bars were not characterized or sequenced. The best mutant identified in this screen contained a leucine substitution for Met-317 and is denoted GWT-f1. FIG. 10 depicts the screening of the M317X mutant library against $S_P$-5 using GWT-d1 as the parental template. The bars represent the relative catalytic activities of the GWT-d1, GWT-d1-M317F mutants, respectively.

Example 22

Figure 11:
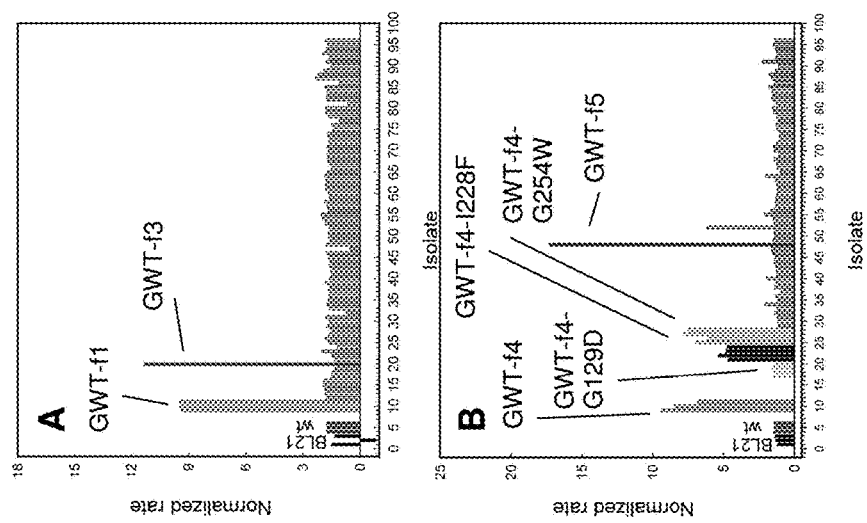

The GWT-f1 mutant was partially randomized at six sites simultaneously. The total library contained $1.9 \times 10^5$ potential variants. Eight colonies from this library were selected to verify that the targeted sites were randomized. The PTE/GpdQ-pETDuet plasmid library was transformed into E. coli BL21(DE3) cells. Approximately $5.8 \times 10^5$ CFU were plated on phosphate-free minimal medium with 1 mM $S_P$-5 as the sole phosphorus source. The colonies that contained beneficial mutations for the hydrolysis of $S_P$-5 were identified as being larger in size than a background colony of the parent GWT-f1 mutant. Approximately 30 of these colonies were selected for growth in 96-well blocks and subsequently assayed for catalytic activity with $S_P$-5. The screening of the partially randomized multisite library with $S_P$-5 is shown in FIG. 11A. The first nine samples include the empty vector control, wild-type PTE, and the GWT-f1 parent. A single variant was found to have more activity than the GWT-f1 parent. This mutant (GWT-f3) contained three additional changes in the amino acid sequence: I106C, F132I, and L271I. The A80V mutation was added to the GWT-f3 mutant to create the GWT-f4 variant.

In FIG. 11A, screening of the six-site randomized library using GWT-f1 as the parental template with $S_P$-5. The bars represent the relative catalytic activities of the GWT-f1 and GWT-f3 mutants as labeled.

The GWT-f4 mutant served as the template for error-prone PCR (epPCR). Random mutagenesis of the GWT-f4 gene was conducted using the Mutazyme II DNA polymerase. Ten colonies from this library were selected to establish an average mutation rate of ~1.5 mutations/1000 bp. The epPCR generated PTE/GpdQ-pETDuet library was transformed into E. coli BL21(DE3). Approximately $6 \times 10^5$ CFU were plated on phosphate-free minimal medium plates with 1 mM $S_P$-5 as the sole phosphorus source. Colonies larger in size than the parental strain (GWT-f4) were assayed with $S_P$-5, and the results are shown in FIG. 11B. The first 20 samples include the empty vector, wild-type PTE, GWT-f3, GWT-f3-G129D, GWT-f3-I288F, and GWT-f3-H254W. The new variant, GWT-f5, contained a single mutation, relative to GWT-f4, at Arg-67 with a change to histidine.

In FIG. 11B, screening of the error-prone PCR library using GWT-f4 as the parental template with $S_P$-5. The bars represent the relative catalytic activities of the GWT-f4, GWT-f4-G129D, GWT-f4-I228F, GWT-f4-G254W, and GWT-f5 mutants as labeled.

Example 23

Figure 12:
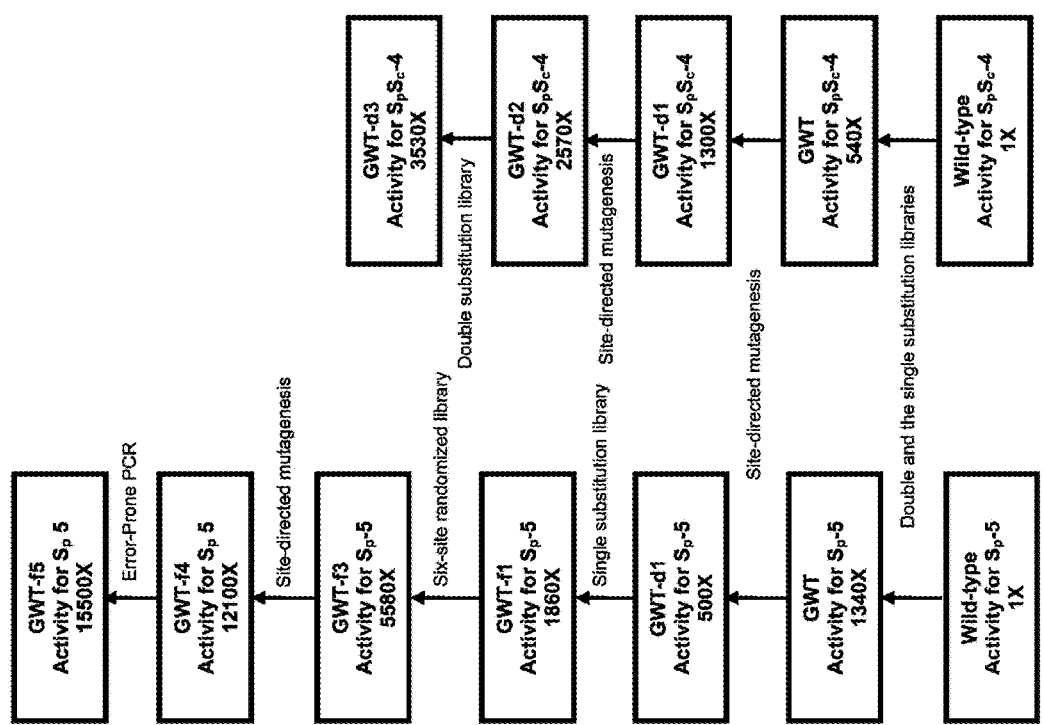
Figure 13:
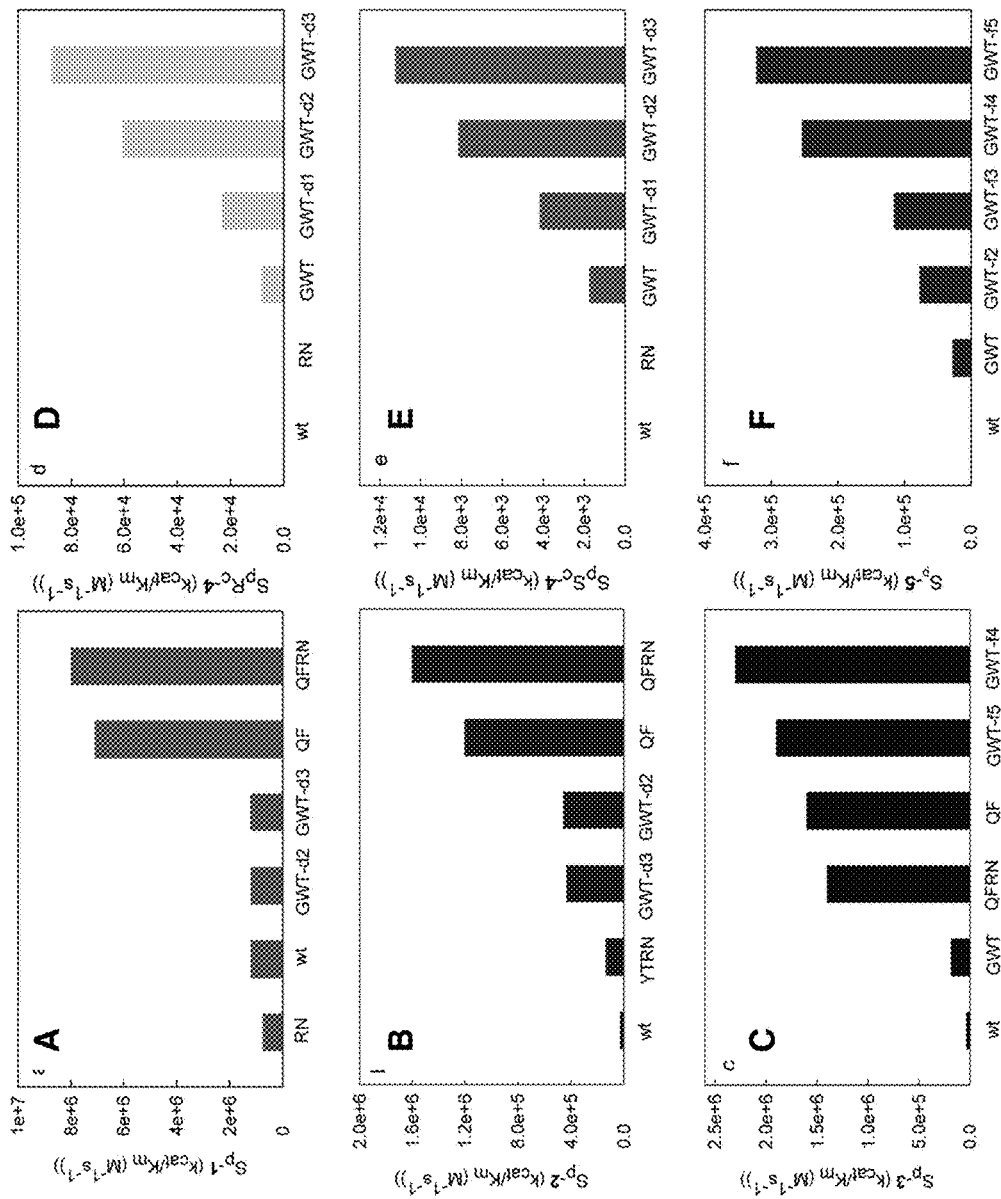
Figure 15:
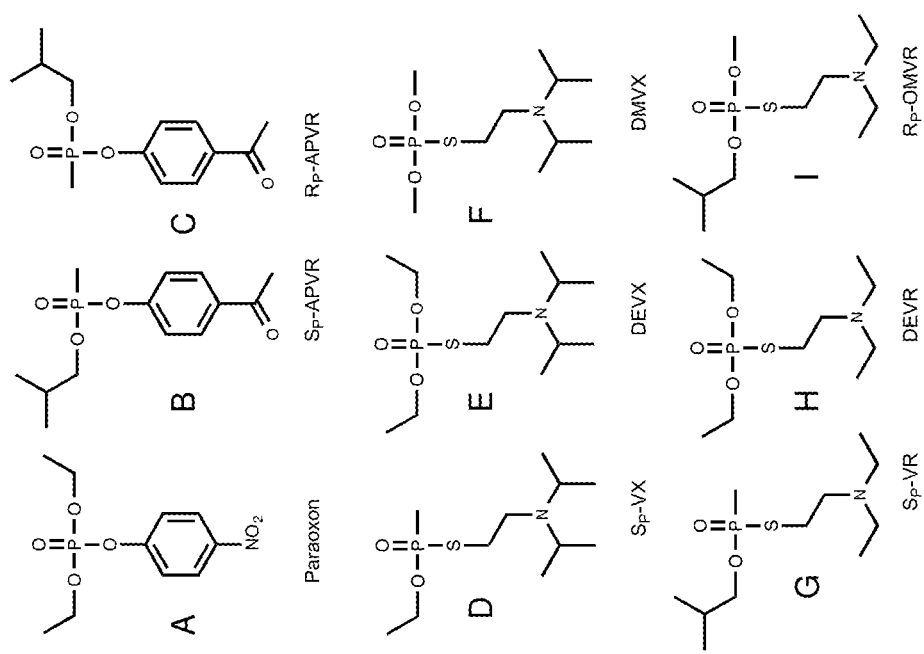

The outline for the discovery of PTE variants with enhanced activity for the hydrolysis of the $S_PS_C$-4 and $S_P$-5 (FIGS. 4D and 4F) by directed evolution is depicted in FIG. 12.

The structural modifications to GWT within the substrate binding pocket, surface and dimer interface have substantially enhanced substrate binding and catalytic turnover. The changes in the $k_{cat}/K_m$ values of the $S_P$-enantiomers of the organophosphonates are depicted in FIG. 13A-13F.

Kinetic constants for sarin (GB), soman (GD), and cyclosarin (GF) were determined by monitoring the release of free fluoride at 25° C. in 50 mM bis-tris-propane buffer (pH 7.2) using a fluoride electrode. Stereospecificity for hydrolysis of nerve agents was obtained by following the complete hydrolysis of 0.5 mM racemic mixtures of GB or GF. Reactions were conducted in 50 mM bis-tris-propane buffer (pH 7.2) and followed by the release of fluoride.

Example 24

Screening and Kinetic Analysis of Wild-Type and Mutant Enzymes on GB, GD, and GF. For the purposes of initial screening, specific activities were determined with 3 mM substrate (Table 7). The YT mutant was very active with all three substrates, and the YT-RN mutant had higher activity than the wild type with GD. Therefore, kinetic constants were determined for these enzyme-substrate combinations (Table 8). The stereospecificity of variants was determined by following the fluoride released during the complete hydrolysis of GB or GF using the 0.5 mM racemic substrate. Substantial differences in the rates for the individual enantiomers result in biphasic curves. The specificity of GWT toward GF is known from polarimetry experiments, (9) while the stereopreference of the remaining variants was determined by the ability of the variant to complement the slow phase in the GWT-catalyzed reaction (Table 7). YT has the same stereopreference as GWT for GF and has previously been shown to have the same preference as GWT for GD.(5) The stereopreference for the variants toward GB was determined by the ability to complement the slow phase in the YT-catalyzed reaction (Table 7). Adding mutations to the variants YT and YT-RN will likely provide variants that have improved activity with G-agents over wild-type PTE. Mutations at various locations within the sequence of the YT mutant will be added and their activity measured to identify variants that exhibit high activity with G-agents. Such variants would be useful in the decontamination of people, items, and locations contaminated with one or more G-agents. In an embodiment, further improvements in catalytic activity could be gained by simultaneously mutating pairs of residues in the active site. In an embodiment, error-prone PCR could be utilized to obtain mutations within PTE. In an embodiment, mutations within the active site of PTE could provide increased catalytic activity toward a G-agent. In an embodiment, methods disclosed regarding mutating PTE and determining activity with V-agents can also be utilized with mutating PTE and determining activity with G-agents.

TABLE 7

Activity of Wild-Type and Mutant Enzymes with Racemic G-Agents*

| Enzyme | GB | GD | GF | GB** preferred enantiomer | GF** preferred enantiomer |
|---|---|---|---|---|---|
| WT | 303 | 14 | 363 | NA*** | $R_P$ |
| YT | 843 | 212 | 240 | $S_P$ | $S_P$ |
| YT-RN | 263 | 115 | 116 | $S_P$ | $S_P$ |
| QF-RN | 32 | 1.0 | 41 | NA*** | NA*** |
| GWT | 20 | 2.0 | 44 | $S_P$ | $S_P$ |
| GWT-d1 | 57 | 2.0 | 7 | $S_P$ | $S_P$ |
| GWT-d2 | 52 | 1.0 | 211 | $S_P$ | $S_P$ |
| GWT-d3 | 48 | 8 | 35 | $S_P$ | $S_P$ |
| GWT-f3 | 142 | 10 | 94 | $S_P$ | $S_P$ |
| GWT-f5 | 240 | 19 | 59 | $S_P$ | $S_P$ |

*In micromoles per minute per milligram of protein.
**Determined with 0.5 mM racemic substrate.
***No significant stereopreference under these conditions.

TABLE 8

Kinetic Constants for Hydrolysis of GB, GD, and GF*

| Enzyme | substrate | $k_{cat}$ (s$^{-1}$) | $K_m$ (µM) | $k_{cat}/K_m$ (M$^{-1}$ s$^{-1}$) |
|---|---|---|---|---|
| WT | GB | 430 ± 50 | 1800 ± 400 | 2.4 (0.6) × 10$^5$ |
| WT | GD | 12 ± 1 | 800 ± 200 | 1.5 (0.4) × 10$^4$ |
| WT | GF | 210 ± 30 | 900 ± 300 | 2.3 (0.8) × 10$^5$ |
| YT | GB | 520 ± 30 | 260 ± 50 | 2.0 (0.4) × 10$^6$ |
| YT | GD | 240 ± 20 | 460 ± 90 | 5 (1) × 10$^5$ |
| YT | GF | 130 ± 10 | 170 ± 50 | 8 (2) × 10$^5$ |
| YTRN | GD | 100 ± 10 | 300 ± 100 | 4 (2) × 10$^5$ |

*Racemic mixtures of GB, GD, and GF were used for these measurements.

The kinetic parameters of the purified wild-type PTE and its mutants with the entire set of chiral organophosphonate compounds shown in FIGS. 4A-4L are provided in Tables 7, 9, and 10.

TABLE 9

Values of $k_{cat}$ (s$^{-1}$) for Wild-Type PTE and Its Mutants*

| | WT | QF | YT | RN | QFRN | YTRN | WT | GWT-d1 | GWT-d2 | GWT-d3 | GWT-f1 | GWT-f2 | GWT-f3 | GWT-f4 | GWT-f5 |
|---|---|---|---|---|---|---|---|---|---|---|---|---|---|---|---|
| $R_P$-1 | 1.5e2 | 1.7e2 | 7.3e0 | 9.0e1 | 2.0e2 | 1.2e1 | 1.4e1 | 1.4e1 | 1.3e1 | 9.6e0 | 1.3e1 | 2.2e2 | 7.9e1 | ND | ND |
| $S_P$-1 | 6.7e2 | 3.2e1 | 4.1e2 | 8.2e2 | 4.5e1 | 1.0e3 | 1.9e2 | 2.9e2 | 5.3e2 | 4.0e2 | 3.6e2 | 4.4e2 | 6.6e2 | 1.1e3 | 7.2e2 |
| $R_P$-2 | 1.0e2 | 4.8e1 | 1.8e1 | 6.6e1 | 6.6e1 | 2.0e1 | ND | 2.1e1 | 2.2e1 | 5.9e1 | 9.8e0 | 3.3e1 | ND | ND | ND |
| $S_P$-2 | 4.0e1 | 7.2e0 | 3.7e2 | 2.0e1 | 1.1e1 | 7.0e2 | 9.2e1 | 8.6e1 | 1.3e2 | 2.0e2 | 3.0e2 | 2.3e2 | 6.2e2 | 1.1e3 | 5.9e2 |
| $R_P$-3 | 9.3e1 | 7.0e1 | 5.1e1 | 4.8e1 | 1.3e2 | 4.3e1 | 2.0e1 | 8.0e0 | 1.3e1 | 2.2e1 | 2.9e1 | 3.4e1 | 1.3e1 | 1.5e1 | ND |
| $S_P$-3 | 2.2e1 | 6.3e0 | 1.0e2 | 1.6e1 | 1.3e1 | 7.7e2 | 5.0e1 | 5.5e1 | 5.8e1 | 6.0e1 | 8.0e1 | 8.8e1 | 1.4e2 | 2.5e2 | 1.8e2 |
| $R_PR_C$-4 | 3.4e0 | 5.5e-1 | 4.1e-1 | 4.5e0 | 1.1e0 | 5.8e-1 | 2.0e0 | 2.4e0 | 4.3e0 | ND | 4.0e0 | ND | ND | ND | 2.9e0 |
| $R_PS_C$-4 | 4.5e-1 | 1.7e-1 | ND | 4.2e-1 | 3.3e-1 | 1.9e0 | 2.1e-1 | 1.4e0 | ND | ND | 8.9e-1 | 1.9e0 | ND | ND | 1.9e0 |

TABLE 9-continued

Values of $k_{cat}$ (s$^{-1}$) for Wild-Type PTE and Its Mutants*

| | WT | QF | YT | RN | QFRN | YTRN | WT | GWT-d1 | GWT-d2 | GWT-d3 | GWT-f1 | GWT-f2 | GWT-f3 | GWT-f4 | GWT-f5 |
|---|---|---|---|---|---|---|---|---|---|---|---|---|---|---|---|
| $S_PR_C$-4 | 7.7e−1 | 6.3e−1 | 6.3e0 | 1.3e0 | 1.2e0 | 4.3e0 | 1.2e1 | 1.4e1 | 5.0e1 | 6.4e1 | 3.1e1 | 3.1e1 | 1.6e1 | 4.7e1 | 1.7e1 |
| $S_PS_C$-4 | 1.6e−2 | 3.3e−1 | 2.1e0 | ND | 5.e−1 | 3.2e0 | 2.9e0 | 6.5e0 | 1.2e1 | 2.4e1 | 5.7e1 | 8.1e0 | 4.2e0 | 5.6e0 | 6.1e0 |
| $R_P$-5 | ND | 3.8e1 | 5.9e0 | 2.5e1 | 2.2e1 | 1.7e1 | 8.1e−1 | ND | 9.7e−1 | ND | ND | ND | 2.2e0 | ND | 3.3e0 |
| $S_P$-5 | ND | ND | 5.1e0 | 1.3e−1 | 4.1e−1 | 7.2e0 | 1.9e1 | 3.1e0 | 4.7e1 | 4.4e1 | 2.6e1 | 3.1e1 | 4.4e1 | 1.2e2 | 1.2e2 |

*The standard errors, from fits of the data to $v/E_t$ = (kcat[A]/($K_m$ + [A]), are less than 20% of the stated values.
ND, not determined.

TABLE 10

Values of $k_{cat}/K_m$ (M$^{-1}$ s$^{-1}$) for Wild-Type PTE and Its Mutants*

| | WT | QF | YT | RN | QFRN | YTRN | GWT | GWT-d1 | GWT-d2 | GWT-d3 | GWT-f1 | GWT-f2 | GWT-f3 | GWT-f4 | GWT-f5 |
|---|---|---|---|---|---|---|---|---|---|---|---|---|---|---|---|
| $R_P$-1 | 4.9e5 | 1.5e6 | 2.4e3 | 1.7e3 | 3.0e6 | 4.3e3 | 1.5e3 | 2.5e3 | 6.1e3 | 9.1e3 | 1.0e5 | 5.2e4 | 6.1e3 | 7.2e3 | 8.5e3 |
| $S_P$-1 | 1.2e6 | 7.1e6 | 1.6e5 | 7.4e5 | 8.0e6 | 1.7e5 | 2.2e5 | 1.9e5 | 1.2e6 | 1.2e6 | 7.2e5 | 6.2e5 | 1.3e5 | 2.3e5 | 2.9e5 |
| Rp-2 | 5.8e5 | 8.2e5 | 2.5e3 | 2.8e5 | 1.6e6 | 3.4e3 | 1.8e3 | 3.5e3 | 6.0e3 | 8.1e3 | 1.4e4 | 4.7e3 | 3.4e3 | 4.2e3 | 6.1e3 |
| $S_P$-2 | 2.7e4 | 1.2e6 | 1.1e5 | 2.6e4 | 1.6e6 | 1.4e5 | 5.9e4 | 8.6e4 | 4.6e5 | 4.3e5 | 1.4e5 | 1.9e5 | 1.2e5 | 2.4e5 | 4.2e5 |
| $R_P$-3 | 8.5e5 | 3.1e5 | 1.3e4 | 4.0e5 | 1.3e6 | 1.3e4 | 1.5e3 | 3.0e3 | 5.4e3 | 7.6e3 | 3.3e3 | 3.8e3 | 8.2e2 | 2.6e3 | 2.2e3 |
| $S_P$-3 | 3.4e4 | 1.6e6 | 7.3e4 | 4.8e4 | 1.4e6 | 3.9e5 | 1.8e5 | 5.0e5 | 1.1e6 | 1.2e6 | 6.7e5 | 1.0e6 | 1.1e6 | 2.3e6 | 1.9e6 |
| $R_PR_C$-4 | 1.3e3 | 1.9e2 | 5.8e1 | 3.0e2 | 2.8e2 | 3.0e2 | 2.2e2 | 6.8e2 | 6.4e2 | 5.6e2 | 4.2e2 | 4.1e2 | 6.3e2 | 7.9e2 | 8.5e2 |
| $R_PS_C$-4 | 2.0e2 | 5.5e1 | 1.6e1 | 4.6e2 | 7.4e1 | 1.9e2 | 1.3e2 | 1.2e2 | 1.5e2 | 1.4e2 | 2.1e2 | 1.4e2 | 1.4e2 | 2.0e2 | 1.8e2 |
| $S_PR_C$-4 | 1.1e2 | 1.6e3 | 1.8e3 | 2.3e2 | 1.8e3 | 1.2e3 | 8.1e3 | 2.3e4 | 6.0e4 | 8.7e4 | 1.3e4 | 1.4e4 | 3.2e3 | 5.0e3 | 3.8e3 |
| $S_PS_C$-4 | 3.2e0 | 6.2e1 | 2.5e2 | 1.5e1 | 9.6e1 | 4.8e2 | 1.7e3 | 4.2e3 | 8.1e3 | 1.1e4 | 2.6e3 | 2.5e3 | 1.5e3 | 1.5e3 | 1.2e3 |
| $R_P$-5 | 1.6e4 | 5.2e3 | 1.9e3 | 1.7e4 | 9.0e3 | 3.5e3 | 2.5e2 | 3.0e2 | 5.4e2 | 5.5e2 | 6.0e2 | 8.6e2 | 4.5e2 | 5.1e2 | 7.7e2 |
| $S_P$-5 | 2.1e1 | 3.3e2 | 5.8e3 | 2.8e1 | 3.6e2 | 1.4e4 | 2.8e4 | 1.0e4 | 5.2e4 | 1.5e5 | 3.9e4 | 7.7e4 | 1.2e5 | 2.5e5 | 3.2e5 |

*The standard errors, from fits of the data to eq 1, are less than 20% of the stated values.

Example 25

Materials. Growth media and antibiotics were procured from Research Products Incorporated. DNA polymerase was obtained from Agilent. Other supplies for the molecular biology experiments were acquired from New England Biolabs. DEVX and N,N-diisopropylaminoethanethiol were synthesized as previously reported.(37, 44) The individual enantiomers of p-acetophenyl VR (APVR) were synthesized as previously reported.(39) Samples of VX and VR were Chemical Agent Standard Analytical Reference Material (CASARM) of the highest purity available, and were further purified as described previously.(37) Unless otherwise noted, all other chemicals were purchased from Sigma Aldrich. The organophosphorus nerve agents used in this investigation are highly toxic and should be used with the proper safety precautions. PTE: phosphotriesterase; DEVX: O,O-diethyl-VX; DMVX: O,O-dimethyl-VX; DEVR: O,O-diethyl-VR; and OMVR: O-methyl-VR.

Example 26

Synthesis of Dimethyl VX. Dimethyl VX (DMVX) was made by the reaction of dimethyl chlorophosphate with N,N-diisopropylaminoethanethiol. N,N-diisopropylaminoethanethiol (1.5 grams; 9.3 mmol) was added to 100 mL of diethyl ether and allowed to cool in a dry ice/acetone bath before being purged with $N_2$. To this mixture was added 7.5 mL (2.0 equivalents) of a 2.5 M solution of butyl lithium in hexanes and the reaction allowed to come to room temperature before re-cooling in a dry ice/acetone bath. Dimethyl chlorophosphate (2.0 g; 1.5 equivalents) was mixed with 30 mL of diethyl ether in a separate flask and cooled. The dimethyl chlorophosphate solution was then added to the thiol solution and the reaction stirred at room temperature for 3 hours. The reaction was brought to 400 mL with diethyl ether and extracted with water. The product was extracted into the aqueous phase with 0.5 M HCl. The aqueous phase was neutralized with sodium bicarbonate and extracted with dichloromethane. The organic phase was dried over $Na_2SO_4$, filtered, and evaporated to dryness. The product was further purified by silica gel chromatography. The product was dissolved in dichloromethane and eluted from the column using using a 0-5% step gradient of methanol in dichloromethane. Fractions containing the desired product were combined and the solvent evaporated to provide the product as an oil. Overall isolated yield was 8%. $^1$H NMR (300 MHz, CDCl$_3$): 3.84-3.77 (6H, d, J=12.6 Hz, OCH$_3$), 3.08-2.62 (6H, m, SCH$_2$CH$_2$N(CH)$_2$), 1.05-0.98 (12H, d, J=6.9 Hz, CH(CH$_3$)$_2$. $^{31}$P NMR (121.4 MHz, CDCl$_3$): 32.74 ppm.

Example 27

Synthesis of Diethyl VR. Diethyl VR (DEVR) was made by the reaction of diethyl chlorophosphate with N,N-diethylaminoethanethiol. N,N-diethylaminoethanethiol was prepared from the hydrochloride salt by dissolving the compound in a saturated NaHCO$_3$ solution and extraction with diethyl ether. The organic phase was dried over Na$_2$SO$_4$ and evaporated in vacuo at room temperature. The remaining oil was distilled (50° C.) under high vacuum and recovered as a pure liquid in a dry ice cooled trap. N,N-diethylaminoethiol (1.1 grams; 8.35 mmol) was added to 100 mL of diethyl ether and cooled in a dry ice/acetone bath before being purged with $N_2$. To this mixture was added 10 mL (3.0 equivalents) of a 2.5 M solution of butyl lithium in hexanes and the reaction allowed to come to room temperature before re-cooling in a dry ice/acetone bath. Diethyl chlorophosphate (2.9 g; 2 equivalents) was mixed with 30 mL of diethyl ether in a separate flask, purged with $N_2$, and then cooled in a dry ice/acetone bath. The cooled diethyl chlorophosphate solution was added to the thiol solution and the reaction stirred at room temperature for 3 hours. The reaction was brought to 400 mL with diethyl ether and extracted with water. The product was extracted into the aqueous phase with 0.5 M HCl. The aqueous phase was neutralized with sodium bicarbonate and extracted with dichloromethane. The organic phase was dried over $Na_2SO_4$, filtered, and then evaporated, yielding the product as an oil. Further purification was conducted using silica gel chromatography as described above. Overall yield of the isolated product was 7%. $^1$H NMR (300 MHz, $CDCl_3$): 4.27-4.10 (4H, m, $OCH_2CH_3$), 2.99-2.52 (8H, m, $SCH_2CH_2N(CH_2)_2$), 1.43-1.34 (6H, t, J=7.5 Hz, $OCH_2CH_3$), 1.11-1.01 (6H, t, J=7.2 Hz, $CH_2CH_3$). $^{31}$P NMR (121.4 MHz, $CDCl_3$): 28.50 ppm.

Example 28

Synthesis of O-methyl VR. O-methyl VR (OMVR) was synthesized by the reaction of methyl isobutyl chlorophosphate with N,N-diethylaminoethanethiol. N,N-diethylaminoethanethiol was prepared from the hydrochloride salt as described above. Methyl isobutyl chlorophosphate was prepared by dissolving 750 µL (8.4 mmol) of isobutanol in 50 mL of diethyl ether. The atmosphere was purged with $N_2$ and then the mixture was chilled in a dry ice/acetone bath. A total of 3.3 mL (1.0 equivalent) of 2.5 M butyl lithium in hexanes and 1.5 g (1.0 equivalents) of methyl dichlorophosphate was added, and the reaction stirred for three hours at room temperature.

In a separate flask, 1.2 g (1.0 equivalents) of N,N-diethylaminoethanethiol was dissolved in 50 mL of diethyl ether and chilled in a dry ice/acetone bath. A total of 5 mL (1.5 equivalents) of 2.5 M butyl lithium was added and the reaction warmed to room temperature. The methyl isobutyl chlorophosphate and the thiol solutions were chilled in a dry ice/acetone bath and combined. The reaction was allowed to proceed at room temperature for 3 hours. The reaction was then brought to 400 mL with diethyl ether and washed with water. The product was extracted with 0.5 M HCl, neutralized with sodium bicarbonate, and then extracted with dichloromethane. The organic phase was dried over $Na_2SO_4$ and evaporated to yield the product as an oil. Overall yield of final product was 15%. $^1$H NMR (300 MHz, $CDCl_3$): 3.92-3.72 (5H, m, $OCH_2CH(CH_3)_2$, $OCH_3$), 2.95-2.45 (8H, m, $SCH_2CH_2N(CH_2)_2$), 2.04-1.88 ($^1$H, $OCH_2CH(CH_3)_2$), 1.06-0.97 (6H, t, J=7.0 Hz, $NCH_2CH_3$), 0.97-0.90 (6H, d, J=6.8 Hz, $OCH_2CH(CH_3)_2$. $^{31}$P NMR (121.4 MHz $CDCl_3$): 30.30 ppm.

Example 29

Mutagenesis, Expression and Enzyme Purification. The gene for PTE was cloned into the expression vector pET 20b between the NdeI and EcoRI restriction sites as previously described.(39) The new variants of PTE were generated by introducing the mutations I106C, I106G, and L308S into the appropriate templates by site directed mutagenesis using the Quick Change (Agilent) protocol. DNA sequencing at the Gene Technologies Laboratory at Texas A&M University verified the specific mutations. The proteins were expressed and purified as previously described. (37) Briefly, the variants were freshly transformed into E. coli BL21 (DE3) cells by electroporation, and single colonies used to inoculate 5.0 mL cultures of LB medium. After 8 hours of growth at 37° C., 1.0 mL of this culture was used to inoculate 1 L cultures of Terrific Broth supplemented with 1.0 mM $CoCl_2$. The bacterial cultures were grown at 30° C. IPTG was added to a final concentration of 1.0 mM after 24 hours and growth continued for 40 hours. The cells were harvested by centrifugation and stored at −80° C. prior to purification. Cells were resuspended in 100 mL of purification buffer (50 mM HEPES, pH 8.5, with 100 µM $CoCl_2$) and then lysed by sonication. The cell debris was cleared by centrifugation, nucleic acids were precipitated by protamine sulfate (0.45 g in 20 mL purification buffer per liter of culture), and then removed by centrifugation. The PTE mutants were precipitated with ammonium sulfate (60% saturation) and recovered by centrifugation. The pellet was resuspended in ~5 mL of purification buffer, filtered (0.45 µm) and loaded onto a GE Superdex 200 (16/60) preparatory size exclusion column using a BioRad NCG FPLC system. Fractions with catalytic activity for the hydrolysis of paraoxon were pooled and then eluted from a 3.0 g (dry weight) DEAE Sephadex A25 resin that was pre-equilibrated in purification buffer. Protein purity was verified by SDS-PAGE.

Generation and Characterization of New PTE Variants. The PTE variants QF, CVQFL, VRN-VQFL and L7ep-3a were previously shown as having substantially improved activity for the hydrolysis of VX.(37) The stereoselectivity of these mutants for the chiral center contained in VR was determined using the isolated enantiomers of APVR (Table 11). With the exception of QF, the VX-optimized variants of PTE prefer to hydrolyze the $R_P$-enantiomer of the chiral center for VR. The crystal structure of L7ep-3a suggests that the mutations I106C and S308L affect the size of the small-group pocket. In order for the $S_P$-enantiomer of VR to productively bind in the active site, the larger isobutyl group must be positioned in the small-group pocket of PTE. In an effort to maximize the hydrolysis of $S_P$-VR, a series of variants was created to change the substitutions made to residues 106 and 308 in the variants previously optimized for the hydrolysis of VX.

TABLE 11

Kinetic constants for PTE variants with APVR[1].

| | $R_P$-APVR | | | $S_P$-APVR | | | |
|---|---|---|---|---|---|---|---|
| Enzyme | $k_{cat}$ $(s^{-1})$ | $K_m$ (mM) | $k_{cat}/K_m$ $(M^{-1}s^{-1})$ | $k_{cat}$ $(s^{-1})$ | $K_m$ (mM) | $k_{cat}/K_m$ $(M^{-1}s^{-1})$ | Ratio[2] |
| Wild-type | 84 | 1.7 | $4.9 \times 10^4$ | 25 | 4.5 | $6 \times 10^3$ | 8:1 R |
| QF | 57 | 0.36 | $1.6 \times 10^5$ | 8.7 | 0.030 | $2.9 \times 10^5$ | 1.8:1 S |
| CVQFL | 46 | 0.18 | $2.6 \times 10^5$ | 21 | 0.19 | $1.1 \times 10^5$ | 2.5:1 R |
| CVQFL C106I* | 50 | 0.15 | $3.3 \times 10^5$ | 14 | 1.5 | $9.5 \times 10^3$ | 35:1 R |
| CVQFL-I106G | 174 | 1.4 | $1.2 \times 10^5$ | 36 | 0.20 | $1.8 \times 10^5$ | 1.5:1 S |

TABLE 11-continued

Kinetic constants for PTE variants with APVR[1].

| | $R_P$-APVR | | | $S_P$-APVR | | | |
|---|---|---|---|---|---|---|---|
| Enzyme | $k_{cat}$ (s$^{-1}$) | $K_m$ (mM) | $k_{cat}/K_m$ (M$^{-1}$s$^{-1}$) | $k_{cat}$ (s$^{-1}$) | $K_m$ (mM) | $k_{cat}/K_m$ (M$^{-1}$s$^{-1}$) | Ratio[2] |
| CVQFL-L308S* | 122 | 2.0 | $6.0 \times 10^4$ | 8.1 | 0.19 | $4.2 \times 10^4$ | 1.4:1 R |
| CVQFL-I106G/L308S | 100 | 4 | $2.4 \times 10^4$ | 40 | 0.24 | $1.6 \times 10^5$ | 6.7:1 S |
| VRN-VQFL | 55 | 0.16 | $3.4 \times 10^5$ | 29 | 1.7 | $1.7 \times 10^4$ | 20:1 R |
| VRN-VQFL-I106C | 72 | 0.23 | $3.2 \times 10^5$ | 33 | 0.23 | $1.4 \times 10^5$ | 2.3:1 R |
| VRN-VQFL-I106G | 56 | 0.41 | $1.4 \times 10^5$ | 159 | 0.18 | $9.0 \times 10^5$ | 6.6:1 S |
| VRN-VQFL-L308S | 17 | 0.52 | $3.2 \times 10^4$ | 5.0 | 0.13 | $3.9 \times 10^4$ | 1.2:1 S |
| VRN-VQF-I106C/L308S | 160 | 1.7 | $1.0 \times 10^5$ | 51 | 1.5 | $3.4 \times 10^4$ | 3:1 R |
| VRN-VQFL-I106G/L308S | 45 | 2.1 | $2.2 \times 10^4$ | 53 | 0.18 | $3.0 \times 10^5$ | 14:1 S |
| L7ep-3a | 101 | 0.62 | $1.6 \times 10^5$ | 56 | 0.5 | $1.1 \times 10^5$ | 1.5:1 R |
| L7ep-3a I106G | 58 | 0.71 | $8.2 \times 10^4$ | 166 | 0.31 | $5.3 \times 10^5$ | 6.5:1 S |

*The mutations C106I and L308S are revertants back to the wild-type amino acid sequence.
[1]Errors from curve fitting are less than 10% with the exception of CVQFL-I106G/L308S, which has an error of 20% due to the high $K_m$ value.
[2]The ratio is $k_{cat}/K_m$ values for fast enantiomer and slow enantiomer, with the preferred enantiomer identified.

Example 30

Enzymatic Activity. Catalytic activity with paraoxon was followed by monitoring the release of p-nitrophenol at 400 nm ($\Delta E400=17,000$ M$^{-1}$ cm$^{-1}$) in 250 µL reaction volumes containing 50 mM CHES, pH 9.0, 100 µM CoCl$_2$, and 0-1.0 mM paraoxon. Activity with APVR utilized the same reaction conditions as paraoxon with the release of the leaving group monitored at 294 nm ($\Delta E294=7,710$ M$^{-1}$ cm$^{-1}$). Activity with DEVX, DMVX, DEVR, and OMVR was measured in 250 µL reactions containing 50 mM HEPES, pH 8.0, 100 µM CoCl$_2$, 0.3 mM DTNB and 0-1.0 mM substrate. The release of the thiol leaving group was followed by inclusion of DTNB in the assay mixture ($\Delta E412=14,150$ M$^{-1}$ s$^{-1}$). All assays were initiated by the addition of the appropriately diluted enzyme and monitored in a 96-well format using a Molecular Devices SpectraMax 364 Plus plate reader. Reactions were monitored for 15 minutes at 30° C. and the linear portion of the time course was used to calculate the initial rate. Kinetic constants were determined by fitting the data to the Michaelis-Menten equation.(45) When saturation could not be observed, the data was fit to a linear equation and the slope taken as $k_{cat}/K_m$.

The catalytic activities of these variants were first characterized against the insecticide paraoxon and the V-agent analog DEVX (Table 12), and then the stereochemical preferences were determined using APVR (Table 11).

TABLE 12

Kinetic parameters for PTE variants with paraoxon and DEVX[1].

| | Paraoxon | | | DEVX | | |
|---|---|---|---|---|---|---|
| Enzyme | $k_{cat}$ (s$^{-1}$) | $K_m$ (uM) | $k_{cat}/K_m$ (M$^{-1}$s$^{-1}$) | $k_{cat}$ (s$^{-1}$) | $K_m$ (mM) | $k_{cat}/K_m$ (M$^{-1}$s$^{-1}$) |
| Wild-type | 2230 | 81 | $2.8 \times 10^7$ | 1.1 | 0.87 | $1.2 \times 10^3$ |
| QF | 41 | 5.3 | $7.7 \times 10^6$ | 6.1 | 1.4 | $4.2 \times 10^3$ |
| CVQFL | 38 | 5.6 | $6.8 \times 10^6$ | 16 | 0.76 | $2.1 \times 10^4$ |
| CVQFL-C106I* | 66 | 5.4 | $1.2 \times 10^7$ | 14 | 0.65 | $2.2 \times 10^4$ |
| CVQFL-L308S* | 33 | 6.7 | $4.8 \times 10^6$ | 13 | 3.2 | $4.1 \times 10^3$ |
| CVQF-I106G/L308S | 48 | 25 | $1.9 \times 10^6$ | nd | nd | $3.1 \times 10^2$ |
| CVQFL-C106I/L308S | 108 | 11 | $1.0 \times 10^7$ | 19 | 1.0 | $1.9 \times 10^4$ |
| CVQFL-I106G | 456 | 22 | $2.0 \times 10^7$ | 31 | 2.8 | $1.1 \times 10^4$ |
| VRN-VQFL | 116 | 8 | $1.5 \times 10^7$ | 22 | 0.73 | $3.1 \times 10^4$ |
| VRN-VQFL-I106C | 103 | 5.3 | $1.9 \times 10^7$ | 23 | 0.80 | $2.8 \times 10^4$ |
| VRN-VQFL-I106G | 446 | 21 | $2.1 \times 10^7$ | nd | nd | $5.0 \times 10^3$ |
| VRN-VQFL-L308S | 15 | 1.7 | $8.8 \times 10^6$ | 5.1 | 0.35 | $1.5 \times 10^4$ |
| VRN-VQFL-I106C/L308S | 35 | 3.6 | $9.7 \times 10^6$ | 8.6 | 1.6 | $5.4 \times 10^3$ |
| VRN-VQFL-I106G/L308S | 58 | 9.2 | $6.2 \times 10^6$ | nd | nd | $4.1 \times 10^2$ |
| L7ep-3a | 142 | 7.2 | $1.2 \times 10e^7$ | 5 | 0.60 | $8.5 \times 10^4$ |
| L7ep-3a I106G | 545 | 33 | $1.67 \times 10^7$ | nd | nd | $7.7 \times 10^3$ |

*The mutations C106I and L308S are revertants to the wild-type amino acid sequence. [1] Errors from curve fitting were less than 10%.

Inclusion of the I106C mutation substantially reduced the preference for the hydrolysis of the $R_P$-enantiomer, while it tended to have relatively little effect on the hydrolysis of DEVX. For example, the CVQFL variant has a 2.5-fold preference for the $R_P$-enantiomer of the VR chiral center, but CVQFL-C106I has a 35-fold preference for the $R_P$-enantiomer. Despite this large difference in stereoselectivity, both of these variants hydrolyze DEVX with a $k_{cat}/K_m$ of ~$2 \times 10^4$ M$^{-1}$ s$^{-1}$. The removal of the S308L mutation from the VX-optimized variants also results in a substantial diminished preference toward the $R_P$-enantiomer, but in most cases it also resulted in diminished activity against DEVX. VRN-VQFL prefers the $R_P$-enantiomer of APVR by 20-fold. The variant VRN-VQFL L308S has a preference of 1.2-fold, but the activity against DEVX was also diminished 2-fold. When glycine was substituted at position 106, the stereochemical preference shifted to the $S_P$-enantiomer of APVR. L7ep-3a prefers the $R_P$-enantiomer by 1.5-fold, but L7ep-3a I106G prefers the $S_P$-enantiomer by 6.5-fold. Unfortunately, the I106G mutation reduced the activity against DEVX by more than an order of magnitude in these variants.

Example 31

Stereoselelctive Hydrolysis of Racemic VX and VR. Low initial concentrations (19 to 160 µM) of racemic VX and VR were hydrolyzed by variants of PTE in a solution containing 0.1 mM CoCl$_2$, 0.3 mM DTNB, and 50 mM Bis-Trispropane, pH 8.0. The reactions were followed to completion and the fraction hydrolyzed plotted as a function of time. The time courses were fit to equations 1 and 2 where F is the fraction hydrolyzed, a and b are the magnitudes of the exponential phases, t is time, and $k_1$ and $k_2$ are the rate constants for each phase.(39)

$$F = a(1-e^{-k_1 t}) \tag{1}$$

$$F = a(1-e^{-k_1 t}) + b(1-e^{-k_1 t}) \tag{2}$$

Stereochemical preferences were determined using the previously described complementation method.(37) Briefly, variants with large stereoselective preferences were placed in a reaction with mutants of PTE of known stereoselective preferences under conditions where each variant alone would exhibit a similar rate for the first exponential phase. If the variants prefer the same enantiomer, the resulting time course will exhibit two distinct phases. If the variants have the opposite enantiomers as the preferential substrate, the time courses will exhibit a single exponential phase.

Catalytic Activity with VX and VR. The most promising new variants were tested with racemic VX and VR. The assays were conducted for the complete hydrolysis of a single low concentration of these agents to enable the observation of exponential time courses, corresponding to the hydrolysis of each enantiomer contained within the racemic mixture. The kinetic constants are presented in Table 13. For enzyme variants with large stereochemical preferences, the identity of the preferred enantiomer was determined by the ability of the variant to complement the slow phase of a variant of known preference. Wild-type PTE is known to prefer to hydrolyze the $R_P$-enantiomer of the VR chiral center, while QF is known to prefer the $S_P$-enantiomer of VX.(37, 39) None of the variants tested, with the exception of QF, exhibited large stereochemical preferences for hydrolysis of the two enantiomers of VX. Removal of the S308L mutation (VRN-VQFL L308S) resulted in a 2-fold reduction in catalytic activity for the faster enantiomer of VX and a 5-fold reduction in the rate of hydrolysis for the slower enantiomer. Introduction of the I106G mutation (VRN-VQFL-I106G) led to the complete hydrolysis of racemic VX without detectable selectivity, but at a rate 6-fold slower than VRN-VQFL had for the slower enantiomer.

With racemic VR, the VRN-VQFL variant exhibited a 20-fold enhancement in the rate of hydrolysis compared to the wild-type enzyme, but this mutant was found to only hydrolyze the relatively nontoxic $R_P$-enantiomer of VR. Removal of the S308L mutation (VRN-VQFL L308S) enabled the hydrolysis of both enantiomers of VR, with complete loss of stereoselectivity. This represents a 64-fold improvement toward the hydrolysis of the toxic $S_P$-enantiomer compared to wild-type PTE. The introduction of the I106G mutation in the VRN-VQFL-I106G/L308S variant resulted in a strong preference for the hydrolysis of the $S_P$-enantiomer relative to the $R_P$-enantiomer. VRN-VQFL-I106G, which has both the I106G and S308L mutations, has much less stereochemical preference, but the kinetic data for the hydrolysis of the two enantiomers of APVR indicate that the stereochemical preference is for the SP-enantiomer. The best variant identified for the hydrolysis of VR was L7ep-3a I106G, which has a $k_{cat}/K_m$ of $2.6 \times 10^3$ $M^{-1}$ $s^{-1}$ for the faster enantiomer. While the stereoselectivity was not sufficient to determine the stereochemical preference with VR directly, the kinetic data with the two enantiomers of APVR has identified the preferred enantiomer as the highly toxic $S_P$-enatiomer. The L7ep-3a I106G mutant thus has a 620-fold enhanced rate of hydrolysis of $S_P$-VR relative to wild-type PTE.

Example 32

X-ray Crystallography. The PTE mutants L7ep-3a and L7ep-3a I106G were crystallized at 18° C. using the vapor diffusion method. In the crystallization experiments, 1.0 μL of protein (10 mg/mL with 1.0 mM $CoCl_2$) was mixed with 1.0 μL of the precipitant solution (100 mM sodium cacodylate pH 5.5-7.0, 0.2 M magnesium acetate, 15-30% PEG 8000), and then equilibrated against 500 μL of the same precipitant solution using Intelliplates. Protein crystals appeared within a week and grew to maximum dimensions (200 μm×15 μm×15 μm) after 21 days. Prior to data collection, the crystals were soaked for 30 seconds in a cryoprotectant solution of the mother liquor containing 30% ethylene glycol and then frozen in liquid nitrogen. Diffraction data were collected locally at 120 K on an R-AXIS IV detector with Cu Kα X-rays produced from a rotating anode generator. X-ray data reduction and scaling were performed with HKL2000.(46) Structures of the PTE mutants L7ep-3a and L7ep-3aG were determined by molecular replacement using the coordinates of wild type PTE (PDB id: 1DPM) as

TABLE 13

Kinetic constants with the racemic nerve agents VX and VR[1].

| Enzyme | VX | | | VR | | |
|---|---|---|---|---|---|---|
| | $k_{cat}/K_{m1}$ ($M^{-1}s^{-1}$) | $k_{cat}/K_{m2}$ ($M^{-1}s^{-1}$) | Ratio | $k_{cat}/K_{m1}$ ($M^{-1}s^{-1}$) | $k_{cat}/K_{m2}$ ($M^{-1}s^{-1}$) | Ratio[2] |
| Wild-type | $8.4 \times 10^1$ | nd | | $1.1 \times 10^2$ | $4.3 \times 10^0$ | 25:1 R |
| QF | $1.7 \times 10^4$ | $1.5 \times 10^3$ | 12:1 S | $4.8 \times 10^2$ | $7.9 \times 10^1$ | 6:1 |
| CVQFL | $1.0 \times 10^5$ | | 1:1 | $5.5 \times 10^3$ | $8.9 \times 10^2$ | 6:1 |
| VRN-VQFL | $1.1 \times 10^5$ | $4.3 \times 10^4$ | 4:1 | $2.4 \times 10^3$ | nd | >30:1 R |
| VRN-VQFL-I106G | $6.6 \times 10^3$ | | 1:1 | $2.0 \times 10^3$ | $4.1 \times 10^2$ | 5:1 |
| VRN-VQFL-L308S* | $6.2 \times 10^4$ | $8.9 \times 10^3$ | 7:1 | $2.7 \times 10^2$ | | 1:1 |
| VRN-VQFL-I106G/L308S | $4.9 \times 10^3$ | $1.7 \times 10^3$ | 3:1 | $2.1 \times 10^3$ | $6.7 \times 101$ | 31:1 S |
| L7ep-3a | $8.3 \times 10^5$ | $2.2 \times 10^5$ | 4:1 | $2.2 \times 10^3$ | $2.1 \times 10^2$ | 10:1 |
| L7ep-3a I106G | $2.0 \times 10^4$ | $6.2 \times 10^3$ | 3:1 | $2.6 \times 10^3$ | $6.9 \times 10^2$ | 3.8:1 |

*The mutation L308S is a revertant to the wild type amino acid sequence.
[1]Errors from curve fitting are less than 5%.
[2]The ratio is $k_{cat}/K_m$ values for fast enantiomer and slow enantiomer. If the preferred enantiomer is not listed it has not been determined.

the search model. The structures were built using COOT and refined with simulated annealing, B-factor randomization, and coordinate shaking using PHENIX.(47, 48) Later stages of refinement were also done in PHENIX using individual coordinate, anisotropic B-factor, and occupancy optimization. The PTE mutant structures were refined with $R_{work}/R_{free}$ values of 13.5-21.5% with excellent geometry (Table 14).

TABLE 14

X-ray crystallography data for L7ep-3a and L7ep-3a I106G.

| Variant | L7ep-3a | L7ep-3a I106G |
|---|---|---|
| Resolution, Å (Highest resolution shell) | 50.00-2.01 (2.04-2.01) | 50.00-2.01 (2.04-2.01) |
| Space group | $P2_1$ | $P2_1$ |
| Cell dimensions | | |
| a | 45.53 | 45.85 |
| b | 80.64 | 80.63 |
| c | 78.73 | 78.84 |
| γ | 106.60 | 106.94 |
| $R_{sym}$ | 0.087 | 0.057 |
| I/σI | 13.2 (3.0) | 18.9 (2.8) |
| Completeness, % (Highest resolution shell) | 98.3 (96.1) | 95.8 (91.1) |
| Redundancy (Highest resolution shell) | 3.5 (3.2) | 3.7 (3.2) |
| Refinement | | |
| Resolution, Å | 29.61-2.01 | 29.57-2.01 |
| No. of reflections | 35,603 | 34,657 |
| $R_{work}/R_{free}$ | 0.1574/0.2145 | 0.1348/0.1838 |
| No. of nonhydrogen atoms | | |
| Total | 5420 | 5395 |
| Water | 383 | 384 |
| B-factors | | |
| Protein | 27.56 | 28.08 |
| $Co^{2+}$ | 30.72 | 30.60 |
| Root mean square deviations | | |
| Bond lengths, Å | 0.006 | 0.007 |
| Bond angles, ° | 1.09 | 1.10 |
| Ramachandran | | |
| Favored, % | 97.4 | 97.1 |
| Allowed, % | 2.6 | 2.9 |
| Outliers, % | 0 | 0 |

Figure 16:
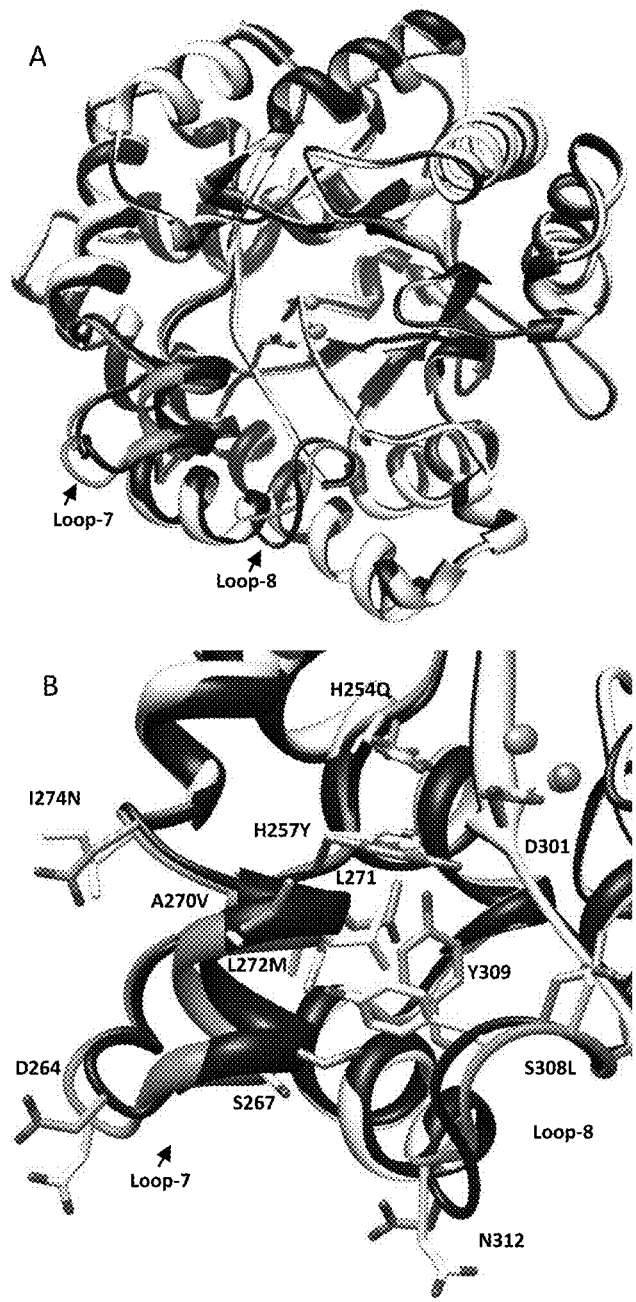

Three-Dimensional Structure of the PTE Mutant L7ep-3a. The PTE variant L7ep-3a has the highest reported $k_{cat}$ for the hydrolysis of the nerve agent VX.(37) In an effort to elucidate the mechanism by which the activity of this mutant is enhanced, the enzyme was crystallized and the structure determined to a resolution of 2.01 Å by X-ray diffraction methods (PDB id: 4ZST). FIG. 16 depicts (A) Structural alignment between wild-type PTE (light) and L7ep-3a mutant (dark). Selective active site residues are labeled and shown. Loop-7 and -8 are shown. (B) Expanded view of Loop-7 and -8. Mutated residues and residues with significant structural perturbations are shown as sticks. The wild type structure is taken from PDB id: 1DPM and the L7ep-3a structure is taken from PDB id: 4ZST. The overall structure of L7ep-3a is very similar to wild-type PTE (FIG. 16A). The core of the (β/α)8-barrel matches very well between the two structures with a Cα RMSD of 0.64 Å. The only significant change in the backbone structure is apparent in the conformations of Loop-7 and Loop-8. In this variant, Loop-7, including the Loop-7 α-helix, is pulled toward the active site (FIG. 16B). A portion of Loop-8 is similarly pulled toward the active site. Loop-8 also participates in the dimer interface, but the cross-interface interactions are all retained in the L7ep-3a mutant.

The binding site for the substrate in wild-type PTE is divided into the large-group pocket (His-254, His-257, Leu-271, and Met-317), the leaving-group pocket (Trp-131, Phe-132, Phe-306, and Tyr-309), and the small-group pocket (Gly-60, Ile-106, Lue-303 and Ser-308).(50) The mutations H257Y and S308L, coupled with the shifting of the Loop-7 α-helix, have induced significant changes in the substrate binding pockets in the active site of the L7ep-3a mutant. The side-chain of Tyr-309 is repositioned so that the phenolic group now extends into the active site rather than towards Loop-7, as previously observed in the structure of wild-type PTE (FIGS. 16B and 17).

Figure 17:
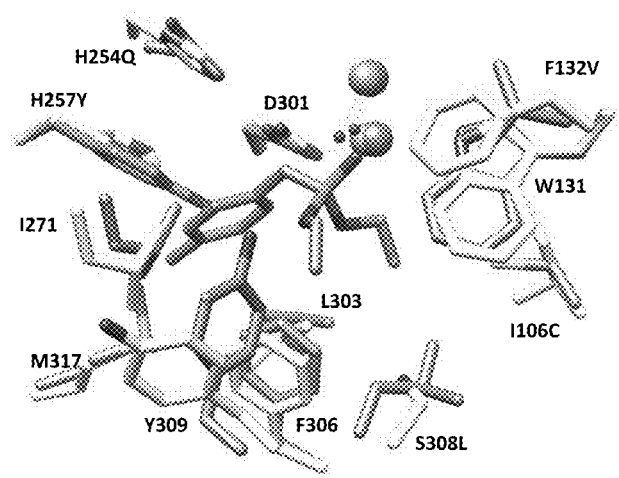

FIG. 17 depicts the substrate binding pockets of wild-type (white) and L7ep-3a (grey). The large-group pocket residues are His-254, His-257, Ile-271, and Met-317. The small-group pocket residues are Gly-60, Ile-106, Leu-303, and Ser-308. The leaving group pocket resides are Trp-131, Phe-132, Phe-306 and Tyr-309. The Wild-type structure (PDB id: 1DPM) is shown with the inhibitor, diethyl 4-methylbenzylphosphonate, bound in the active site.

The reorientation of Tyr-309, along with the substitution of a tyrosine for His-257 and the repositioning of Leu-271 into the active site, has dramatically compressed the size of the large-group and leaving-group pockets. The leaving-group pocket is also constricted by the presence of the S308L mutation, which adds bulk to both the leaving-group and small-group pockets. However, the apparent contraction of the leaving-group pocket is partially relieved by the F132V mutation. Similarly, the I106C mutation opens additional space to the small-group pocket.

Three-Dimensional Structure of L7ep-3a I106G. In an effort to understand the physical basis for the observed improvement in the catalytic activity of L7ep-3a I106G, the three-dimensional structure was solved by X-ray crystallography (PDB id: 4ZSU). The core structure is very similar to wild-type PTE (Cα RMSD=0.66 Å) and the loop structure matches that observed with L7ep-3a.

Example 33

Computational Docking of High Energy Intermediates. The pentavalent high-energy reaction intermediate states for the hydrolysis of VX and VR were computationally docked into the three-dimensional structures of wild-type PTE (PDB id: 1DPM), H254Q/H257F (PDB id: 2OQL), L7ep-3a (PDB id: 4ZST), and L7ep-3aG (PDB id: 4ZSU). The high energy intermediate states for the hydrolysis of the $R_P$- and $S_P$-enantiomers were manually generated as trigonal bipyrimidal structures with the attacking hydroxyl group protonated and the original phosphoryl oxygen substituent carrying a full negative charge using ChemBio Ultra 14.0. Computational docking was done using the program AutoDock Vina.(49) The appropriateness of the docked poses was evaluated by the value of the distance of the attacking hydroxyl group from the α- and β-metal ions, the distance of the phosphoryl oxygen from the β-metal and the orientation of the side ester substituents into the large and small group pockets contained in the active site of PTE.

Example 34

Evaluation of New V-agent Analogs. The majority of research targeting the catalytic hydrolysis of organophosphorus nerve agents must be done using analogs for both regulatory and safety reasons. Intrinsic to the use of substrate analogs is the imperfect representation of catalytic activity with the authentic nerve agent. To address which structural factors of the VR and VX analogs are most significant, the compounds DMVX, DEVR and OMVR were synthesized and analyzed as substrates for the optimized mutants of PTE and compared with the ability of these mutants to hydrolyze the most toxic forms of VR and VX. The catalytic activity using these compounds was determined with a series of variants for which the hydrolysis of authentic nerve agents was available (Table 15). Wild-type PTE has a much lower catalytic activity with DMVX ($k_{cat}/K_m$=1.9×101 $M^{-1}$ $s^{-1}$) than was observed with DEVX ($k_{cat}/K_m$ 1.2×103 $M^{-1}$ $s^{-1}$). The best variant with DMVX was L7ep-3a, which has a $k_{cat}$=28 $s^{-1}$ and a $k_{cat}/K_m$=1.3×104 $M^{-1}$ $s^{-1}$. These values are 1,300- and 680-fold better, respectively, than wild-type PTE. Wild-type PTE exhibited better catalytic activity with DEVR ($k_{cat}/K_m$=5.6×102 M−$^{1}$ $s^{-1}$). L7ep-3a also had the best catalytic activity with this analog ($k_{cat}/K_m$=1.5×104 $M^{-1}$ $s^{-1}$). With the exception of wild-type PTE ($k_{cat}/K_m$=6.8×101 $M^{-1}$ $s^{-1}$), racemic OMVR gave the least activity for most of the variants tested. The combination of poor solubility of this compound and high $K_m$ values limited analysis to the determination of $k_{cat}/K_m$ for most variants. The best mutant for the hydrolysis of OMVR was L7ep-3a with a $k_{cat}/K_m$=5.8×102 $M^{-1}$ $s^{-1}$. However, given the switch in stereochemical preference, it is highly likely that L7ep-3a I106G has the best catalytic activity with the $R_P$-enantiomer of OMVR (which corresponds to the same relative stereochemistry as the $S_P$-enantiomer of VR.

substituent, the data for DMVX suggests that for mimicking VX, the overall size of the phosphorus center is more important. While the asymmetry of the phosphonate center is obviously a major contributor to the catalytic activity using VX as a substrate, the dimethyl center provided a reasonable prediction of the catalytic activity.

The compound DEVR was synthesized to test the significance of the diethylamino vs. diisopropylamino groups contained within the VR and VX leaving groups, respectively. The smaller leaving group of DEVR resulted in 2-fold less activity compared to DEVX for wild-type PTE. Similar differences were obtained for most of the other variants. L7ep-3a I106G was the only variant where the catalytic activity with DEVR was less than 10% of the catalytic activity with DEVX. The relative activity between variants was similar with either leaving group but the reduced activity, especially manifested in the value of $k_{cat}$, suggests that the interactions of the enzyme with the leaving group maybe partially responsible for aligning the phosphorus center for nucleophilic attack. The smaller leaving group probably contributes to the lower enzymatic activity observed with VR, but comparison to the catalytic activity with DEVR also highlights the dominance of the phosphorus center. The introduction of I106G in the L7ep-3a variant resulted in a 23-fold loss of activity with DEVR, but the activity with authentic VR was improved.

In an attempt to better reflect the asymmetric phosphorus center of VR, the analog OMVR was synthesized. The PTE

TABLE 15

Kinetic constants for PTE variants with V-agent analogs[1].

| Enzyme | DMVX $k_{cat}$ ($s^{-1}$) | DMVX $K_m$ (mM) | DMVX $k_{cat}/K_m$ ($M^{-1}s^{-1}$) | DEVR $k_{cat}$ ($s^{-1}$) | DEVR $K_m$ (mM) | DEVR $k_{cat}/K_m$ ($M^{-1}s^{-1}$) | OMVR[2] $k_{cat}$ ($s^{-1}$) | OMVR[2] $K_m$ (mM) | OMVR[2] $k_{cat}/K_m$ ($M^{-1}s^{-1}$) |
|---|---|---|---|---|---|---|---|---|---|
| Wild-type | 0.021 | 1.1 | $1.9 \times 10^1$ | 0.201 | 0.38 | $5.6 \times 10^2$ | nd | nd | $6.8 \times 10^1$ |
| QF | 0.21 | 0.80 | $2.6 \times 10^2$ | 0.82 | 0.37 | $2.2 \times 10^3$ | 0.15 | 1.7 | $7.1 \times 10^1$ |
| CVQFL | 17 | 3.7 | $4.4 \times 10^3$ | 1.49 | 0.19 | $7.8 \times 10^3$ | nd | nd | $2.1 \times 10^2$ |
| VRN-VQFL | 5.1 | 0.91 | $5.5 \times 10^3$ | 3.1 | 0.36 | $8.7 \times 10^3$ | nd | nd | $5.1 \times 10^2$ |
| VRN-VQF-L308S* | 3.0 | 1.8 | $1.6 \times 10^3$ | 1.94 | 0.21 | $9.2 \times 10^3$ | nd | nd | $1.4 \times 10^2$ |
| VRN-VQFL-I106G | 0.68 | 1.6 | $4.4 \times 10^2$ | 0.47 | 0.8 | $5.9 \times 10^2$ | nd | nd | $3.3 \times 10^2$ |
| VRN-VQFL-I106G/L308S | 0.3 | 1.15 | $2.6 \times 10^2$ | 0.115 | 0.97 | $1.2 \times 10^2$ | nd | nd | $1.9 \times 10^2$ |
| L7ep-3a | 28 | 2.1 | $1.3 \times 10^4$ | 6.8 | 0.44 | $1.5 \times 10^4$ | 1.0 | 1.5 | $5.8 \times 10^2$ |
| L7ep-3a I106G | nd | nd | $1.4 \times 10^3$ | 4 | 6 | $6.7 \times 10^2$ | nd | nd | $2.7 \times 10^2$ |

*L308S mutation is a revertant to the wild-type amino acid sequence.

[1]Errors from curve fitting were less than 10% except for $k_{cat}$ and $K_m$ for L7ep3aG with DEVR.

[2]$k_{cat}/K_m$ was determined from linear fit at low concentration of racemic substrate.

Comparison of Substrate Analogs. The VX analog DEVX was successfully used to identify PTE variants for the hydrolysis of VX, but it over-estimated the activity of the wild-type enzyme and failed to detect a 100-fold increase in the catalytic activity with the QF variant.(37) DEVX was initially synthesized to mimic the O-ethyl substituent in VX, but the bulk of the diethyl phosphorus center is larger than the volume of the methylphosphonate moiety of VX. DMVX also contains an achiral phosphorus center, but the volume of the dimethyl center is more representative of authentic VX. The catalytic activity of the PTE variants with DMVX was surprisingly low, but this analog captures the much lower catalytic activity of wild-type PTE for the hydrolysis of VX and the substantial increase in activity with the QF variant. The catalytic properties for the hydrolysis of DMVX are also able to predict the high $k_{cat}$ for the hydrolysis of VX by the L7ep-3a variant. While DEVX was intended to ensure accommodation of the larger O-ethyl variants exhibited the least activity with the analog OMVR, which employs a slightly larger but asymmetric phosphorus center and the authentic leaving group of VR. Kinetic constants with racemic OMVR are about an order of magnitude smaller than is obtained with authentic VR, but the relative activity between variants is much more consistent than is seen with the other analogs. VRN-VQFL and L7ep-3a both have substantially better activity than wild-type PTE or QF for both OMVR and authentic VR. Introduction of I106G or removal of S308L in the VRN-VQFL variant (G-VRN- (VQFL (SEQ ID NO: 7), VRN-VQF (SEQ ID NO: 8), G-VRN- VQF (SEQ ID NO: 9)) resulted in somewhat diminished rates for both authentic VR and OMVR.

Example 35

Active Site Hydrogen Bonding Network. The kcat values for wild-type PTE with phosphorothiolate substrates are approximately 104-fold lower than that with its best substrates.(37, 51) In the hydrolysis of substrates such as paraoxon there is no need to protonate the leaving group. (52)

Figure 18:
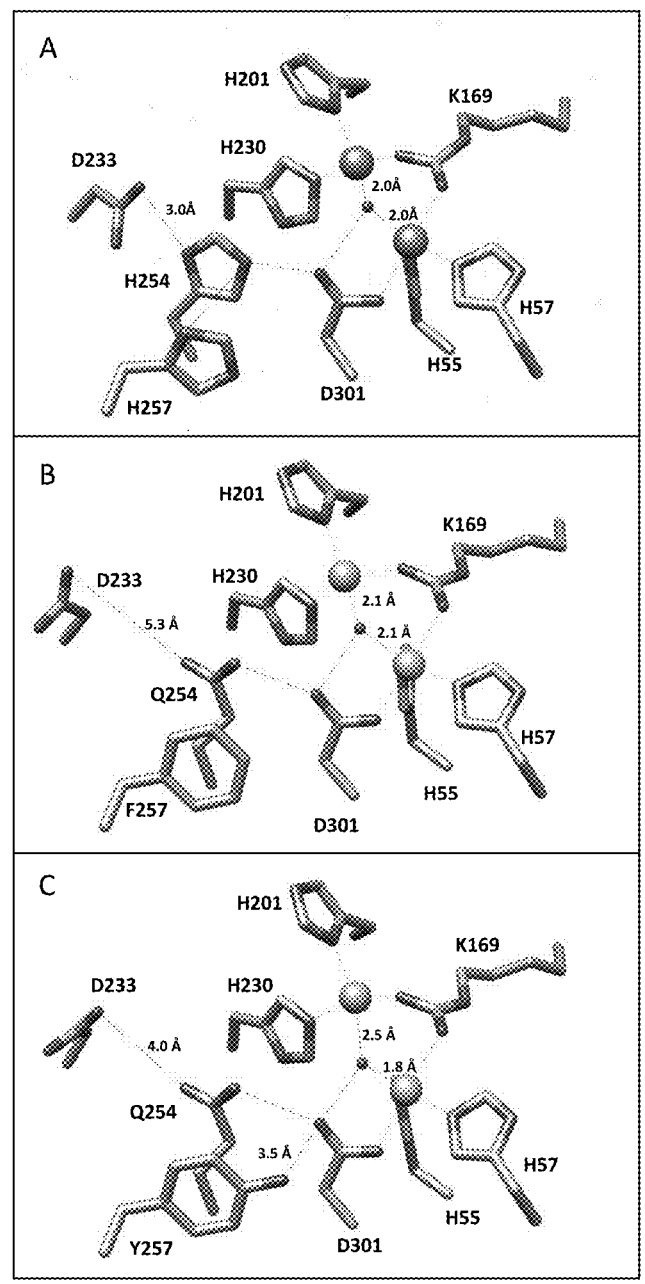
Figure 19:
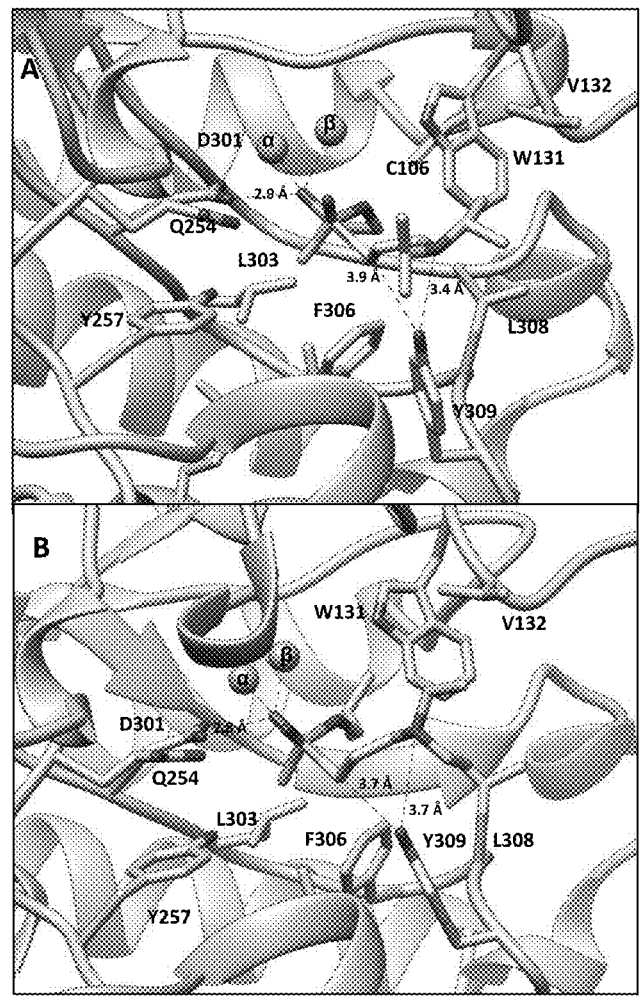
Figure 20:
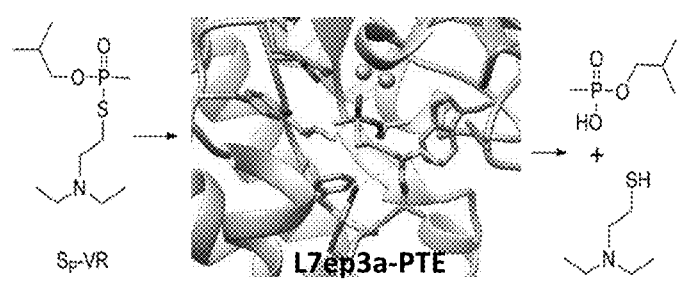
FIG. 20 depicts an equation of the interaction between $S_P$-VR and L7ep-3a PTE.

FIG. 18 depicts the metal center of wild-type PTE (A), QF (B), and L7ep-3a (C) variants. The residues binding to the α-metal (His-55, His-57, and Asp-301), the β-metal (His-201 and His-230), and the bridging carboxylated Lys-169 are shown. The proton shuttle residues His-257, His-254, and Asp-233 are also shown. The wild-type structure is obtained from PDB id: 1DPM and the QF structure is obtained from PDB id: 2OQL.

In the proposed reaction mechanism for wild-type PTE, the proton from the attacking nucleophilic water is passed to Asp-301, and, in turn, to His-254 (FIG. 18A).(53) The proton is then transferred to Asp-233 and on to bulk solvent. The variant QF has been postulated to have significantly improved catalytic activity with VX in part because of the disruption of this proton shuttle. In the crystal structure of the mutant QF, His-254 of the wild-type enzyme is a glutamine, which cannot participate in proton shuttling, and Asp-233 is moved out of hydrogen bonding distance (FIG. 18B). It is thought that the "trapping" of the proton in the active site is useful for the hydrolysis of slow substrates like VX, where protonation of the leaving group will contribute to improved $k_{cat}$ values. The crystal structure of L7ep-3a, which has a kcat value for the hydrolysis of VX about an order of magnitude higher than QF, shows a remarkable rearrangement of the hydrogen bonding pattern in the active site. In L7ep-3a, Gln-254 hydrogen bonds to Asp-301, and Asp-233 has moved back into hydrogen bonding distance to Gln-254. Tyr-257 is also hydrogen bonded to Asp-301. The dramatic alteration of the hydrogen bonding network of Asp-301 results in the displacement of the nucleophile water toward the α-metal. This asymmetrical binding to the binuclear metal center is likely to result in the bridging hydroxyl being a stronger nucleophile. In the L7ep-3a I106G mutant, a similar hydrogen bonding pattern is observed, but Asp-233 is moved out of hydrogen bonding distance and the displacement of the bridging hydroxyl is not nearly as pronounced. The asymmetric positioning of the bridging hydroxyl has previously been observed in the crystal structure of dihydroorotase in the presence of bound dihydroorotate.(54)

Example 36

Docking of Substrates in the Active Site. In an effort to gain insight into the altered activity of L7ep-3a and L7ep-3a I106G, the substrates VX and VR were docked into the active site using the program AutoDock Vina. Computational docking was conducted using the trigonal bipyrimidal intermediates formed during the hydrolysis of both enantiomers of these compounds.(55) Productive poses were assessed by the placement of the attacking hydroxyl group between the two metal ions and the orientation of the phosphoryl oxygen toward the β-metal.(56) For the wild-type and QF variants both enantiomers of VX and VR could be reasonably docked into the active site (data not shown). However, for L7ep-3a and L7ep-3a I106G, only the $S_P$-enantiomer of VR could be reasonable positioned in the active site. For both of these variants, the constriction of the active site and the repositioning of Tyr-309 appear to play important roles in the activity against the V-agents (FIG. 19).

FIG. 19 depicts (A) $S_P$-VX docked in thee active site of L7ep-3a. (B) $S_P$-VR docked into the active site of L7ep-3a I106G. The substrate binding residues are shown. The distances from Tyr-309 and Asp-301 are shown in units of Ångstoms.

The mutation F132V provides the extra room to accommodate the isopropyl amino group of VX. This effect is not as obvious with the smaller substituent contained within the leaving group in VR. The changes in the active site also enable the sulfur and the nitrogen of the leaving group to potentially hydrogen bond with the side chain phenol of Tyr-309, suggesting that this interaction may be partially responsible for the dramatically improved activity. The additional space in the small-group pocket due to the I106G mutation accommodates the isobutyl group in $S_P$-VR, while the combination of the H257Y mutation and repositioning of Tyr-309 make binding of the $R_P$-enantiomer more difficult.

The determination of the three-dimensional structure of the L7ep-3a mutant has led to a greater understanding of the underlying mechanisms by which the hydrolysis of V-agents is enhanced.

FIG. 20 depicts an equation showing the interaction between $S_P$-VR and L7ep3a-PTE resulting in hydrolysis of $S_P$-VR.

The determination of this structure has directly led to the rational construction of the new L7ep-3a I106G mutant, which is enhanced 620-fold for the hydrolysis of the toxic $S_P$-enantiomer of VR, relative to the wild-type enzyme. Previous work with the insecticide demeton-S demonstrated the importance of the leaving group on the catalytic activity of PTE, and our results with the new analogs of VR and VX has further demonstrated that even small changes in the leaving group can have dramatic effect on the activity of the enzyme.(37) The crystal structures of L7ep-3a and L7ep-3a I106G have provided a physical basis for these observations. The computational docking results have suggested how the remodeled active site is able to exploit hydrogen bonding interactions with Tyr-309. The disruption of the proton shuttle, along with new hydrogen bonds to Asp-301, are apparently able to enhance the attack of the bridging hydroxide on phosphorothiolate substrates. The initial data with the new racemic analog OMVR suggests that the combined asymmetric phosphorus center and the authentic leaving group of VR will allow for much more accurate predictions of the activity against VR and enable the more rapid development of new variants that are more fully optimized for the hydrolysis of VR.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations can be applied to the compositions and methods and in the steps or in the sequence of steps of the methods described herein without departing from the concept, spirit and scope of the disclosure. More specifically, it will be apparent that certain agents which are both chemically and physiologically related can be substituted for the agents described herein while the same or similar results would be achieved. All such similar substitutes and modifications apparent to those skilled in the art are deemed to be within the spirit, scope and concept of the disclosure as defined by the appended claims.

REFERENCES

1. Maxwell, D. M.; Brecht, K. M.; Koplovitz, I.; Sweeney, R. E. Mol. Toxicol. 2006, 80, 756.

2. Leikin, J. B.; Thomas, R. G.; Walter, F. G.; Klein, R.; Meislin, H. W. Crit. Care. Med. 2002, 30, 2346.

3. Columbus, I.; Waysbort, D.; Marcovitch, I.; Yehezkel, L.; Mizrahi, D. M. Environ. Sci. Technol. 2012, 46, 3921.

4. Yang, Y. C. Chem. Ind. 1995, 9, 334.

5. Yang, Y. C. Accounts Chem. Res. 1999, 32, 109.

6. Saxina, A.; Sun, W.; Fedorko, J. M.; Koplovitz, I.; Doctor, B. P. Biochem. Pharmacol. 2011, 81, 164.

7. Ashani, Y.; Pistinner, S. Toxicol. Sci. 2004, 77, 358.

8. Saxena, A.; Tipparaju, P.; Luo, C.; Doctor, B. P. Process Biochem. 2010, 45, 1313.

9. Cheng, T.-C.; Liu, L.; Wang, B.; Wu, J.; DeFrank, J. J.; Anderson, D. M.; Rastogi, V. K.; Hamilton, A. B. J. Ind. Microbiol. Biotechnol. 1997, 18, 49.

10. Melzer, M.; Chen, J. C.-H.; Heidenreich, A; Gab, J; Koller, M; Kehe, K; Blum, M.-M. J. Am. Chem. Soc. 2009, 131, 17226

11. Kirby, S. D.; Norris, J. R.; Smith, J. R.; Bahnson, B. J.; Cerasoli, D. M. Chem. Biol. Interact. 2012, 203, 181.

12. Gupta, R. D.; Goldsmith, M.; Ashani, Y.; Simo, Y.; Mullokandov, G.; Bar, H.; Ben-David, M.; Leader, H.; Margalit, R.; Silman, I.; Sussman, J. L.; Tawfik, D. S. Nat. Chem. Biol. 2011, 7, 120

13. Tsai, P.-C.; Fox, N.; Bigley, A. N.; Harvey, S. P.; Barondeau, D. P.; Raushel, F. M. Biochemistry 2012, 51, 6463.

14. Lai, K.; Grimsley, J. K.; Kuhlmann, B. D.; Scapozza, L.; Harvey, S. P.; DeFrank, J. J.; Kolakowski, J. E.; Wild, J. R. Chimia 1996, 50, 430.

15. Caldwell, S. R.; Newcomb, J. R.; Schlecht, K. A.; Raushel, F. M. Biochemistry 1991, 30, 7438.

16. Benschop, H. P.; De Jong, L. P. A. Accounts Chem. Res. 1988, 21, 368.

17. Ordentlich, A.; Barak, D.; Sod-Moriah, G.; Kaplan, D.; Mizrahi, D.; Segall, Y.; Kronman, C.; Karton, Y.; Lazar, A.; Marcus, D.; Velan, B.; Shafferman, A. Biochemistry 2004, 43, 11255.

18. Tsai, P. C.; Bigley, A, N.; Li, Y.; Ghanem, E.; Cadieux, C. L.; Kasten, S. A.; Reeves, T. E.; Cerasoli, D. M.; Raushel, F. M. Biochemistry 2010, 49, 7978.

19. Rastogi, V. K.; DeFrank, J. J.; Cheng, T.; Wild, J. R. Biochem. Bioph. Res. Co. 1997, 241, 294.

20. Hong, S.-B.; Raushel, F. M. Biochemistry 1996, 35, 10904.

21. Vanhooke, J. L.; Benning, M. M.; Raushel, F. M.; Holden, H. M. Biochemistry 1996, 35, 6020.

22. Chen-Goodspeed, M.; Sogorb, M. A.; Wu, F.; Hong, S.-B.; Raushel, F. M. Biochemistry 2001, 40, 1325.

23. Afriat-Jurnou, L; Jackson, C. J.; Tawfik, D. S. Biochemistry, 2012, 51, 6047.

24. Reeves, T. E.; Wales, M. E.; Grimsley, J. K.; Li, P.; Cerasoli, D. M.; Wild, J. R. Protein Eng. Des. Sel. 2008, 21, 405.

25. Schofield, D. A.; DiNovo, A. A. J. Appl. Microbiol. 2010, 109, 548

26. Horton, R. M.; Hunt, H. D.; Ho, S. N.; Pullen, J. K.; Pease, L. R. Gene 1989 77, 61

27. Goldsmith, M.; Kiss, C.; Bradbury, A. R. M.; Tawfik, D. S. Protein Eng. Del. Sel. 2007, 20, 315.

28. Cho, C. M.; Mulchandani, A.; Chen, W. Protein Eng. Del. Sel. 2006, 19, 99.

29. Roodveldt, C.; Tawfik, D. S. Protein Eng. Des. Sel. 2005, 18, 51.

30. Aubert, S. D.; Li, Y.; Raushel, F. M. Biochemistry 2004, 43, 5707.

31. Shaka, A. J.; Keeler, J.; Freeman, J. R. J. Magn. Reson. 1983, 53, 313.

32. Batley, M.; Redmond, J. W. J. Magn. Reson. 1982, 49, 172.

33. Benschop, H. P., and De Jong, L. P. A. (1988) Nerve agent stereoisomers: analysis, isolation and toxicology, Acc. Chem. Res. 21, 368-374.

34. Rosman, Y., Eisenkraft, A., Milk, N., Shiyovich, A., Ophir, N., Shrot, S., Kreiss, Y., and Kassirer, M. (2014) Lessons learned from the Syrian sarin attack: Evaluation of a clinical syndrome through social media, Ann. Intern. Med. 160, 644-648.

35. Leikin, J. B., Thomas, R. G., Walter, F. G., Klein, R., and Meislin, H. W. (2002) A review of nerve agent exposure for the critical care physician, Crit. Care Med. 30, 2346-2354.

36. Columbus, I., Waysbort, D., Marcovitch, I., Yehezkel, L., and Mizrahi, D. M. (2012) VX fate on common matrices: evaporation versus degradation, Environ. Sci. Technol. 46, 3921-3927.

37. Bigley, A. N., Xu, C., Henderson, T. J., Harvey, S. P., and Raushel, F. M. (2013) Enzymatic neutralization of the chemical warfare agent VX: evolution of phosphotriesterase for phosphorothiolate hydrolysis, J. Am. Chem. Soc. 135, 10426-10432.

38. Tsai, P. C., Fox, N., Bigley, A. N., Harvey, S. P., Barondeau, D. P., and Raushel, F. M. (2012) Enzymes for the homeland defense: Optimizing phosphotriesterase for the hydrolysis of organophosphate nerve agents, Biochemistry 51, 6463-6475.

39. Tsai, P. C., Bigley, A., Li, Y., Ghanem, E., Cadieux, C. L., Kasten, S. A., Reeves, T. E., Cerasoli, D. M., and Raushel, F. M. (2010) Stereoselective hydrolysis of organophosphate nerve agents by the bacterial phosphotriesterase, Biochemistry 49, 7978-7987.

40. Mee-Hie Cho, C., Mulchandani, A., and Chen, W. (2006) Functional analysis of organophosphorus hydrolase variants with high degradation activity towards organophosphate pesticides, Protein Eng., Des. Sel. 19, 99-105.

41. Roodveldt, C., and Tawfik, D. S. (2005) Directed evolution of phosphotriesterase from *Pseudomonas diminuta* for heterologous expression in *Escherichia coli* results in stabilization of the metal-free state, Protein Eng., Des. Sel. 18, 51-58.

42. Rastogi, V. K., DeFrank, J. J., Cheng, T. C., and Wild, J. R. (1997) Enzymatic hydrolysis of Russian-VX by organophosphorus hydrolase, Biochem. Biophys. Res. Commun. 241, 294-296.

43. Cherny, I., Greisen, P., Jr., Ashani, Y., Khare, S. D., Oberdorfer, G., Leader, H., Baker, D., and Tawfik, D. S. (2013) Engineering V-type nerve agents detoxifying enzymes using computationally focused libraries, ACS chem. Biol. 8, 2394-2403.

44. Amitai, G., Ashani, Y., Grunfeld, Y., Kalir, A., and Cohen, S. (1976) Synthesis and properties of 2-S—(N,N-dialkylamino)ethyl)thio-1,3,2-dioxaphosphorinane 2-oxide and of the corresponding quaternary derivatives as potential nontoxic antiglaucoma agents, J. Med. Chem. 19, 810-813.

45. Michaelis, L., and Menten, M. L. (1913) Die kinetik der invertinwirkung, Biochem. Z. 49, 333-369.

46. Otwinowski Z, M. W. (1997) Processing of X-ray diffraction data collected in oscillation mode, Methods Enzymol. 276A, 307-326.

47. Adams, P. D., Afonine, P. V., Bunkoczi, G., Chen, V. B., Davis, I. W., Echols, N., Headd, J. J., Hung, L.-W., Kapral, G. J., Grosse-Kunstleve, R. W., McCoy, A. J., Moriarty, N. W., Oeffner, R., Read, R. J., Richardson, D. C., Richardson, J. S., Terwilliger, T. C., and Zwart, P. H. (2010) PHENIX: a comprehensive Python-based system for macromolecular structure solution, Acta Crystallogr., Sect. D: Biol. Crystallogr. 66, 213-221.

48. Emsley, P., and Cowtan, K. (2004) Coot: model-building tools for molecular graphics, Acta Crystallogr., Sect. D: Biol. Crystallogr. 60, 2126-2132.

49. Trott, O., and Olson, A. J. (2010) AutoDock Vina: Improving the speed and accuracy of docking with a new scoring function, efficient optimization, and multithreading, J. Comput. Chem. 31, 455-461.

50. Chen-Goodspeed, M., Sogorb, M. A., Wu, F., Hong, S. B., and Raushel, F. M. (2001) Structural determinants of the substrate and stereochemical specificity of phosphotriesterase, Biochemistry 40, 1325-1331.

51. Caldwell, S. R., Newcomb, J. R., Schlecht, K. A., and Raushel, F. M. (1991) Limits of diffusion in the hydrolysis of substrates by the phosphotriesterase from *Pseudomonas diminuta*, Biochemistry 30, 7438-7444.

52. Hong, S. B., and Raushel, F. M. (1996) Metal-substrate interactions facilitate the catalytic activity of the bacterial phosphotriesterase, Biochemistry 35, 10904-10912.

53. Aubert, S. D., Li, Y., and Raushel, F. M. (2004) Mechanism for the hydrolysis of organophosphates by the bacterial phosphotriesterase, Biochemistry 43, 5707-5715.

54. Thoden, J. B., Phillips, G. N., Neal, T. M., Raushel, F. M., and Holden, H. M. (2001) Molecular Structure of Dihydroorotase: A paradigm for catalysis through the use of a binuclear metal center, Biochemistry 40, 6989-6997.

55. Caldwell, S. R., Raushel, F. M., Weiss, P. M., and Cleland, W. W. (1991) Transition-state structures for enzymatic and alkaline phosphotriester hydrolysis, Biochemistry 30, 7444-7450.

56. Vanhooke, J. L., Benning, M. M., Raushel, F. M., and Holden, H. M. (1996) Three-dimensional structure of the zinc-containing phosphotriesterase with the bound substrate analog diethyl 4-methylbenzylphosphonate, Biochemistry 35, 6020-6025.

What is claimed is:

1. A synthetic amino acid sequence comprising the amino acid sequence of L7ep-3a (SEQ ID NO: 5) and functioning by hydrolyzing an organophosphate nerve agent.

SEQUENCE LISTING

```
<160> NUMBER OF SEQ ID NOS: 9

<210> SEQ ID NO 1
<211> LENGTH: 337
<212> TYPE: PRT
<213> ORGANISM: Brevundimonas diminuta

<400> SEQUENCE: 1

Met Ser Ile Gly Thr Gly Asp Arg Ile Asn Thr Val Arg Gly Pro Ile
1               5                   10                  15

Thr Ile Ser Glu Ala Gly Phe Thr Leu Thr His Glu His Ile Cys Gly
            20                  25                  30

Ser Ser Ala Gly Phe Leu Arg Ala Trp Pro Glu Phe Phe Gly Ser Arg
        35                  40                  45

Lys Ala Leu Ala Glu Lys Ala Val Arg Gly Leu Arg Arg Ala Arg Ala
50                  55                  60

Ala Gly Val Arg Thr Ile Val Asp Val Ser Thr Phe Asp Ile Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Phe Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
    130                 135                 140

Thr Gly Lys Ala Thr Pro Phe Gln Glu Leu Val Leu Lys Ala Ala Ala
145                 150                 155                 160

Arg Ala Ser Leu Ala Thr Gly Val Pro Val Thr Thr His Thr Ala Ala
                165                 170                 175

Ser Gln Arg Asp Gly Glu Gln Gln Ala Ala Ile Phe Glu Ser Glu Gly
            180                 185                 190

Leu Ser Pro Ser Arg Val Cys Ile Gly His Ser Asp Asp Thr Asp Asp
        195                 200                 205

Leu Ser Tyr Leu Thr Ala Leu Ala Ala Arg Gly Tyr Leu Ile Gly Leu
    210                 215                 220
```

```
Asp His Ile Pro His Ser Ala Ile Gly Leu Glu Asp Asn Ala Ser Ala
225                 230                 235                 240

Ser Ala Leu Leu Gly Ile Arg Ser Trp Gln Thr Arg Ala Leu Leu Ile
            245                 250                 255

Lys Ala Leu Ile Asp Gln Gly Tyr Met Lys Gln Ile Leu Val Ser Asn
        260                 265                 270

Asp Trp Leu Phe Gly Phe Ser Ser Tyr Val Thr Asn Ile Met Asp Val
            275                 280                 285

Met Asp Arg Val Asn Pro Asp Gly Met Ala Phe Ile Pro Leu Arg Val
    290                 295                 300

Ile Pro Phe Leu Arg Glu Lys Gly Val Pro Gln Glu Thr Leu Ala Gly
305                 310                 315                 320

Ile Thr Val Thr Asn Pro Ala Arg Phe Leu Ser Pro Thr Leu Arg Ala
                325                 330                 335

Ser

<210> SEQ ID NO 2
<211> LENGTH: 337
<212> TYPE: PRT
<213> ORGANISM: Brevundimonas diminuta

<400> SEQUENCE: 2

Met Ser Ile Gly Thr Gly Asp Arg Ile Asn Thr Val Arg Gly Pro Ile
1               5                   10                  15

Thr Ile Ser Glu Ala Gly Phe Thr Leu Thr His Glu His Ile Cys Gly
            20                  25                  30

Ser Ser Ala Gly Phe Leu Arg Ala Trp Pro Glu Phe Phe Gly Ser Arg
        35                  40                  45

Lys Ala Leu Ala Glu Lys Ala Val Arg Gly Leu Arg Arg Ala Arg Ala
    50                  55                  60

Ala Gly Val Arg Thr Ile Val Asp Val Ser Thr Phe Asp Ile Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Val Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
    130                 135                 140

Thr Gly Lys Ala Thr Pro Phe Gln Glu Leu Val Leu Lys Ala Ala Ala
145                 150                 155                 160

Arg Ala Ser Leu Ala Thr Gly Val Pro Val Thr Thr His Thr Ala Ala
                165                 170                 175

Ser Gln Arg Asp Gly Glu Gln Gln Ala Ala Ile Phe Glu Ser Glu Gly
            180                 185                 190

Leu Ser Pro Ser Arg Val Cys Ile Gly His Ser Asp Asp Thr Asp Asp
        195                 200                 205

Leu Ser Tyr Leu Thr Ala Leu Ala Ala Arg Gly Tyr Leu Ile Gly Leu
    210                 215                 220

Asp Gln Ile Pro Phe Ser Ala Ile Gly Leu Glu Asp Asn Ala Ser Ala
225                 230                 235                 240

Ser Ala Leu Leu Gly Ile Arg Ser Trp Gln Thr Arg Ala Leu Leu Ile
                245                 250                 255
```

Lys Ala Leu Ile Asp Gln Gly Tyr Met Lys Gln Ile Leu Val Ser Asn
            260                 265                 270

Asp Trp Leu Phe Gly Phe Ser Leu Tyr Val Thr Asn Ile Met Asp Val
        275                 280                 285

Met Asp Arg Val Asn Pro Asp Gly Met Ala Phe Ile Pro Leu Arg Val
    290                 295                 300

Ile Pro Phe Leu Arg Glu Lys Gly Val Pro Gln Glu Thr Leu Ala Gly
305                 310                 315                 320

Ile Thr Val Thr Asn Pro Ala Arg Phe Leu Ser Pro Thr Leu Arg Ala
                325                 330                 335

Ser

<210> SEQ ID NO 3
<211> LENGTH: 337
<212> TYPE: PRT
<213> ORGANISM: Brevundimonas diminuta

<400> SEQUENCE: 3

Met Ser Ile Gly Thr Gly Asp Arg Ile Asn Thr Val Arg Gly Pro Ile
1               5                   10                  15

Thr Ile Ser Glu Ala Gly Phe Thr Leu Thr His Glu His Ile Cys Gly
            20                  25                  30

Ser Ser Ala Gly Phe Leu Arg Ala Trp Pro Glu Phe Phe Gly Ser Arg
        35                  40                  45

Lys Ala Leu Ala Glu Lys Ala Val Arg Gly Leu Arg Arg Ala Arg Ala
    50                  55                  60

Ala Gly Val Arg Thr Ile Val Asp Val Ser Arg Thr Phe Asp Cys Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Val Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
130                 135                 140

Thr Gly Lys Ala Thr Pro Phe Gln Glu Leu Val Leu Lys Ala Ala Ala
145                 150                 155                 160

Arg Ala Ser Leu Ala Thr Gly Val Pro Val Thr Thr His Thr Ala Ala
                165                 170                 175

Ser Gln Arg Asp Gly Glu Gln Gln Ala Ala Ile Phe Glu Ser Glu Gly
            180                 185                 190

Leu Ser Pro Ser Arg Val Cys Ile Gly His Ser Asp Thr Asp Asp
        195                 200                 205

Leu Ser Tyr Leu Thr Ala Leu Ala Ala Arg Gly Tyr Leu Ile Gly Leu
    210                 215                 220

Asp Gln Ile Pro Phe Ser Ala Ile Gly Leu Glu Asp Asn Ala Ser Ala
225                 230                 235                 240

Ser Ala Leu Leu Gly Ile Arg Ser Trp Gln Thr Arg Ala Leu Leu Ile
                245                 250                 255

Lys Ala Leu Ile Asp Gln Gly Tyr Met Lys Gln Ile Leu Val Ser Asn
            260                 265                 270

Asp Trp Leu Phe Gly Phe Ser Leu Tyr Val Thr Asn Ile Met Asp Val
        275                 280                 285

```
Met Asp Arg Val Asn Pro Asp Gly Met Ala Phe Ile Pro Leu Arg Val
290                 295                 300

Ile Pro Phe Leu Arg Glu Lys Gly Val Pro Gln Glu Thr Leu Ala Gly
305                 310                 315                 320

Ile Thr Val Thr Asn Pro Ala Arg Phe Leu Ser Pro Thr Leu Arg Ala
                325                 330                 335

Ser

<210> SEQ ID NO 4
<211> LENGTH: 337
<212> TYPE: PRT
<213> ORGANISM: Brevundimonas diminuta

<400> SEQUENCE: 4

Met Ser Ile Gly Thr Gly Asp Arg Ile Asn Thr Val Arg Gly Pro Ile
1               5                   10                  15

Thr Ile Ser Glu Ala Gly Phe Thr Leu Thr His Glu His Ile Cys Gly
                20                  25                  30

Ser Ser Ala Gly Phe Leu Arg Ala Trp Pro Glu Phe Phe Gly Ser Arg
            35                  40                  45

Lys Ala Leu Val Glu Lys Ala Val Arg Gly Leu Arg Arg Ala Arg Ala
50                  55                  60

Ala Gly Val Arg Thr Ile Val Asp Val Ser Thr Phe Asp Ile Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Val Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
130                 135                 140

Thr Gly Lys Ala Thr Pro Phe Gln Glu Leu Val Leu Arg Ala Ala Ala
145                 150                 155                 160

Arg Ala Ser Leu Ala Thr Gly Val Pro Val Thr Thr His Thr Ala Ala
                165                 170                 175

Ser Gln Arg Asp Gly Glu Gln Gln Ala Ala Ile Phe Glu Ser Glu Gly
            180                 185                 190

Leu Ser Pro Ser Arg Val Cys Ile Gly His Ser Asp Asp Thr Asp Asp
        195                 200                 205

Leu Ser Tyr Leu Thr Ala Leu Ala Ala Arg Gly Tyr Leu Ile Gly Leu
210                 215                 220

Asp Gln Ile Pro Phe Ser Ala Ile Gly Leu Glu Asp Asn Ala Ser Ala
225                 230                 235                 240

Ser Ala Leu Leu Gly Asn Arg Ser Trp Gln Thr Arg Ala Leu Leu Ile
                245                 250                 255

Lys Ala Leu Ile Asp Gln Gly Tyr Met Lys Gln Ile Leu Val Ser Asn
            260                 265                 270

Asp Trp Leu Phe Gly Phe Ser Leu Tyr Val Thr Asn Ile Met Asp Val
        275                 280                 285

Met Asp Arg Val Asn Pro Asp Gly Met Ala Phe Ile Pro Leu Arg Val
290                 295                 300

Ile Pro Phe Leu Arg Glu Lys Gly Val Pro Gln Glu Thr Leu Ala Gly
305                 310                 315                 320
```

```
Ile Thr Val Thr Asn Pro Ala Arg Phe Leu Ser Pro Thr Leu Arg Ala
            325                 330                 335

Ser

<210> SEQ ID NO 5
<211> LENGTH: 337
<212> TYPE: PRT
<213> ORGANISM: Brevundimonas diminuta
<300> PUBLICATION INFORMATION:
<301> AUTHORS: Ping-Chuan Tsai, Nicholas Fox, Andrew N. Bigley, Steven
      P. Harvey, David P. Barondeau, and Frank M. Raushel
<302> TITLE: Enzymes for the Homeland Defense: Optimizing
      Phosphotriesterase for the Hydrolysis of Organophosphate Nerve
      Agents
<303> JOURNAL: Biochemistry
<304> VOLUME: 51
<306> PAGES: 6463-6475

```
Lys Ala Leu Ile Asp Gln Gly Tyr Met Lys Gln Ile Leu Val Ser Asn
                260                 265                 270

Asp Trp Leu Phe Gly Phe Ser Leu Tyr Val Thr Asn Ile Met Asp Val
            275                 280                 285

Met Asp Arg Val Asn Pro Asp Gly Met Ala Phe Ile Pro Leu Arg Val
        290                 295                 300

Ile Pro Phe Leu Arg Glu Lys Gly Val Pro Gln Glu Thr Leu Ala Gly
305                 310                 315                 320

Ile Thr Val Thr Asn Pro Ala Arg Phe Leu Ser Pro Thr Leu Arg Ala
                325                 330                 335

Ser

<210> SEQ ID NO 6
<211> LENGTH: 337
<212> TYPE: PRT
<213> ORGANISM: Brevundimonas diminuta

<400> SEQUENCE: 6

Met Ser Ile Gly Thr Gly Asp Arg Ile Asn Thr Val Arg Gly Pro Ile
1               5                   10                  15

Thr Ile Ser Glu Ala Gly Phe Thr Leu Thr His Glu His Ile Cys Gly
            20                  25                  30

Ser Ser Ala Gly Phe Leu Arg Ala Trp Pro Glu Phe Phe Gly Ser Arg
        35                  40                  45

Lys Ala Leu Ala Glu Lys Ala Val Arg Gly Leu Arg Arg Ala Arg Ala
    50                  55                  60

Ala Gly Val Arg Thr Ile Val Asp Val Ser Arg Thr Phe Asp Gly Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Val Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
130                 135                 140

Thr Gly Lys Ala Thr Pro Phe Gln Glu Leu Val Leu Lys Ala Ala Ala
145                 150                 155                 160

Arg Ala Ser Leu Ala Thr Gly Val Pro Val Thr Thr His Thr Ala Ala
                165                 170                 175

Ser Gln Arg Asp Gly Glu Gln Gln Ala Ala Ile Phe Glu Ser Glu Gly
            180                 185                 190

Leu Ser Pro Ser Arg Val Cys Ile Gly His Ser Asp Thr Asp Asp
        195                 200                 205

Leu Ser Tyr Leu Thr Ala Leu Ala Ala Arg Gly Tyr Leu Ile Gly Leu
    210                 215                 220

Asp Gln Ile Pro Tyr Ser Ala Ile Gly Leu Glu Asp Asn Ala Ser Ala
225                 230                 235                 240

Ser Val Leu Met Gly Asn Arg Ser Trp Gln Thr Arg Ala Leu Leu Ile
                245                 250                 255

Lys Ala Leu Ile Asp Gln Gly Tyr Met Lys Gln Ile Leu Val Ser Asn
            260                 265                 270

Asp Trp Leu Phe Gly Phe Ser Leu Tyr Val Thr Asn Ile Met Asp Val
        275                 280                 285
```

```
Met Asp Arg Val Asn Pro Asp Gly Met Ala Phe Ile Pro Leu Arg Val
            290                 295                 300

Ile Pro Phe Leu Arg Glu Lys Gly Val Pro Gln Glu Thr Leu Ala Gly
305                 310                 315                 320

Ile Thr Val Thr Asn Pro Ala Arg Phe Leu Ser Pro Thr Leu Arg Ala
                325                 330                 335

Ser

<210> SEQ ID NO 7
<211> LENGTH: 337
<212> TYPE: PRT
<213> ORGANISM: Brevundimonas diminuta

<400> SEQUENCE: 7

Met Ser Ile Gly Thr Gly Asp Arg Ile Asn Thr Val Arg Gly Pro Ile
1               5                   10                  15

Thr Ile Ser Glu Ala Gly Phe Thr Leu Thr His Glu His Ile Cys Gly
            20                  25                  30

Ser Ser Ala Gly Phe Leu Arg Ala Trp Pro Glu Phe Phe Gly Ser Arg
        35                  40                  45

Lys Ala Leu Val Glu Lys Ala Val Arg Gly Leu Arg Arg Ala Arg Ala
50                  55                  60

Ala Gly Val Arg Thr Ile Val Asp Val Ser Thr Phe Asp Gly Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Val Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
130                 135                 140

Thr Gly Lys Ala Thr Pro Phe Gln Glu Leu Val Leu Arg Ala Ala Ala
145                 150                 155                 160

Arg Ala Ser Leu Ala Thr Gly Val Pro Val Thr Thr His Thr Ala Ala
                165                 170                 175

Ser Gln Arg Asp Gly Glu Gln Ala Ala Ile Phe Glu Ser Glu Gly
            180                 185                 190

Leu Ser Pro Ser Arg Val Cys Ile Gly His Ser Asp Thr Asp Asp
        195                 200                 205

Leu Ser Tyr Leu Thr Ala Leu Ala Ala Arg Gly Tyr Leu Ile Gly Leu
210                 215                 220

Asp Gln Ile Pro Phe Ser Ala Ile Gly Leu Glu Asp Asn Ala Ser Ala
225                 230                 235                 240

Ser Ala Leu Leu Gly Asn Arg Ser Trp Gln Thr Arg Ala Leu Leu Ile
                245                 250                 255

Lys Ala Leu Ile Asp Gln Gly Tyr Met Lys Gln Ile Leu Val Ser Asn
            260                 265                 270

Asp Trp Leu Phe Gly Phe Ser Leu Tyr Val Thr Asn Ile Met Asp Val
        275                 280                 285

Met Asp Arg Val Asn Pro Asp Gly Met Ala Phe Ile Pro Leu Arg Val
            290                 295                 300

Ile Pro Phe Leu Arg Glu Lys Gly Val Pro Gln Glu Thr Leu Ala Gly
305                 310                 315                 320
```

```
Ile Thr Val Thr Asn Pro Ala Arg Phe Leu Ser Pro Thr Leu Arg Ala
            325                 330                 335

Ser

<210> SEQ ID NO 8
<211> LENGTH: 337
<212> TYPE: PRT
<213> ORGANISM: Brevundimonas diminuta

<400> SEQUENCE: 8

Met Ser Ile Gly Thr Gly Asp Arg Ile Asn Thr Val Arg Gly Pro Ile
1               5                   10                  15

Thr Ile Ser Glu Ala Gly Phe Thr Leu Thr His Glu His Ile Cys Gly
            20                  25                  30

Ser Ser Ala Gly Phe Leu Arg Ala Trp Pro Glu Phe Phe Gly Ser Arg
        35                  40                  45

Lys Ala Leu Val Glu Lys Ala Val Arg Gly Leu Arg Arg Ala Arg Ala
    50                  55                  60

Ala Gly Val Arg Thr Ile Val Asp Val Ser Thr Phe Asp Ile Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Val Asp Pro Pro Leu Ser Met Arg Leu
            100                 105                 110

Arg Ser Val Glu Glu Leu Thr Gln Phe Phe Leu Arg Glu Ile Gln Tyr
        115                 120                 125

Gly Ile Glu Asp Thr Gly Ile Arg Ala Gly Ile Ile Lys Val Ala Thr
    130                 135                 140

Thr Gly Lys Ala Thr Pro Phe Gln Glu Leu Val Leu Arg Ala Ala Ala
145                 150                 155                 160

Arg Ala Ser Leu Ala Thr Gly Val Pro Val Thr Thr His Thr Ala Ala
                165                 170                 175

Ser Gln Arg Asp Gly Glu Gln Gln Ala Ala Ile Phe Glu Ser Glu Gly
            180                 185                 190

Leu Ser Pro Ser Arg Val Cys Ile Gly His Ser Asp Asp Thr Asp Asp
        195                 200                 205

Leu Ser Tyr Leu Thr Ala Leu Ala Ala Arg Gly Tyr Leu Ile Gly Leu
    210                 215                 220

Asp Gln Ile Pro Phe Ser Ala Ile Gly Leu Glu Asp Asn Ala Ser Ala
225                 230                 235                 240

Ser Ala Leu Leu Gly Asn Arg Ser Trp Gln Thr Arg Ala Leu Leu Ile
                245                 250                 255

Lys Ala Leu Ile Asp Gln Gly Tyr Met Lys Gln Ile Leu Val Ser Asn
            260                 265                 270

Asp Trp Leu Phe Gly Phe Ser Ser Tyr Val Thr Asn Ile Met Asp Val
        275                 280                 285

Met Asp Arg Val Asn Pro Asp Gly Met Ala Phe Ile Pro Leu Arg Val
    290                 295                 300

Ile Pro Phe Leu Arg Glu Lys Gly Val Pro Gln Glu Thr Leu Ala Gly
305                 310                 315                 320

Ile Thr Val Thr Asn Pro Ala Arg Phe Leu Ser Pro Thr Leu Arg Ala
                325                 330                 335

Ser
```

```
<210> SEQ ID NO 9
<211> LENGTH: 337
<212> TYPE: PRT
<213> ORGANISM: Brevundimonas diminuta

<400> SEQUENCE: 9

Met Ser Ile Gly Thr Gly Asp Arg Ile Asn Thr Val Arg Gly Pro Ile
1               5                   10                  15

Thr Ile Ser Glu Ala Gly Phe Thr Leu Thr His Glu His Ile Cys Gly
            20                  25                  30

Ser Ser Ala Gly Phe Leu Arg Ala Trp Pro Glu Phe Gly Ser Arg
        35                  40                  45

Lys Ala Leu Val Glu Lys Ala Val Arg Gly Leu Arg Arg Ala Arg Ala
    50                  55                  60

Ala Gly Val Arg Thr Ile Val Asp Val Ser Thr Phe Asp Gly Arg
65                  70                  75                  80

Asp Val Ser Leu Leu Ala Glu Val Ser Arg Ala Ala Asp Val His Ile
                85                  90                  95

Val Ala Ala Thr Gly Leu Trp Val Asp Pro Pro Leu Ser Met Arg Leu
                100                 105                 110

Arg Ser Val Glu Glu Leu Thr Gln Phe Phe Leu Arg Glu Ile Gln Tyr
            115                 120                 125

Gly Ile Glu Asp Thr Gly Ile Arg Ala Gly Ile Ile Lys Val Ala Thr
130                 135                 140

Thr Gly Lys Ala Thr Pro Phe Gln Glu Leu Val Leu Arg Ala Ala Ala
145                 150                 155                 160

Arg Ala Ser Leu Ala Thr Gly Val Pro Val Thr Thr His Thr Ala Ala
                165                 170                 175

Ser Gln Arg Asp Gly Glu Gln Gln Ala Ala Ile Phe Glu Ser Glu Gly
            180                 185                 190

Leu Ser Pro Ser Arg Val Cys Ile Gly His Ser Asp Asp Thr Asp Asp
        195                 200                 205

Leu Ser Tyr Leu Thr Ala Leu Ala Ala Arg Gly Tyr Leu Ile Gly Leu
    210                 215                 220

Asp Gln Ile Pro Phe Ser Ala Ile Gly Leu Glu Asp Asn Ala Ser Ala
225                 230                 235                 240

Ser Ala Leu Leu Gly Asn Arg Ser Trp Gln Thr Arg Ala Leu Leu Ile
                245                 250                 255

Lys Ala Leu Ile Asp Gln Gly Tyr Met Lys Gln Ile Leu Val Ser Asn
            260                 265                 270

Asp Trp Leu Phe Gly Phe Ser Ser Tyr Val Thr Asn Ile Met Asp Val
        275                 280                 285

Met Asp Arg Val Asn Pro Asp Gly Met Ala Phe Ile Pro Leu Arg Val
    290                 295                 300

Ile Pro Phe Leu Arg Glu Lys Gly Val Pro Gln Glu Thr Leu Ala Gly
305                 310                 315                 320

Ile Thr Val Thr Asn Pro Ala Arg Phe Leu Ser Pro Thr Leu Arg Ala
                325                 330                 335

Ser
```